(12) United States Patent
Nakamura et al.

(10) Patent No.: US 8,044,193 B2
(45) Date of Patent: Oct. 25, 2011

(54) SHORT INTERFERING RNAS TARGETED TO T-LAK CELL-ORIGINATED PROTEIN KINASE (TOPK) POLYNUCLEOTIDE

(75) Inventors: Yusuke Nakamura, Tokyo (JP); Toyomasa Katagiri, Tokyo (JP); Shuichi Nakatsuru, Saitama (JP)

(73) Assignee: Oncotherapy Science, Inc., Kanagawa (JP)

( * ) Notice: Subject to any disclaimer, the term of this patent is extended or adjusted under 35 U.S.C. 154(b) by 306 days.

(21) Appl. No.: 12/416,900

(22) Filed: Apr. 1, 2009

(65) Prior Publication Data
US 2009/0286856 A1   Nov. 19, 2009

Related U.S. Application Data

(62) Division of application No. 10/573,297, filed as application No. PCT/JP2004/014438 on Sep. 24, 2004, now Pat. No. 7,531,300.

(60) Provisional application No. 60/505,571, filed on Sep. 24, 2003.

(51) Int. Cl.
*A61K 31/70* (2006.01)
*C07H 21/04* (2006.01)

(52) U.S. Cl. .................. 536/24.5; 514/44

(58) Field of Classification Search .............. None
See application file for complete search history.

(56) References Cited

U.S. PATENT DOCUMENTS

| | | | |
|---|---|---|---|
| 6,365,358 B1 | 4/2002 | Hillman et al. | |
| 2003/0104418 A1 | 6/2003 | Zhang et al. | |
| 2003/0157544 A1 | 8/2003 | Gish et al. | |
| 2004/0005563 A1 | 1/2004 | Mack et al. | |
| 2005/0064402 A1 | 3/2005 | Goldsworthy et al. | |

FOREIGN PATENT DOCUMENTS

| | | |
|---|---|---|
| WO | WO 02/04514 A2 | 1/2002 |
| WO | WO 02/29104 A2 | 4/2002 |
| WO | WO 2004/031410 A2 | 4/2004 |
| WO | WO 2006/085684 A2 | 8/2006 |
| WO | WO 2008/018642 A2 | 2/2008 |

OTHER PUBLICATIONS

Pages 1-35 and 182 of WO 2004094636 A1 (38 pages total).*
U.S. Appl. No. 12/377,024, which is a U.S. Nat'l Phase of PCT/JP2007/065992, filed Aug. 10, 2007, 221 pgs.
U.S. Appl. No. 12/673,432, which is a U.S. Nat'l Phase of PCT/JP2008/064437, filed Aug. 12, 2008, 83 pgs.
U.S. Appl. No. 12/673,434, which is a US National Stage (371) of PCT/JP2008/060837, 102 pgs.
Abe, Y., et al., "Cloning and expression of a novel MAPKK-like protein kinase, lymphokine-activated killer T-cell originated protein kinase, specifically expressed in the testis and activated lymphoid cells," *The Journal of Biological Chemistry*, 275(28):21525-21531 (Jul. 14, 2000).
Adam, Paul J. et al.; "Arylamine N-acetyltransferase-1 is highly expressed in breast cancers and conveys enhanced growth and resistance to etoposide in vitro"; *Molecular Cancer Research* 1:826-835 (Sep. 2003).
Database EBI Accession No. AAM56211; "Sequence 1 from patent US 6365358" Jun. 20, 2002.
Database; EBI Accession No. AX369194; "Sequence from patent WO0204514"; Feb. 15, 2002.
Dermer, 1994, Bio/technology, 12: 320.
Dressman, Marlene A. et al.; "Gene expression in profiling detects gene amplification and differentiates tumor types in breast cancer"; *Cancer Research* 63:2194-2199 (May 1, 2003).
Freshney (Culture of Animal Cells, A Manual of Basic Technique, Alan R. Liss, Inc. 1983, New York, p. 4).
Gaudet, S., et al., "Characterization of PDZ-binding kinase, a mitotic kinase," *Proc. Natl. Acad. Sci. USA*, 97(10): 5167-5172 (May 9, 2000).
Geylan, Y.S. et al.; "Arylamine N-acetyltransferase activities in human breast cancer tissues"; *Neoplasma* 48(2):108-111 (2001).
Gura, "Cancer Models: Systems for Identifying New Drugs Are Often Faulty," 1997, Science, 278: pp. 1041-1042.
Lipkowitz, Stan; "The role of ubiquitination-proteasome pathway in breast cancer: Ubiquitin mediated degradation of growth factor receptors in the pathogenesis and treatment of cancer"; *Breast Cancer Research* 5(1):8-15 (2003).
Matsumoto et al., Biochemical and Biophysical Research Communications, Dec. 2004, 32:997-1004.
Orlowski, Robert Z. and E. Claire Dees; "The role of ubiquitination-proteasome pathway in breast cancer: Applying drugs that affect the ubiquitin-proteasome pathway to the therapy of breast cancer"; *Breast Cancer Research* 5(1):1-7 (2003).
Perou, Charles M. et al.; "Molecular portraits of human breast tumors"; *Nature* 406:747-752 (Aug. 17, 2000).
Sgroi, Dennis C. et al.; "In vivo gene expression profile analysis of human breast cancer progression"; *Cancer Research* 59:5656-5661 (Nov. 15, 1999).
Zhao, S., et al., "PDZ-binding kinase participates in spermatogenesis," *Int. J. of Biochem. & Cell Biol.*, 33(6): 631-636 (Jun. 2001).
Keydar, I., et al., "Establishment of Characterization of a Cell Line of Human Breast Carcinoma Origin," *Eur. J. Cancer*, vol. 15(5), pp. 659-670 (May 1979).

(Continued)

*Primary Examiner* — Tracy Vivlemore
(74) *Attorney, Agent, or Firm* — Kilpatrick Townsend & Stockton LLP

(57) ABSTRACT

Objective methods for detecting and diagnosing breast cancer (BRC) are described herein. In one embodiment, the diagnostic method involves determining the expression level of a BRC-associated gene that discriminates between BRC cells and normal cells. In another embodiment, the diagnostic method involves determining the expression level of a BRC-associated gene that discriminates among BRC cells, between DCIS and IDC cells. The present invention further provides means for predicting and preventing breast cancer metastasis using BRC-associated genes having unique altered expression patterns in breast cancer cells with lymph-node metastasis. Finally, the present invention provides methods of screening for therapeutic agents useful in the treatment of breast cancer, methods of treating breast cancer and method for vaccinating a subject against breast cancer.

1 Claim, 13 Drawing Sheets

OTHER PUBLICATIONS

Park, J-H., et al., "PDZ-Binding Kinase/T-LAK Cell-Originated Protein Kinase, a Putative Cancer/Testis Antigen with an Oncogenic Activity in Breast Cancer," *Cancer Res.*, vol. 66(18), pp. 9186-8195 (Sep. 15, 2006).

Park, J-H., et al., "PBK/TOPK (PDZ-binding kinase/T-LAK cell-originated protein kinase) as a novel molecular target for breast cancer therapy," *Proceedings of the 66th Annual Meeting of the Japanese Cancer Association*, p. 78, Abstract No. EW17-4 (Aug, 25, 2007).

Watanabe, T., et al., "Identification and characterization of a novel gene *CXADRL1* whose expression is frequently up-regulated in differentiated-type of gastric cancer," *Proceedings of the 61st Annual Meeting of the Japanese Cancer Association*, p. 77, Abstract No. 2027 (Aug. 25, 2002).

\* cited by examiner a

DAPI | Alexa488 anti-HA
Alexa594 TOPK-Ab | Merge

FIG. 10-2

(C) All Cases

|  |  | Lymph-node status | | Total |
|---|---|---|---|---|
|  |  | (+) | (−) |  |
| PS | Positive | 37 | 2 | 39 |
| PS | Negative | 0 | 38 | 38 |
| Total | | 37 | 40 | 77 |

P<0.001
($\chi^2$ test for independence)

Test Cases

|  |  | Lymph-node status | | Total |
|---|---|---|---|---|
|  |  | (+) | (−) |  |
| PS | Positive | 17 | 2 | 19 |
| PS | Negative | 0 | 18 | 18 |
| Total | | 17 | 20 | 37 |

P<0.001
($\chi^2$ test for independence)

SHORT INTERFERING RNAS TARGETED TO T-LAK CELL-ORIGINATED PROTEIN KINASE (TOPK) POLYNUCLEOTIDE

This application is a division of U.S. application Ser. No. 10/573,297, filed Apr. 9, 2007, which is the U.S. National Phase entry under 35 U.S.C. §371 of International Application No. PCT/JP2004/014438, filed Sep. 24, 2004, which claims the benefit of U.S. Provisional Application Ser. No. 60/505,571 filed Sep. 24, 2003, the contents of which are hereby incorporated by reference in its entirety.

FIELD OF THE INVENTION

The present invention relates to methods of detecting and diagnosing breast cancer as well as methods of treating and preventing breast cancer and breast cancer metastasis.

BACKGROUND OF THE INVENTION

Breast cancer, a genetically heterogeneous disease, is the most common malignancy in women. An estimation of approximately 800000 new cases were reported each year worldwide (Parkin D M, Pisani P, Ferlay J (1999). CA Cancer J Clin 49: 33-64). Mastectomy is the first concurrent option for the treatment of this disease. Despite surgical removal of the primary tumors, relapse at local or distant sites may occur due to undetectable micrometastasis (Saphner T, Tommey D C, Gray R (1996). J Clin Oncol, 14, 2738-2749.) at the time of diagnosis. Cytotoxic agents are usually administered as adjuvant therapy after surgery aiming to kill those residual or pre malignant cells.

Treatment with conventional chemotherapeutic agents is often empirical and is mostly based on histological tumor parameters, and in the absence of specific mechanistic understanding. Target-directed drugs are therefore becoming the bedrock treatment for breast cancer. Tamoxifen and aromatase inhibitors, two representatives of its kind, have been proved to have great responses used as adjuvant or chemoprevention in patients with metastasized breast cancer (Fisher B, Costantino J P, Wickerham D L, Redmond C K, Kavanah M, Cronin W M, Vogel V, Robidoux A, Dimitrov N, Atkins J, Daly M, Wieand S, Tan-Chiu E, Ford L, Wolmark N (1998). J Natl Cancer Inst, 90, 1371-1388; Cuzick J (2002). Lancet 360, 817-824). However the drawback is that only patients expressed estrogen receptors are sensitive to these drugs. A recent concerns were even raised regarding their side effects particularly lay on the possibility of causing endometrial cancer for long term tamoxifen treatment as well as deleterious effect of bone fracture in the postmenopausal women in aromatase prescribed patients (Coleman R E (2004). Oncology. 18 (5 Suppl 3), 16-20). Owing to the emergence of side effect and drug resistance, it is obviously necessarily to search novel molecular targets for selective smart drugs on the basis of characterized mechanisms of action.

Breast cancer is a complex disease associated with numerous genetic changes. Little is known about whether these abnormalities are the cause of breast tumorigenesis, although it has been reported that they occur by a multistep process which can be broadly equated to transformation of normal cells, via the steps of atypical ductal hyperplasia, ductal carcinoma in situ (DCIS) and invasive ductal carcinoma (IDC). There is evidence that only a portion of premalignant lesions are committed to progression to invasive cancer while the other lesions undergo spontaneous regression. This explanation of molecular participation, which leads to development of primary breast cancer, its progression, and its formation of metastases, is the main focus for new strategies targeted at prevention and treatment.

Gene-expression profiles generated by cDNA microarray analysis can provide considerably more detail about the nature of individual cancers than traditional histopathological methods are able to supply. The promise of such information lies in its potential for improving clinical strategies for treating neoplastic diseases and developing novel drugs (Petricoin, E. F., 3rd, Hackett, J. L., Lesko, L. J., Puri, R. K., Gutman, S. I., Chumakov, K., Woodcock, J., Feigal, D. W., Jr., Zoon, K. C., and Sistare, F. D. Medical applications of microarray technologies: a regulatory science perspective. Nat Genet, 32 *Suppl:* 474-479, 2002). To this aim, the present inventors have analyzed the expression profiles of tumor or tumors from various tissues by cDNA microarrays (Okabe, H. et al., Genome-wide analysis of gene expression in human hepatocellular carcinomas using cDNA microarray: identification of genes involved in viral carcinogenesis and tumor progression. Cancer Res, 61: 2129-2137, 2001; Hasegawa, S. et al., Genome-wide analysis of gene expression in intestinal-type gastric cancers using a complementary DNA microarray representing 23,040 genes. Cancer Res, 62: 7012-7017, 2002; Kaneta, Y. et al., and Ohno, R. Prediction of Sensitivity to ST1571 among Chronic Myeloid Leukemia Patients by Genome-wide cDNA Microarray Analysis. Jpn J Cancer Res, 93: 849-856, 2002; Kaneta, Y. et al., Genome-wide analysis of gene-expression profiles in chronic myeloid leukemia cells using a cDNA microarray. Int J Oncol, 23: 681-691, 2003; Kitahara, O. et al., Alterations of gene expression during colorectal carcinogenesis revealed by cDNA microarrays after laser-capture microdissection of tumor tissues and normal epithelia. Cancer Res, 61: 3544-3549, 2001; Lin, Y. et al. Molecular diagnosis of colorectal tumors by expression profiles of 50 genes expressed differentially in adenomas and carcinomas. Oncogene, 21: 4120-4128, 2002; Nagayama, S. et al., Genome-wide analysis of gene expression in synovial sarcomas using a cDNA microarray. Cancer Res, 62: 5859-5866, 2002; Okutsu, J. et al., Prediction of chemosensitivity for patients with acute myeloid leukemia, according to expression levels of 28 genes selected by genome-wide complementary DNA microarray analysis. Mol Cancer Ther, 1: 1035-1042, 2002; Kikuchi, T. et al., Expression profiles of non-small cell lung cancers on cDNA microarrays: identification of genes for prediction of lymph-node metastasis and sensitivity to anti-cancer drugs. Oncogene, 22: 2192-2205, 2003).

Recent examination into the expression levels of thousands of genes through the use of cDNA microarrays have resulted in the discovery of distinct patterns in different types of breast cancer (Sgroi, D. C. et al., In vivo gene expression profile analysis of human breast cancer progression. Cancer Res, 59: 5656-5661, 1999; Sorlie, T. et al., Gene expression patterns of breast carcinomas distinguish tumor subclasses with clinical implications. Proc Natl Acad Sci USA, 98: 10869-10874, 2001; Kauraniemi, P. et al., New amplified and highly expressed genes discovered in the ERBB2 amplicon in breast cancer by cDNA microarrays. Cancer Res, 61: 8235-8240, 2001; Gruvberger, S. et al., S. Estrogen receptor status in breast cancer is associated with remarkably distinct gene expression patterns. Cancer Res, 61: 5979-5984, 2001; Dressman, M. et al., Gene expression profiling detects gene amplification and differentiates tumor types in breast cancer. Cancer Res, 63: 2194-2199, 2003).

Studies into gene-expression profiles in breast cancers have resulted in the identification of genes that may serve as candidates for diagnostic markers or prognosis profiles. However, these data, derived primarily from tumor masses, cannot adequately reflect expressional changes during breast carcinogenesis, because breast cancer cells exist as a solid mass with a highly inflammatory reaction and containing various cellular components. Therefore, previously published microarray data is likely to reflect heterogenous profiles.

Studies designed to reveal mechanisms of carcinogenesis have already facilitated the identification of molecular targets for certain anti-tumor agents. For example, inhibitors of farnesyltransferase (FTIs) which were originally developed to inhibit the growth-signaling pathway related to Ras, whose activation depends on post-translational farnesylation, have been shown to be effective in treating Ras-dependent tumors in animal models (He et al., Cell 99:335-45 (1999)). Similarly, clinical trials on humans using a combination of anticancer drugs and the anti-HER2 monoclonal antibody, trastuzumab, with the aim of antagonizing the proto-oncogene receptor HER2/neu have achieved improved clinical response and overall survival of breast-cancer patients (Lin et al., Cancer Res 61:6345-9 (2001)). Finally, a tyrosine kinase inhibitor, STI-571, which selectively inactivates bcr-abl fusion proteins, has been developed to treat chronic myelogenous leukemias wherein constitutive activation of bcr-abl tyrosine kinase plays a crucial role in the transformation of leukocytes. Agents of these kinds are designed to suppress oncogenic activity of specific gene products (Fujita et al., Cancer Res 61:7722-6 (2001)). Accordingly, it is apparent that gene products commonly up-regulated in cancerous cells may serve as potential targets for developing novel anti-cancer agents.

It has been further demonstrated that CD8+ cytotoxic T lymphocytes (CTLs) recognize epitope peptides derived from tumor-associated antigens (TAAs) presented on the MHC Class I molecule, and lyse tumor cells. Since the discovery of the MAGE family as the first example of TAAs, many other TAAs have been discovered using immunological approaches (Boon, Int J Cancer 54: 177-80 (1993); Boon and van der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994)). Some of the newly discovered TAAs are currently undergoing clinical development as targets of immunotherapy. TAAs discovered so far include MAGE (van der Bruggen et al., Science 254: 1643-7 (1991)), gp100 (Kawakami et al., J Exp Med 180: 347-52 (1994)), SART (Shichijo et al., J Exp Med 187: 277-88 (1998)), and NY-ESO-1 (Chen et al., Proc Natl Acad Sci USA 94: 1914-8 (1997)). On the other hand, gene products demonstrated to be specifically over-expressed in tumor cells have been shown to be recognized as targets inducing cellular immune responses. Such gene products include p53 (Umano et al., Brit J Cancer 84: 1052-7 (2001)), HER2/neu (Tanaka et al., Brit J Cancer 84: 94-9 (2001)), CEA (Nukaya et al., Int J Cancer 80: 92-7 (1999)), and so on.

In spite of significant progress in basic and clinical research concerning TAAs (Rosenberg et al., Nature Med 4: 321-7 (1998); Mukherji et al., Proc Natl Acad Sci USA 92: 8078-82 (1995); Hu et al., Cancer Res 56: 2479-83 (1996)), only limited number of candidate TAAs for the treatment of adenocarcinomas, including colorectal cancer, are currently available. TAAs abundantly expressed in cancer cells yet whose expression is restricted to cancer cells would be promising candidates as immunotherapeutic targets. Further, identification of new TAAs inducing potent and specific antitumor immune responses is expected to encourage clinical use of peptide vaccination strategies for various types of cancer (Boon and can der Bruggen, J Exp Med 183: 725-9 (1996); van der Bruggen et al., Science 254: 1643-7 (1991); Brichard et al., J Exp Med 178: 489-95 (1993); Kawakami et al., J Exp Med 180: 347-52 (1994); Shichijo et al., J Exp Med 187: 277-88 (1998); Chen et al., Proc Natl Acad Sci USA 94: 1914-8 (1997); Harris, J Natl Cancer Inst 88: 1442-5 (1996); Butterfield et al., Cancer Res 59: 3134-42 (1999); Vissers et al., Cancer Res 59: 5554-9 (1999); van der Burg et al., J Immunol 156: 3308-14 (1996); Tanaka et al., Cancer Res 57: 4465-8 (1997); Fujie et al., Int J Cancer 80: 169-72 (1999); Kikuchi et al., Int J Cancer 81: 459-66 (1999); Oiso et al., Int J Cancer 81: 387-94 (1999)).

It has been repeatedly reported that peptide-stimulated peripheral blood mononuclear cells (PBMCs) from certain healthy donors produce significant levels of IFN-γ in response to the peptide, but rarely exert cytotoxicity against tumor cells in an HLA-A24 or -A0201 restricted manner in $^{51}$Cr-release assays (Kawano et al., Cancer Res 60: 3550-8 (2000); Nishizaka et al., Cancer Res 60: 4830-7 (2000); Tamura et al., Jpn J Cancer Res 92: 762-7 (2001)). However, both of HLA-A24 and HLA-A0201 are popular HLA alleles in the Japanese, as well as the Caucasian populations (Date et al., Tissue Antigens 47: 93-101 (1996); Kondo et al., J Immunol 155: 4307-12 (1995); Kubo et al., J Immunol 152: 3913-24 (1994); Imanishi et al., Proceeding of the eleventh International Histocompatibility Workshop and Conference Oxford University Press, Oxford, 1065 (1992); Williams et al., Tissue Antigen 49: 129 (1997)). Thus, antigenic peptides of carcinomas presented by these HLAs may be especially useful for the treatment of carcinomas among Japanese and Caucasians. Further, it is known that the induction of low-affinity CTL in vitro usually results from the use of peptide at a high concentration, generating a high level of specific peptide/MHC complexes on antigen presenting cells (APCs), which will effectively activate these CTL (Alexander-Miller et al., Proc Natl Acad Sci USA 93: 4102-7 (1996)).

Accordingly, in an effort to understand the carcinogenic mechanisms associated with cancer and identify potential targets for developing novel anti-cancer agents, the present inventors performed large scale genome-wide analyses of gene expression profiles found in purified populations of breast cancer cells, including 12 ductal carcinomas in situ (DCIS) and 69 invasive ductal carcinomas (IDC), using a cDNA microarray representing 23,040 genes.

SUMMARY OF THE INVENTION

The present invention is based on the discovery of a pattern of gene expression that correlates with breast cancer (BRC). Genes that are differentially expressed in breast cancer are collectively referred to herein as "BRC nucleic acids" or "BRC polynucleotides" and the corresponding encoded polypeptides are referred to as "BRC polypeptides" or "BRC proteins."

Accordingly, the present invention provides a method of diagnosing or determining a predisposition to breast cancer in a subject by determining an expression level of a BRC-associated gene in a patient-derived biological sample, such as tissue sample. The term "BRC-associated gene" refers to a gene that is characterized by an expression level which differs in a BRC cell as compared to a normal cell. A normal cell is one obtained from breast tissue. In the context of the present invention, a BRC-associated gene is a gene listed in tables 3-8 (i.e., genes of BRC Nos. 123-512). An alteration, e.g., an increase or decrease in the level of expression of a gene as compared to a normal control level of the gene, indicates that the subject suffers from or is at risk of developing BRC.

In the context of the present invention, the phrase "control level" refers to a protein expression level detected in a control sample and includes both a normal control level and an breast cancer control level. A control level can be a single expression pattern derived from a single reference population or from a plurality of expression patterns. For example, the control level can be a database of expression patterns from previously tested cells. A "normal control level" refers to a level of gene expression detected in a normal, healthy individual or in a population of individuals known not to be suffering from breast cancer. A normal individual is one with no clinical symptoms of breast cancer. On the other hand, a "BRC control level" refers to an expression profile of BRC-associated genes found in a population suffering from BRC.

An increase in the expression level of one or more BRC-associated genes listed in tables 3, 5, and 7 (i.e., genes of BRC Nos. 123-175, 374-398, and 448-471) detected in a test sample as compared to a normal control level indicates that the subject (from which the sample was obtained) suffers from or is at risk of developing BRC. In contrast, a decrease in the expression level of one or more BRC-associated genes listed in tables 4, 6, and 8 (i.e., genes of BRC Nos. 176-373, 399-447, and 472-512) detected in a test sample compared to a normal control level indicates said subject suffers from or is at risk of developing BRC.

Alternatively, expression of a panel of BRC-associated genes in a sample can be compared to a BRC control level of the same panel of genes. A similarity between a sample expression and BRC control expression indicates that the subject (from which the sample was obtained) suffers from or is at risk of developing BRC.

According to the present invention, gene expression level is deemed "altered" when gene expression is increased or decreased 10%, 25%, 50% as compared to the control level. Alternatively, an expression level is deemed "increased" or "decreased" when gene expression is increased or decreased by at least 0.1, at least 0.2, at least 1, at least 2, at least 5, or at least 10 or more fold as compared to a control level. Expression is determined by detecting hybridization, e.g., on an array, of a BRC-associated gene probe to a gene transcript of the patient-derived tissue sample.

In the context of the present invention, the patient-derived tissue sample is any tissue obtained from a test subject, e.g., a patient known to or suspected of having BRC. For example, the tissue may contains an epithelial cell. More particularly, the tissue may be an epithelial cell from a breast ductal carcinoma.

The present invention also provides a BRC reference expression profile, comprising a gene expression level of two or more of BRC-associated genes listed in tables 3-8. Alternatively, the BRC reference expression profile may comprise the levels of expression of two or more of BRC-associated genes listed in tables 3, 5, and 7, or BRC-associated genes listed in tables 4, 6, and 8.

The present invention further provides methods of identifying an agent that inhibits or enhances the expression or activity of an BRC-associated gene, e.g. a BRC-associated gene listed in tables 3-8, by contacting a test cell expressing a BRC-associated gene with a test compound and determining the expression level of the BRC-associated gene or the activity of its gene product. The test cell may be an epithelial cell, such as an epithelial cell obtained from a breast carcinoma. A decrease in the expression level of an up-regulated BRC-associated gene or the activity of its gene product as compared to a normal control level or activity of the gene or gene product indicates that the test agent is an inhibitor of the BRC-associated gene and may be used to reduce a symptom of BRC, e.g. the expression of one or more BRC-associated genes listed in tables 3, 5, and 7. Alternatively, an increase in the expression level of a down-regulated BRC-associated gene or the activity of its gene product as compared to a normal control level or activity of the gene or gene product indicates that the test agent is an enhancer of expression or function of the BRC-associated gene and may be used to reduce a symptom of BRC, e.g., the under-expression of one or more BRC-associated genes listed in tables 4, 6, and 8.

The present invention also provides a kit comprising a detection reagent which binds to one or more BRC nucleic acids or BRC polypeptides. Also provided is an array of nucleic acids that binds to one or more BRC nucleic acids.

Therapeutic methods of the present invention include a method of treating or preventing BRC in a subject including the step of administering to the subject an antisense composition. In the context of the present invention, the antisense composition reduces the expression of the specific target gene. For example, the antisense composition may contain a nucleotide which is complementary to a BRC-associated gene sequence selected from the group consisting of the BRC-associated genes listed in Tables 3, 5, and 7. Alternatively, the present method may include the steps of administering to a subject a small interfering RNA (siRNA) composition. In the context of the present invention, the siRNA composition reduces the expression of a BRC nucleic acid selected from the group consisting of the BRC-associated genes listed in tables 3, 5, and 7. In yet another method, the treatment or prevention of BRC in a subject may be carried out by administering to a subject a ribozyme composition. In the context of the present invention, the nucleic acid-specific ribozyme composition reduces the expression of a BRC nucleic acid selected from the group consisting of the BRC-associated genes listed in Tables 3, 5, and 7. Actually, the inhibition effect of the siRNA for BRC-associated genes listed in the tables was confirmed. For example, it has been clearly shown that the siRNA for BRC-456 of Table 7 (GenBank Accession Nos. AF237709 and NM_018492, TOPK; T-LAK cell-originated protein kinase; SEQ ID NOS:48-51) inhibits cell proliferation of breast cancer cells in the examples section. Thus, in the present invention, BRC-associated genes listed in Tables 3, 5, and 7, especially BRC-456, are preferable therapeutic targets of breast cancer. Other therapeutic methods include those in which a subject is administered a compound that increases the expression of one or more of the BRC-associated genes listed in tables 4, 6, and 8 or the activity of a polypeptide encoded by one or more of the BRC-associated genes listed in Tables 4, 6, and 8.

The present invention also includes vaccines and vaccination methods. For example, a method of treating or preventing BRC in a subject may involve administering to the subject a vaccine containing a polypeptide encoded by a nucleic acid selected from the group consisting of BRC-associated genes listed in tables 3, 5, and 7 or an immunologically active fragment of such a polypeptide. In the context of the present invention, an immunologically active fragment is a polypeptide that is shorter in length than the full-length naturally-occurring protein yet which induces an immune response analogous to that induced by the full-length protein. For example, an immunologically active fragment should be at least 8 residues in length and capable of stimulating an immune cell such as a T cell or a B cell. Immune cell stimulation can be measured by detecting cell proliferation, elaboration of cytokines (e.g., IL-2), or production of an antibody.

Additionally, the present invention provides target molecules for treating or preventing metastasis of breast cancer. According to the present invention, genes listed in table 11

(i.e., genes of BRC Nos. 719-752) were identified as genes having unique altered expression patterns in breast cancer cells with lymph-node metastasis. Thus, metastasis of breast cancer can be treated or prevented via the suppression of the expression or activity of up-regulated genes or their gene products selected from the group consisting of VAMP3, MGC 11257, GSPT1, DNM2, CFL1, CLNS1A, SENP2, NDUFS3, NOP5/NOP58, PSMD13, SUOX, HRB2, LOC154467, THTPA, ZRF1, LOC51255, DEAF1, NEU1, UGCGL1, BRAF, TUFM, FLJ10726, DNAJB1, AP4S1, and MRPL40. Alternatively, metastasis of breast cancer can be treated or prevented by enhancing the expression or activity of UBA52, GenBank Acc# AA634090, CEACAM3, C21orf97, KIAA1040, EEF1D, FUS, GenBank Acc# AW965200, and KIAA0475 in cancerous cells.

The present invention also provides methods for predicting metastasis of breast cancer. Specifically, the present method comprises the step of measuring the expression level of marker genes selected from the group consisting of genes listed in table 11. These marker genes are identified herein as genes having unique altered expression patterns in breast cancer cells of patients with lymph node metastasis. Therefore, metastasis of the breast cancer in a subject can be predicted by determining whether the expression level detected in a sample derived from the subject is closer to the mean expression level of lymph node metastasis positive cases or negative cases in reference samples.

Among the up-regulated genes, we identified A7870, designed T-LAK cell-originated protein kinase (TOPK), that was more than three-fold overexpressed in 30 of 39 (77%) breast cancer cases which were able to obtain expression data, especially in 29 of 36 (81%) cases with invasive ductal carcinoma specimens. Subsequent semi-quantitative RT-PCR also confirmed that A7870 were up-regulated in 7 of 12 clinical breast cancer samples and 17 of 20 breast cancer cell lines, compared to normal human organs including breast ductal cells or normal breast. Northern blot analyses revealed that the A7870 transcript was expressed only in breast cancer cell lines and normal human testis and thymus. Immunocytochemical staining with TOPK antibody shows that subcellular localization of endogenous A7870 was observed in the cytoplasmic and around the nuclear membrane in breast cancer cell lines, T47D, BT20 and HBC5. Treatment of breast cancer cells with small interfering RNAs (siRNAs) effectively inhibited expression of A7870 and suppressed cell/tumor growth of breast cancer cell lines, T47D and BT-20, suggesting that this gene plays a key role in cell growth proliferation. These findings suggest that overexpression of A7870 might be involved in breast tumorigenesis, and promising strategies for specific treatment for breast cancer patients.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference herein in their entirety. In case of conflict, the present specification, including definitions, will control. In addition, the materials, methods, and examples are illustrative only and not intended to be limiting.

One advantage of the methods described herein is that the disease is identified prior to detection of overt clinical symptoms of breast cancer. Other features and advantages of the invention will be apparent from the following detailed description, and from the claims.

BRIEF DESCRIPTION OF THE DRAWINGS

In FIG. 2(A), each horizontal row represents a breast cancer patient, and each vertical column shows a single gene. An asterisk mark indicates the major historical type, and a sharp mark indicates the minor historical type in the same case. A square indicates a duplicated case (10149a1 and 10149a1T). A black square indicates unchanged expression. ER refers to ER status measured by EIA, LN to lymph-node metastasis status, and ESR1 to expression profiles of ESR1 in this microarray. FIG. 2(B) depicts two-dimensional hierarchical clustering analysis of 89 genes across 16 samples with 2 differentiated lesion microdissected from 8 breast cancer patients. FIG. 2(C) depicts clustering analysis using 25 genes that showed differential expression between well- and poorly-differentiated invasive ductal cancer cells.

FIG. 4(A) depicts a cluster of 251 genes commonly up- or down-regulated in DCIS and IDC. FIG. 4(B) depicts a cluster of 74 genes having elevated or decreased expression in transition from DCIS to IDC. FIG. 4(C) depicts a cluster of 65 genes specifically up- or down-regulated in IDC.

FIG. 10(A) depicts the results of a two-dimensional hierarchical clustering analysis using 34 genes selected by evaluation of classification and leave-one-out test after a random-permutation test for establishing a predictive scoring system. Genes in the upper main branch were preferentially expressed in cases involving lymph node metastasis; those in the lower branch were more highly expressed in lymph node-negative cases. FIG. 10(B) depicts the strength of genes appearing in 7(A) for separating non-metastatic (lymph node-negative) tumors from metastatic (lymph node-positive) tumors. Squares represent node-positive cases; Triangles denote negative cases. The 17 empty squares represents a lymph node-positive test case and the 20 empty triangle represents lymph node-negative test cases that were not used for establishing prediction scores. FIG. 10(C) depicts the correlation between the prediction score for metastasis and clinical information after operation.

DETAILED DESCRIPTION OF THE INVENTION

Figure 1:
FIG. 1 depicts images of premicrodissected (lane A), post-microdissected (lane B), and the microdissected cells (lane C). Microdissection of DCIS, IDC cells and normal breast ductal epithelial cells was performed using Laser microbeam microdissection (LMM). DCIS cells (10326T case), IDC cells (10502T), and normal breast ductal epithelial cell (10341N) from each specimen were microdissected from hematoxylin and eosin stained sections.
Figure 1:
Figure 1:
Figure 1:
Figure 1:
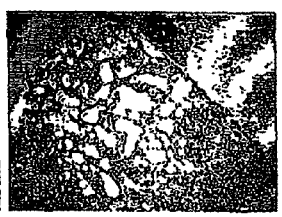
Figure 1:
Figure 1:
Figure 1:
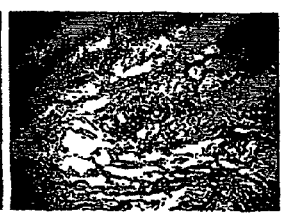
Figure 1:
Figure 1:
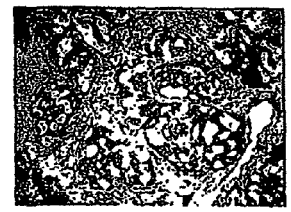
Figure 1:
Figure 1:
Figure 1:
Figure 1:
Figure 1:

The words "a", "an" and "the" as used herein mean "at least one" unless otherwise specifically indicated.

Generally breast cancer cells exist as a solid mass having a highly inflammatory reaction and containing various cellular components. Therefore, previous published microarray data are likely to reflect heterogenous profiles.

With these issues in view, the present inventors prepared purified populations of breast cancer cells and normal breast epithelial duct cells by a method of laser-microbeam microdissection (LMM), and analyzed genome-wide gene-expression profiles of 81 BRCs, including 12 ductal carcinomas in situ (DCIS) and 69 invasive ductal carcinomas (IDC), using a cDNA microarray representing 23,040 genes. These data not only should provide important information about breast carcinogenesis, but should facilitate the identification of candidate genes whose products may serve as diagnostic markers and/or as molecular targets for treatment of patients with breast cancer and providing clinically relevant information.

The present invention is based, in part, on the discovery of changes in expression patterns of multiple nucleic acids between epithelial cells and carcinomas of patients with BRC. The differences in gene expression were identified using a comprehensive cDNA microarray system.

The gene-expression profiles of cancer cells from 81 BRCs, including 12 DCISs and 69 IDCs, were analyzed using a cDNA microarray representing 23,040 genes coupled with laser microdissection. By comparing expression patterns between cancer cells from patients diagnosed with BRC and normal ductal epithelial cells purely selected with Laser Microdissection, 102 genes (shown in tables 3, 5 and 7) were identified as commonly up-regulated in BRC cells and among them 100 genes were selected as BRC-associated genes of the present invention. Similarly, 288 genes (shown in tables 4, 6 and 8) were also identified as being commonly down-regulated in BRC cells. In addition, selection was made of candidate molecular markers having the potential to detect cancer-related proteins in serum or sputum of patients, and some potential targets for development of signal-suppressing strategies in human BRC were discovered. Among them, tables 3 and 4 provide a list of genes whose expression is altered between BRC, including DCIS and IDC, and normal tissue. Genes commonly up- or down-regulated in DCIS and IDC are shown in table 3 and table 4, respectively. Genes having elevated or decreased expression in transition from DCIS to IDC are listed in tables 5 and 6, respectively. Furthermore, genes commonly up- or down-regulated in IDC as compared with normal tissue are listed in tables 7 and 8, respectively.

The differentially expressed genes identified herein find diagnostic utility as markers of BRC and as BRC gene targets, the expression of which may be altered to treat or alleviate a symptom of BRC. Alternatively, the genes differentially expressed between DCIS and IDC identified herein find diagnostic utility as markers for distinguishing IDC from DCIS and as BRC gene targets, the expression of which may be altered to treat or alleviate a symptom of IDC.

The genes whose expression level is modulated (i.e., increased or decreased) in BRC patients are summarized in tables 3-8 and are collectively referred to herein as "BRC-associated genes", "BRC nucleic acids" or "BRC polynucleotides" and the corresponding encoded polypeptides are referred to as "BRC polypeptides" or "BRC proteins." Unless indicated otherwise, "BRC" refers to any of the sequences disclosed herein. (e.g., BRC-associated genes listed in tables 3-8). Genes that have been previously described are presented along with a database accession number.

By measuring expression of the various genes in a sample of cells, BRC can be diagnosed. Similarly, measuring the expression of these genes in response to various agents can identify agents for treating BRC.

The present invention involves determining (e.g., measuring) the expression of at least one, and up to all the BRC-associated genes listed in tables 3-8. Using sequence information provided by the GenBank™ database entries for known sequences, the BRC-associated genes can be detected and measured using techniques well known to one of ordinary skill in the art. For example, sequences within the sequence database entries corresponding to BRC-associated genes, can be used to construct probes for detecting RNA sequences corresponding to BRC-associated genes in, e.g., Northern blot hybridization analyses. Probes typically include at least 10, at least 20, at least 50, at least 100, or at least 200 nucleotides of a reference sequence. As another example, the sequences can be used to construct primers for specifically amplifying the BRC nucleic acid in, e.g., amplification-based detection methods, such as reverse-transcription based polymerase chain reaction.

Expression level of one or more of BRC-associated genes in a test cell population, e.g., a patient-derived tissues sample, is then compared to the expression level(s) of the same gene(s) in a reference population. The reference cell population includes one or more cells for which the compared parameter is known, i.e., breast ductal carcinoma cells (e.g., BRC cells) or normal breast ductal epithelial cells (e.g., non-BRC cells).

Whether or not a pattern of gene expression in a test cell population as compared to a reference cell population indicates BRC or a predisposition thereto depends upon the composition of the reference cell population. For example, if the reference cell population is composed of non-BRC cells, a similarity in gene expression pattern between the test cell population and the reference cell population indicates the test cell population is non-BRC. Conversely, if the reference cell population is made up of BRC cells, a similarity in gene expression profile between the test cell population and the reference cell population indicates that the test cell population includes BRC cells.

A level of expression of a BRC marker gene in a test cell population is considered "altered" if it varies from the expression level of the corresponding BRC marker gene in a reference cell population by more than 1.1, more than 1.5, more than 2.0, more than 5.0, more than 10.0 or more fold.

Differential gene expression between a test cell population and a reference cell population can be normalized to a control nucleic acid, e.g. a housekeeping gene. For example, a control nucleic acid is one which is known not to differ depending on the cancerous or non-cancerous state of the cell. The expression level of a control nucleic acid can be used to normalize signal levels in the test and reference populations. Exemplary control genes include, but are not limited to, e.g., β-actin, glyceraldehyde 3-phosphate dehydrogenase and ribosomal protein P1.

The test cell population can be compared to multiple reference cell populations. Each of the multiple reference populations may differ in the known parameter. Thus, a test cell population may be compared to a first reference cell population known to contain, e.g., BRC cells, as well as a second reference population known to contain, e.g., non-BRC cells (normal cells). The test cell may be included in a tissue type or cell sample from a subject known to contain, or suspected of containing, BRC cells.

The test cell is obtained from a bodily tissue or a bodily fluid, e.g., biological fluid (such as blood or sputum, for example). For example, the test cell may be purified from breast tissue. Preferably, the test cell population comprises an epithelial cell. The epithelial cell is preferably from a tissue known to be or suspected to be a breast ductal carcinoma.

Cells in the reference cell population should be derived from a tissue type similar to that of the test cell. Optionally, the reference cell population is a cell line, e.g. a BRC cell line (i.e., a positive control) or a normal non-BRC cell line (i.e., a negative control). Alternatively, the control cell population may be derived from a database of molecular information derived from cells for which the assayed parameter or condition is known.

The subject is preferably a mammal. Exemplary mammals include, but are not limited to, e.g., a human, non-human primate, mouse, rat, dog, cat, horse, or cow.

Expression of the genes disclosed herein can be determined at the protein or nucleic acid level, using methods known in the art. For example, Northern hybridization analysis, using probes which specifically recognize one or more of these nucleic acid sequences can be used to determine gene expression. Alternatively, gene expression may be measured using reverse-transcription-based PCR assays, e.g., using primers specific for the differentially expressed gene sequences. Expression may also be determined at the protein level, i.e., by measuring the level of a polypeptides encoded by a gene described herein, or the biological activity thereof. Such methods are well known in the art and include, but are not limited to, e.g., immunoassays that utilize antibodies to proteins encoded by the genes. The biological activities of the proteins encoded by the genes are generally well known.

Diagnosing Breast Cancer:

In the context of the present invention, BRC is diagnosed by measuring the expression level of one or more BRC nucleic acids from a test population of cells, (i.e., a patient-derived biological sample). Preferably, the test cell population contains an epithelial cell, e.g., a cell obtained from breast tissue. Gene expression can also be measured from blood or other bodily fluids such as urine. Other biological samples can be used for measuring protein levels. For example, the protein level in blood or serum derived from a subject to be diagnosed can be measured by immunoassay or other conventional biological assay.

Expression of one or more BRC-associated genes, e.g., genes listed in tables 3-8, is determined in the test cell or biological sample and compared to the normal control expression level associated with the one or more BRC-associated gene(s) assayed. A normal control level is an expression profile of a BRC-associated gene typically found in a population known not to be suffering from BRC. An alteration (e.g., an increase or decrease) in the level of expression in the patient-derived tissue sample of one or more BRC-associated gene indicates that the subject is suffering from or is at risk of developing BRC. For example, an increase in the expression of one or more up-regulated BRC-associated genes listed in tables 3, 5, and 7 in the test population as compared to the normal control level indicates that the subject is suffering from or is at risk of developing BRC. Conversely, a decrease in expression of one or more down-regulated BRC-associated genes listed in tables 4, 6, and 8 in the test population as compared to the normal control level indicates that the subject is suffering from or is at risk of developing BRC.

Alteration of one or more of the BRC-associated genes in the test population as compared to the normal control level indicates that the subject suffers from or is at risk of developing BRC. For example, alteration of at least 1%, at least 5%, at least 25%, at least 50%, at least 60%, at least 80%, at least 90% or more of the panel of BRC-associated genes (genes listed in tables 3-8) indicates that the subject suffers from or is at risk of developing BRC.

Identifying Histopathological Differentiation of BRC:

The present invention provides a method for identifying histopathological differentiation of BRC in a subject, the method comprising the steps of:

(a) detecting an expression level of one or more marker genes in a tissue sample collected from the subject being tested, wherein the one or more marker genes are selected from the group consisting of genes listed in tables 1 and 10; and (b) comparing the detected expression level of the one or more marker genes to an expression level associated with a well-differentiated case and poorly-differentiated case;

(c) such that when the detected expression level of one or more marker genes is similar to that of the well-differentiated case, the tissue sample is determined to be well-differentiated and when the detected expression level of one or marker genes is similar to that of the poorly-differentiated case, the tissue sample is determined to be poorly-differentiated.

In the present invention, marker gene(s) for identifying histopathological differentiation of BRC may be at least one gene selected from the group consisting of 231 genes shown in Tables 1 and 10. The nucleotide sequences of the genes and amino acid sequences encoded thereby are known in the art. See Tables 1 and 10 for the Accession Numbers of the genes.

Identifying Agents that Inhibit or Enhance BRC-associated Gene Expression:

An agent that inhibits the expression of a BRC-associated gene or the activity of its gene product can be identified by contacting a test cell population expressing a BRC-associated up-regulated gene with a test agent and then determining the expression level of the BRC-associated gene or the activity of its gene product. A decrease in the level of expression of the BRC-associated gene or in the level of activity of its gene product in the presence of the agent as compared to the expression or activity level in the absence of the test agent indicates that the agent is an inhibitor of a BRC-associated up-regulated gene and useful in inhibiting BRC.

Alternatively, an agent that enhances the expression of a BRC-associated down-regulated gene or the activity of its gene product can be identified by contacting a test cell population expressing a BRC-associated gene with a test agent and then determining the expression level or activity of the BRC-associated down-regulated gene. An increase in the level of expression of the BRC-associated gene or in the level of activity of its gene product as compared to the expression or activity level in the absence of the test agent indicates that the test agent augments expression of the BRC-associated down-regulated gene or the activity of its gene product.

The test cell population may be any cell expressing the BRC-associated genes. For example, the test cell population may contain an epithelial cell, such as a cell derived from breast tissue. Furthermore, the test cell may be an immortalized cell line derived from an carcinoma cell. Alternatively, the test cell may be a cell which has been transfected with a BRC-associated gene or which has been transfected with a regulatory sequence (e.g. promoter sequence) from a BRC-associated gene operably linked to a reporter gene.

Assessing Efficacy of Treatment of BRC in a Subject:

The differentially expressed BRC-associated genes identified herein also allow for the course of treatment of BRC to be monitored. In this method, a test cell population is provided from a subject undergoing treatment for BRC. If desired, test cell populations are obtained from the subject at various time points, before, during, and/or after treatment. Expression of one or more of the BRC-associated genes in the cell population is then determined and compared to a reference cell population which includes cells whose BRC state is known. In the context of the present invention, the reference cells should have not been exposed to the treatment of interest.

If the reference cell population contains no BRC cells, a similarity in the expression of a BRC-associated gene in the test cell population and the reference cell population indicates that the treatment of interest is efficacious. However, a difference in the expression of a BRC-associated gene in the test population and a normal control reference cell population indicates a less favorable clinical outcome or prognosis. Similarly, if the reference cell population contains BRC cells, a difference between the expression of a BRC-associated gene in the test cell population and the reference cell population indicates that the treatment of interest is efficacious, while a similarity in the expression of a BRC-associated gene in the test population and a cancer control reference cell population indicates a less favorable clinical outcome or prognosis.

Additionally, the expression level of one or more BRC-associated genes determined in a subject-derived biological sample obtained after treatment (i.e., post-treatment levels) can be compared to the expression level of the one or more BRC-associated genes determined in a subject-derived biological sample obtained prior to treatment onset (i.e., pre-treatment levels). If the BRC-associated gene is an up-regulated gene, a decrease in the expression level in a post-treatment sample indicates that the treatment of interest is efficacious while an increase or maintenance in the expression level in the post-treatment sample indicates a less favorable clinical outcome or prognosis. Conversely, if the BRC-associated gene is an down-regulated gene, an increase in the expression level in a post-treatment sample may indicate that the treatment of interest is efficacious while an decrease or maintenance in the expression level in the post-treatment sample indicates a less favorable clinical outcome or prognosis.

As used herein, the term "efficacious" indicates that the treatment leads to a reduction in the expression of a pathologically up-regulated gene, an increase in the expression of a pathologically down-regulated gene or a decrease in size, prevalence, or metastatic potential of breast ductal carcinoma in a subject. When a treatment of interest is applied prophylactically, the term "efficacious" means that the treatment retards or prevents a breast tumor from forming or retards, prevents, or alleviates a symptom of clinical BRC. Assessment of breast tumors can be made using standard clinical protocols.

In addition, efficaciousness can be determined in association with any known method for diagnosing or treating BRC. BRC can be diagnosed, for example, by identifying symptomatic anomalies, e.g., weight loss, abdominal pain, back pain, anorexia, nausea, vomiting and generalized malaise, weakness, and jaundice.

Selecting a Therapeutic Agent for Treating BRC that is Appropriate for a Particular Individual:

Differences in the genetic makeup of individuals can result in differences in their relative abilities to metabolize various drugs. An agent that is metabolized in a subject to act as an anti-BRC agent can manifest itself by inducing a change in a gene expression pattern in the subject's cells from that characteristic of a cancerous state to a gene expression pattern characteristic of a non-cancerous state. Accordingly, the differentially expressed BRC-associated genes disclosed herein allow for a putative therapeutic or prophylactic inhibitor of BRC to be tested in a test cell population from a selected subject in order to determine if the agent is a suitable inhibitor of BRC in the subject.

To identify an inhibitor of BRC that is appropriate for a specific subject, a test cell population from the subject is exposed to a therapeutic agent, and the expression of one or more of BRC-associated genes listed in table 3-8 is determined.

In the context of the method of the present invention, the test cell population contains a BRC cell expressing a BRC-associated gene. Preferably, the test cell is an epithelial cell. For example, a test cell population may be incubated in the presence of a candidate agent and the pattern of gene expression of the test cell population may be measured and compared to one or more reference profiles, e.g., a BRC reference expression profile or a non-BRC reference expression profile.

A decrease in expression of one or more of the BRC-associated genes listed in tables 3, 5, and 7 or an increase in expression of one or more of the BRC-associated genes listed in tables 4, 6, and 8 in a test cell population relative to a reference cell population containing BRC indicates that the agent has therapeutic potential.

In the context of the present invention, the test agent can be any compound or composition. Exemplary test agents include, but are not limited to, immunomodulatory agents.

Screening Assays for Identifying Therapeutic Agents:

The differentially expressed BRC-associated genes disclosed herein can also be used to identify candidate therapeutic agents for treating BRC. The method of the present invention involves screening a candidate therapeutic agent to determine if it can convert an expression profile of one or more BRC-associated genes listed in tables 3-8 characteristic of a BRC state to a gene expression pattern characteristic of a non-BRC state.

In the instant method, a cell is exposed to a test agent or a plurality of test agents (sequentially or in combination) and the expression of one or more of the BRC-associated genes listed in tables 3-8 in the cell is measured. The expression profile of the BRC-associated gene(s) assayed in the test population is compared to expression level of the same BRC-associated gene(s) in a reference cell population that is not exposed to the test agent.

An agent capable of stimulating the expression of an under-expressed gene or suppressing the expression of an over-expressed genes has potential clinical benefit. Such agents may be further tested for the ability to prevent breast ductal carcinomal growth in animals or test subjects.

In a further embodiment, the present invention provides methods for screening candidate agents which act on the potential targets in the treatment of BRC. As discussed in detail above, by controlling the expression levels of marker genes or the activities of their gene products, one can control the onset and progression of BRC. Thus, candidate agents, which act on the potential targets in the treatment of BRC, can be identified through screening methods that use such expression levels and activities as indices of the cancerous or non-cancerous state. In the context of the present invention, such screening may comprise, for example, the following steps:
   a) contacting a test compound with a polypeptide encoded by a polynucleotide selected from the group consisting of the genes listed in table 3, 4, 5, 6, 7 or 8;
   b) detecting the binding activity between the polypeptide and the test compound; and
   c) selecting the test compound that binds to the polypeptide.

Alternatively, the screening method of the present invention may comprise the following steps:
   a) contacting a candidate compound with a cell expressing one or more marker genes, wherein the one or more marker genes are selected from the group consisting of the genes listed in table 3, 4, 5, 6, 7 or 8; and
   b) selecting the candidate compound that reduces the expression level of one or more marker genes selected from the group consisting of the genes listed in table 3, 5, and 7, or elevates the expression level of one or more marker genes selected from the group consisting of the genes listed in table 4, 6 and 8.

Cells expressing a marker gene include, for example, cell lines established from BRC; such cells can be used for the above screening of the present invention.

Alternatively, the screening method of the present invention may comprise the following steps:
   a) contacting a test compound with a polypeptide encoded by a polynucleotide selected from the group consisting of the genes listed in table 3, 4, 5, 6, 7 or 8;
   b) detecting the biological activity of the polypeptide of step (a); and
   c) selecting a compound that suppresses the biological activity of the polypeptide encoded by the polynucleotide selected from the group consisting of the genes listed in table 3, 5 and 7 as compared to the biological activity detected in the absence of the test compound, or enhances the biological activity of the polypeptide encoded by the polynucleotide selected from the group consisting of the genes listed in table 4, 6 and 8 as compared to the biological activity detected in the absence of the test compound.

A protein for use in the screening method of the present invention can be obtained as a recombinant protein using the nucleotide sequence of the marker gene. Based on the information regarding the marker gene and its encoded protein, one skilled in the art can select any biological activity of the protein as an index for screening and any suitable measurement method to assay for the selected biological activity.

Alternatively, the screening method of the present invention may comprise the following steps:
   a) contacting a candidate compound with a cell into which a vector, comprising the transcriptional regulatory region of one or more marker genes and a reporter gene that is expressed under the control of the transcriptional regulatory region, has been introduced, wherein the one or more marker genes are selected from the group consisting of the genes listed in table 3, 4, 5, 6, 7 or 8;
   b) measuring the expression or activity of said reporter gene; and
   c) selecting the candidate compound that reduces the expression or activity of said reporter gene when said marker gene is an up-regulated marker gene selected from the group consisting of the genes listed in table 3, 5 and 7, or that enhances the expression level of said reporter gene when said marker gene is a down-regulated marker gene selected from the group consisting of the genes listed in table 4, 6 and 8, as compared to a control.

Suitable reporter genes and host cells are well known in the art. A reporter construct suitable for the screening method of the present invention can be prepared by using the transcriptional regulatory region of a marker gene. When the transcriptional regulatory region of the marker gene is known to those skilled in the art, a reporter construct can be prepared by using the previous sequence information. When the transcriptional regulatory region of the marker gene remains unidentified, a nucleotide segment containing the transcriptional regulatory region can be isolated from a genome library based on the nucleotide sequence information of the marker gene.

A compound isolated by the screening serves as a candidate for the development of drugs that inhibit the expression of the marker gene or the activity of the protein encoded by the marker gene and can be applied to the treatment or prevention of breast cancer.

Moreover, compounds in which a part of the structure of the compound inhibiting the activity of proteins encoded by marker genes is converted by addition, deletion and/or replacement are also included as the compounds obtainable by the screening method of the present invention.

When administrating a compound isolated by the method of the present invention as a pharmaceutical for humans and other mammals, such as mice, rats, guinea-pigs, rabbits, cats, dogs, sheep, pigs, cattle, monkeys, baboons, and chimpanzees, the isolated compound can be directly administered or can be formulated into a dosage form using known pharmaceutical preparation methods. For example, according to the need, the drugs can be taken orally, as sugar-coated tablets, capsules, elixirs and microcapsules, or non-orally, in the form of injections of sterile solutions or suspensions with water or any other pharmaceutically acceptable liquid. For example, the compounds can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredient contained in such a preparation makes a suitable dosage within the indicated range acquirable.

Examples of additives that can be admixed into tablets and capsules include, but are not limited to, binders, such as gelatin, corn starch, tragacanth gum and arabic gum; excipients, such as crystalline cellulose; swelling agents, such as corn starch, gelatin and alginic acid; lubricants, such as magnesium stearate; sweeteners, such as sucrose, lactose or saccharin; and flavoring agents, such as peppermint, Gaultheria adenothrix oil and cherry. When the unit-dose form is a capsule, a liquid carrier, such as an oil, can be further included in the above ingredients. Sterile composites for injection can be formulated following normal drug implementations using vehicles, such as distilled water, suitable for injection.

Physiological saline, glucose, and other isotonic liquids, including adjuvants, such as D-sorbitol, D-mannose, D-mannitol, and sodium chloride, can be used as aqueous solutions for injection. These can be used in conjunction with suitable solubilizers, such as alcohol, for example, ethanol; polyalcohols, such as propylene glycol and polyethylene glycol; and non-ionic surfactants, such as Polysorbate 80 (TM) and HCO-50.

Sesame oil or soy-bean oil can be used as an oleaginous liquid, may be used in conjunction with benzyl benzoate or benzyl alcohol as a solubilizer, and may be formulated with a buffer, such as phosphate buffer and sodium acetate buffer; a pain-killer, such as procaine hydrochloride; a stabilizer, such as benzyl alcohol and phenol; and/or an anti-oxidant. A prepared injection may be filled into a suitable ampoule.

Methods well known to those skilled in the art may be used to administer the pharmaceutical composition of the present invention to patients, for example as an intraarterial, intravenous, or percutaneous injection or as an intranasal, transbronchial, intramuscular or oral administration. The dosage and method of administration vary according to the body-weight and age of a patient and the administration method; however, one skilled in the art can routinely select a suitable method of administration. If said compound is encodable by a DNA, the DNA can be inserted into a vector for gene therapy and the vector administered to a patient to perform the therapy. The dosage and method of administration vary according to the body-weight, age, and symptoms of the patient; however, one skilled in the art can suitably select them.

For example, although the dose of a compound that binds to a protein of the present invention and regulates its activity depends on the symptoms, the dose is generally about 0.1 mg to about 100 mg per day, preferably about 1.0 mg to about 50 mg per day and more preferably about 1.0 mg to about 20 mg per day, when administered orally to a normal adult human (weight 60 kg).

When administering the compound parenterally, in the form of an injection to a normal adult human (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. In the case of other animals, the appropriate dosage amount may be routinely calculated by converting to 60 kgs of body-weight.

Screening Assays for Identifying Therapeutic Agents for Metastasis of Breast Cancer:

The present invention provides target molecules for treating or preventing breast cancer metastasis. Screening assays for BRC metastasis of the present invention can be performed according to the method for BRC described above, using marker genes associated with BRC metastasis.

Figures 1, 10:
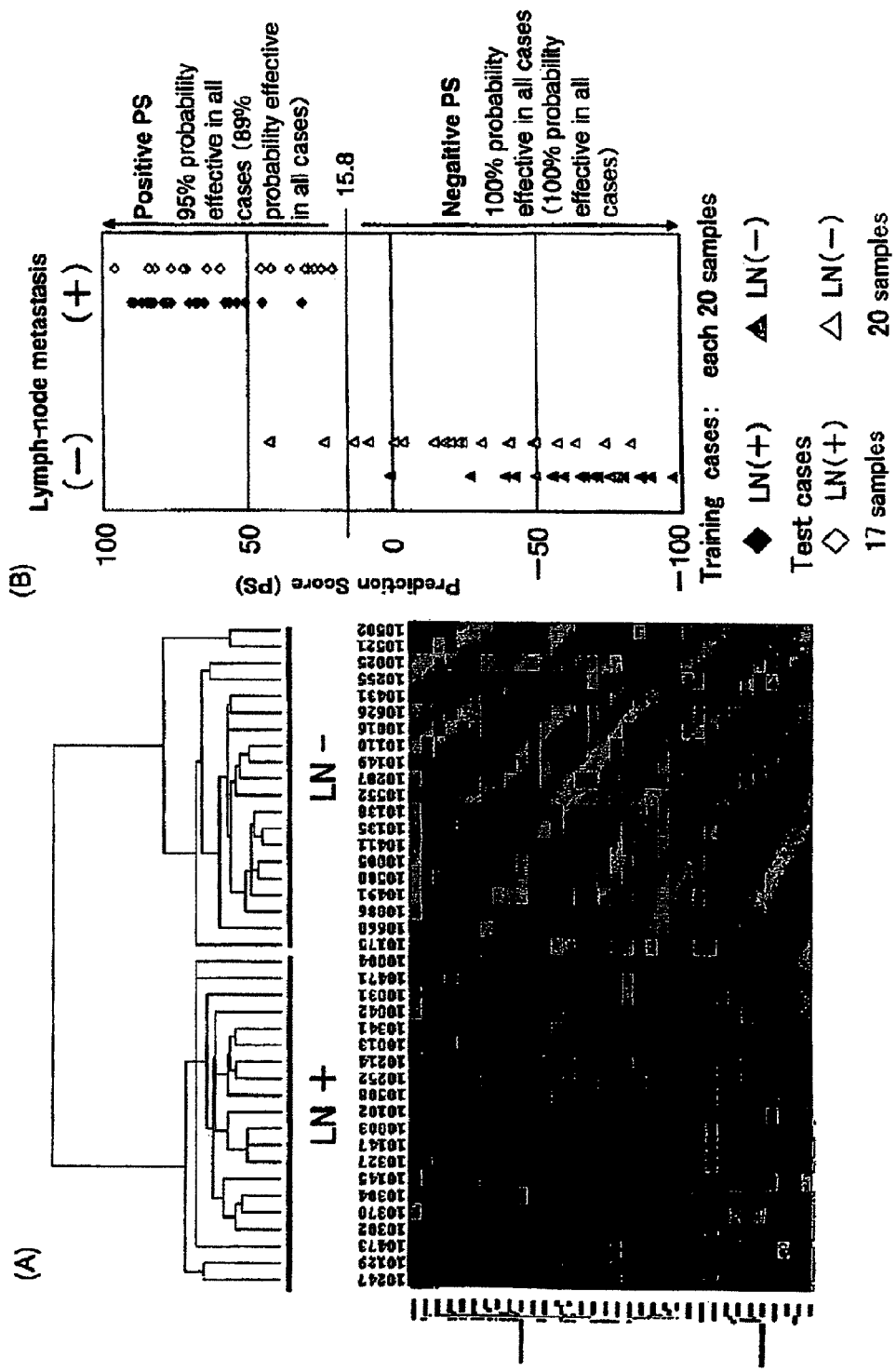

In the present invention, marker genes selected from the group consisting of genes listed in table 11 are useful for the screening. 34 genes shown in the Table are associated with lymph node metastasis. Among the genes, 25 genes (+) were relatively up-regulated and 9 genes (−) were down-regulated in node-positive tumors (Table 11 and FIG. 10). An agent that suppresses the expression of one or more of up-regulated genes or the activity of their gene products obtained by the present invention are useful for treating or preventing BRC with lymph-node metastasis. Alternatively, an agent that enhances the expression of one or more down-regulated genes or the activity of their gene products obtained by the present invention are also useful for treating or preventing BRC with lymph-node metastasis.

In the present invention, the agent regulating an expression level of genes listed in table 11 can be identified by the same manner for identifying agents that inhibit or enhance BRC-associated gene expression. Alternatively, the agent regulating the activity of their gene products can be also identified by the same manner for identifying agents that inhibit or enhance BRC-associated gene product.

Assessing the Prognosis of a Subject with Breast Cancer:

The present invention also provides a method of assessing the prognosis of a subject with BRC including the step of comparing the expression of one or more BRC-associated genes in a test cell population to the expression of the same BRC-associated genes in a reference cell population derived from patients over a spectrum of disease stages. By comparing the gene expression of one or more BRC-associated genes in the test cell population and the reference cell population(s), or by comparing the pattern of gene expression over time in test cell populations derived from the subject, the prognosis of the subject can be assessed.

For example, an increase in the expression of one or more of up-regulated BRC-associated genes, such as those listed in table 3, 5 or 7, as compared to a normal control or a decrease in the expression of one or more of down-regulated BRC-associated genes, such as those listed in table 4, 6 or 8, as compared to a normal control indicates less favorable prognosis. Conversely, a similarity in the expression of one or more of BRC-associated genes listed in tables 3-8 as compared to normal control indicates a more favorable prognosis for the subject. Preferably, the prognosis of a subject can be assessed by comparing the expression profile of the gene selected from the group consisting of genes listed in table 3, 4, 5, 6, 7 and 8. The classification score (CS) may be used for comparing the expression profile.

Kits:

The present invention also includes a BRC-detection reagent, e.g., a nucleic acid that specifically binds to or identifies one or more BRC nucleic acids, such as oligonucleotide sequences which are complementary to a portion of a BRC nucleic acid, or an antibody that bind to one or more proteins encoded by a BRC nucleic acid. The detection reagents may be packaged together in the form of a kit. For example, the detection reagents may be packaged in separate containers, e.g., a nucleic acid or antibody (either bound to a solid matrix or packaged separately with reagents for binding them to the matrix), a control reagent (positive and/or negative), and/or a detectable label. Instructions (e.g., written, tape, VCR, CD-ROM, etc.) for carrying out the assay may also be included in the kit. The assay format of the kit may be a Northern hybridization or a sandwich ELISA, both of which are known in the art.

For example, a BRC detection reagent may be immobilized on a solid matrix, such as a porous strip, to form at least one BRC detection site. The measurement or detection region of the porous strip may include a plurality of sites, each containing a nucleic acid. A test strip may also contain sites for negative and/or positive controls. Alternatively, control sites may be located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of BRC present in the sample. The detection sites may be configured in any suitably detectable shape and are typically in the shape of a bar or dot spanning the width of a test strip.

Alternatively, the kit may contain a nucleic acid substrate array comprising one or more nucleic acids. The nucleic acids on the array specifically identify one or more nucleic acid sequences represented by the BRC-associated genes listed in tables 3-8. The expression of 2, 3, 4, 5, 6, 7, 8, 9, 10, 15, 20, 25, 40 or 50 or more of the nucleic acids represented by the BRC-associated genes listed in tables 3-8 may be identified by virtue of the level of binding to an array test strip or chip. The substrate array can be on, e.g., a solid substrate, such as a "chip" described in U.S. Pat. No. 5,744,305, the contents of which are incorporated by reference herein in its entirety.

Arrays and Pluralities:

The present invention also includes a nucleic acid substrate array comprising one or more nucleic acids. The nucleic acids on the array specifically correspond to one or more nucleic acid sequences represented by the BRC-associated genes listed in tables 3-8. The level of expression of 2, 3, 4, 5, 6, 7, 8, 9, 10, 15, 20, 25, 40 or 50 or more of the nucleic acids represented by the BRC-associated genes listed in tables 3-8 may be identified by detecting nucleic acid binding to the array.

The present invention also includes an isolated plurality (i.e., a mixture of two or more nucleic acids) of nucleic acids. The nucleic acids may be in a liquid phase or a solid phase, e.g., immobilized on a solid support such as a nitrocellulose membrane. The plurality includes one or more of the nucleic acids represented by the BRC-associated genes listed in tables 3-8. In various embodiments, the plurality includes 2, 3, 4, 5, 6, 7, 8, 9, 10, 15, 20, 25, 40 or 50 or more of the nucleic acids represented by the BRC-associated genes listed in tables 3-8.

Methods of Inhibiting Breast Cancer:

The present invention further provides a method for treating or alleviating a symptom of BRC in a subject by decreasing the expression of one or more of the BRC-associated genes listed in tables 3, 5, and 7 (or the activity of its gene product) or increasing the expression of one or more of the BRC-associated genes listed in tables 4, 6, and 8 (or the activity of its gene product). Suitable therapeutic compounds can be administered prophylactically or therapeutically to a subject suffering from or at risk of (or susceptible to) developing BRC. Such subjects can be identified using standard clinical methods or by detecting an aberrant level of expression of one or more of the BRC-associated genes listed in tables 3-8 or aberrant activity of its gene product. In the context of the present invention, suitable therapeutic agents include, for example, inhibitors of cell cycle regulation, cell proliferation, and protein kinase activity.

The therapeutic method of the present invention includes the step of increasing the expression, function, or both of one or more gene products of genes whose expression is decreased ("down-regulated" or "under-expressed" genes) in a BRC cell relative to normal cells of the same tissue type from which the BRC cells are derived. In these methods, the subject is treated with an effective amount of a compound that increases the amount of one or more of the under-expressed (down-regulated) genes in the subject. Administration can be systemic or local. Suitable therapeutic compounds include a polypeptide product of an under-expressed gene, a biologically active fragment thereof, and a nucleic acid encoding an under-expressed gene and having expression control elements permitting expression in the BRC cells; for example, an agent that increases the level of expression of such a gene endogenous to the BRC cells (i.e., which up-regulates the expression of the under-expressed gene or genes). Administration of such compounds counters the effects of aberrantly under-expressed gene or genes in the subject's breast cells and improves the clinical condition of the subject.

Alternatively, the therapeutic method of the present invention may include the step of decreasing the expression, function, or both, of one or more gene products of genes whose expression is aberrantly increased ("up-regulated" or "over-expressed" gene) in breast cells. Expression may be inhibited in any of several ways known in the art. For example, expression can be inhibited by administering to the subject a nucleic acid that inhibits, or antagonizes the expression of the over-expressed gene or genes, e.g., an antisense oligonucleotide or small interfering RNA which disrupts expression of the over-expressed gene or genes.

Antisense Nucleic Acids:

As noted above, antisense nucleic acids corresponding to the nucleotide sequence of the BRC-associated genes listed in tables 3, 5, and 7 can be used to reduce the expression level of the genes. Antisense nucleic acids corresponding to the BRC-associated genes listed in tables 3, 5, and 7 that are up-regulated in breast cancer are useful for the treatment of breast cancer. Specifically, the antisense nucleic acids of the present invention may act by binding to the BRC-associated genes listed in tables 3, 5, and 7, or mRNAs corresponding thereto, thereby inhibiting the transcription or translation of the genes, promoting the degradation of the mRNAs, and/or inhibiting the expression of proteins encoded by the BRC-associated genes listed in tables 3, 5, and 7, thereby, inhibiting the function of the proteins. The term "antisense nucleic acids" as used herein encompasses both nucleotides that are entirely complementary to the target sequence and those having a mismatch of one or more nucleotides, so long as the antisense nucleic acids can specifically hybridize to the target sequences. For example, the antisense nucleic acids of the present invention include polynucleotides that have a homology of at least 70% or higher, preferably at least 80% or higher, more preferably at least 90% or higher, even more preferably at least 95% or higher over a span of at least 15 continuous nucleotides. Algorithms known in the art can be used to determine the homology.

The antisense nucleic acid of the present invention act on cells producing the proteins encoded by BRC-associated marker genes by binding to the DNAs or mRNAs encoding the proteins, inhibiting their transcription or translation, promoting the degradation of the mRNAs, and inhibiting the expression of the proteins, thereby resulting in the inhibition of the protein function.

An antisense nucleic acid of the present invention can be made into an external preparation, such as a liniment or a poultice, by admixing it with a suitable base material which is inactive against the nucleic acid.

Also, as needed, the antisense nucleic acids of the present invention can be formulated into tablets, powders, granules, capsules, liposome capsules, injections, solutions, nosedrops and freeze-drying agents by adding excipients, isotonic agents, solubilizers, stabilizers, preservatives, pain-killers, and such. These can be prepared by following known methods.

The antisense nucleic acids of the present invention can be given to the patient by direct application onto the ailing site or by injection into a blood vessel so that it will reach the site of ailment. An antisense-mounting medium can also be used to increase durability and membrane-permeability. Examples include, but are not limited to, liposomes, poly-L-lysine, lipids, cholesterol, lipofectin or derivatives of these.

The dosage of the antisense nucleic acid derivative of the present invention can be adjusted suitably according to the patient's condition and used in desired amounts. For example, a dose range of 0.1 to 100 mg/kg, preferably 0.1 to 50 mg/kg can be administered.

The antisense nucleic acids of the present invention inhibit the expression of a protein of the present invention and are thereby useful for suppressing the biological activity of the protein of the invention. In addition, expression-inhibitors, comprising antisense nucleic acids of the present invention, are useful in that they can inhibit the biological activity of a protein of the present invention.

The method of the present invention can be used to alter the expression in a cell of an up-regulated BRC-associated gene, e.g., up-regulation resulting from the malignant transformation of the cells. Binding of the siRNA to a transcript corresponding to one of the BRC-associated genes listed in tables 3, 5, and 7 in the target cell results in a reduction in the protein production by the cell. The length of the oligonucleotide is at least 10 nucleotides and may be as long as the naturally-occurring transcript. Preferably, the oligonucleotide is 19-25 nucleotides in length. Most preferably, the oligonucleotide is less than 75, 50, 25 nucleotides in length.

The antisense nucleic acids of present invention include modified oligonucleotides. For example, thioated oligonucleotides may be used to confer nuclease resistance to an oligonucleotide.

Also, an siRNA against a marker gene can be used to reduce the expression level of the marker gene. Herein, term "siRNA" refers to a double stranded RNA molecule which prevents translation of a target mRNA. Standard techniques for introducing siRNA into the cell may be used, including those in which DNA is a template from which RNA is transcribed. In the context of the present invention, the siRNA comprises a sense nucleic acid sequence and an anti-sense nucleic acid sequence against an up-regulated marker gene, such as a BRC-associated gene listed in tables 3, 5, and 7. The siRNA is constructed such that a single transcript has both the sense and complementary antisense sequences from the target gene, e.g., a hairpin.

An siRNA of a BRC-associated gene, such as listed in tables 3, 5, and 7, hybridizes to target mRNA and thereby decreases or inhibits production of the polypeptides encoded by BRC-associated gene listed in tables 3, 5, and 7 by associating with the normally single-stranded mRNA transcript, thereby interfering with translation and thus, expression of the protein. In the context of the present invention, an siRNA is preferably less than 500, 200, 100, 50, or 25 nucleotides in length. More preferably an siRNA is 19-25 nucleotides in length. Exemplary nucleic acid sequence for the production of TOPK siRNA includes the sequences of nucleotides of SEQ ID NOs: 25, 28 and 31 as the target sequence. In order to enhance the inhibition activity of the siRNA, nucleotide "u" can be added to 3' end of the antisense strand of the target sequence. The number of "u"s to be added is at least 2, generally 2 to 10 (SEQ ID NO:32), preferably 2 to 5. The added "u"s form single strand at the 3' end of the antisense strand of the siRNA.

An siRNA of a BRC-associated gene, such as listed in tables 3, 5, and 7, can be directly introduced into the cells in a form that is capable of binding to the mRNA transcripts. Alternatively, a DNA encoding the siRNA may be carried in a vector.

Vectors may be produced, for example, by cloning a BRC-associated gene target sequence into an expression vector having operatively-linked regulatory sequences flanking the sequence in a manner that allows for expression (by transcription of the DNA molecule) of both strands (Lee, N. S., Dohjima, T., Bauer, G., Li, H., Li, M.-J., Ehsani, A., Salvaterra, P., and Rossi, J. (2002) Expression of small interfering RNAs targeted against HIV-1 rev transcripts in human cells. Nature Biotechnology 20:500-505). An RNA molecule that is antisense to mRNA of a BRC-associated gene is transcribed by a first promoter (e.g., a promoter sequence 3' of the cloned DNA) and an RNA molecule that is the sense strand for the mRNA of a BRC-associated gene is transcribed by a second promoter (e.g., a promoter sequence 5' of the cloned DNA). The sense and antisense strands hybridize in vivo to generate siRNA constructs for silencing of the BRC-associated gene. Alternatively, the two constructs can be utilized to create the sense and anti-sense strands of a siRNA construct. Cloned BRC-associated genes can encode a construct having secondary structure, e.g., hairpins, wherein a single transcript has both the sense and complementary antisense sequences from the target gene.

A loop sequence consisting of an arbitrary nucleotide sequence can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence of gene selected from table 3, 5 or 7,

[B] is a ribonucleotide sequence consisting of 3 to 23 nucleotides, and

[A'] is a ribonucleotide sequence consisting of the complementary sequence of [A].

The region [A] hybridizes to [A'], and then a loop consisting of region [B] is formed. The loop sequence may be preferably 3 to 23 nucleotide in length. The loop sequence, for example, can be selected from group consisting of following sequences (at ambion.com/techlib/tb/tb_506.html). Furthermore, loop sequence consisting of 23 nucleotides also provides active siRNA (Jacque, J.-M., Triques, K., and Stevenson, M. (2002) Modulation of HIV-1 replication by RNA interference. Nature 418: 435-438.).

CCC, CCACC or CCACACC: Jacque, J. M, Triques, K., and Stevenson, M (2002) Modulation of HIV-1 replication by RNA interference. Nature, Vol. 418: 435-438.

UUCG: Lee, N. S., Dohjima, T., Bauer, G., Li, H., Li, M.-J., Ehsani, A., Salvaterra, P., and Rossi, J. (2002) Expression of small interfering RNAs targeted against HIV-1 rev transcripts in human cells. Nature Biotechnology 20: 500-505. Fruscoloni, P., Zamboni, M., and Tocchini-Valentini, G. P. (2003) Exonucleolytic degradation of double-stranded RNA by an activity in *Xenopus laevis* germinal vesicles. Proc. Natl. Acad. Sci. USA 100(4): 1639-1644.

UUCAAGAGA: Dykxhoorn, D. M., Novina, C. D., and Sharp, P. A. (2002) Killing the messenger: Short RNAs that silence gene expression. Nature Reviews Molecular Cell Biology 4: 457-467.

Accordingly, the loop sequence can be selected from group consisting of, CCC, UUCG, CCACC, CCACACC, and UUCAAGAGA. Preferable loop sequence is UUCAAGAGA ("ttcaagaga" in DNA). Exemplary hairpin siRNA suitable for use in the context of the present invention include:
for TOPK-siRNA

```
            (for target sequence of SEQ ID NO: 25)
gaacgauauaaagccagcc-[b]-ggcuggcuuuauaucguuc;
(SEQ ID NOS: 33-37

(for target sequence of SEQ ID NO: 28)
cuggaugaaucauaccaga-[b]-ucugguaugauucauccag;
(SEQ ID NOS: 38-42

(for target sequence of SEQ ID NO: 31)
guguggcuugcguaaauaa-[b]-uuauuuacgcaagccacac
(SEQ ID NOS: 43-47
```

The nucleotide sequence of suitable siRNAs can be designed using an siRNA design computer program available from the Ambion website (at ambion.com/techlib/misc/siRNA_finder.html). The computer program selects nucleotide sequences for siRNA synthesis based on the following protocol.

Selection of siRNA Target Sites:
1. Beginning with the AUG start codon of the object transcript, scan downstream for AA dinucleotide sequences. Record the occurrence of each AA and the 3' adjacent 19 nucleotides as potential siRNA target sites. Tuschl, et al. doesn't recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with binding of the siRNA endonuclease complex.
2. Compare the potential target sites to the human genome database and eliminate from consideration any target sequences with significant homology to other coding sequences. The homology search can be performed using BLAST, which can be found on the NCBI server at: ncbi.nlm.nih.gov/BLAST/.
3. Select qualifying target sequences for synthesis. At Ambion, preferably several target sequences can be selected along the length of the gene to evaluate.

The regulatory sequences flanking the BRC-associated gene sequences can be identical or different, such that their expression can be modulated independently, or in a temporal or spatial manner. siRNAs are transcribed intracellularly by cloning the BRC-associated gene templates, respectively, into a vector containing, e.g., a RNA pol III transcription unit from the small nuclear RNA (snRNA) U6 or the human H1 RNA promoter. For introducing the vector into the cell, transfection-enhancing agent can be used. FuGENE (Rochediagnostices), Lipofectamin 2000 (Invitrogen), Oligofectamin (Invitrogen), and Nucleofactor (Wako pure Chemical) are useful as the transfection-enhancing agent.

The antisense oligonucleotide or siRNA of the present invention inhibits the expression of a polypeptide of the present invention and is thereby useful for suppressing the biological activity of a polypeptide of the invention. Also, expression-inhibitors, comprising the antisense oligonucleotide or siRNA of the invention, are useful in the point that they can inhibit the biological activity of the polypeptide of the invention. Therefore, a composition comprising an antisense oligonucleotide or siRNA of the present invention is useful for treating a breast cancer.

Antibodies:
Alternatively, function of one or more gene products of the genes over-expressed in BRC can be inhibited by administering a compound that binds to or otherwise inhibits the function of the gene products. For example, the compound is an antibody which binds to the over-expressed gene product or gene products.

The present invention refers to the use of antibodies, particularly antibodies against a protein encoded by an up-regulated marker gene, or a fragment of such an antibody. As used herein, the term "antibody" refers to an immunoglobulin molecule having a specific structure, that interacts (i.e., binds) only with the antigen that was used for synthesizing the antibody (i.e., the gene product of an up-regulated marker) or with an antigen closely related thereto. Furthermore, an antibody may be a fragment of an antibody or a modified antibody, so long as it binds to one or more of the proteins encoded by the marker genes. For instance, the antibody fragment may be Fab, F(ab')$_2$, Fv, or single chain Fv (scFv), in which Fv fragments from H and L chains are ligated by an appropriate linker (Huston J. S. et al. Proc. Natl. Acad. Sci. U.S.A. 85:5879-5883 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. E. and Walker B. W. Trends Biotechnol. 9:132-137 (1991)).

An antibody may be modified by conjugation with a variety of molecules, such as polyethylene glycol (PEG). The present invention provides such modified antibodies. The modified antibody can be obtained by chemically modifying an antibody. Such modification methods are conventional in the field.

Alternatively, an antibody may comprise a chimeric antibody having a variable region derived from a nonhuman antibody and a constant region derived from a human antibody, or a humanized antibody, comprising a complementarity determining region (CDR) derived from a nonhuman antibody, a frame work region (FR) and a constant region derived from a human antibody. Such antibodies can be prepared by using known technologies.

Cancer therapies directed at specific molecular alterations that occur in cancer cells have been validated through clinical development and regulatory approval of anti-cancer drugs such as trastuzumab (Herceptin) for the treatment of advanced breast cancer, imatinib methylate (Gleevec) for chronic myeloid leukemia, gefitinib (Iressa) for non-small cell lung cancer (NSCLC), and rituximab (anti-CD20 mAb) for B-cell lymphoma and mantle cell lymphoma (Ciardiello F, Tortora G. A novel approach in the treatment of cancer: targeting the epidermal growth factor receptor. Clin Cancer Res. 2001 October; 7(10):2958-70. Review.; Slamon D J, Leyland-Jones B, Shak S, Fuchs H, Paton V, Bajamonde A, Fleming T, Eiermann W, Wolter J, Pegram M, Baselga J, Norton L. Use of chemotherapy plus a monoclonal antibody against HER2 for metastatic breast cancer that overexpresses HER2. N Engl J. Med. 2001 Mar. 15; 344(11):783-92; Rehwald U, Schulz H, Reiser M, Sieber M, Staak J O, Morschhauser F, Driessen C, Rudiger T, Muller-Hermelink K, Diehl V, Engert A. Treatment of relapsed CD20+ Hodgkin lymphoma with the monoclonal antibody rituximab is effective and well tolerated: results of a phase 2 trial of the German Hodgkin Lymphoma Study Group. Blood. 2003 Jan. 15; 101 (2):420-424; Fang G, Kim C N, Perkins C L, Ramadevi N, Winton E, Wittmann S and Bhalla K N. (2000). Blood, 96, 2246-2253). These drugs are clinically effective and better tolerated than traditional anti-cancer agents because they target only transformed cells. Hence, such drugs not only improve survival and quality of life for cancer patients, but also validate the concept of molecularly targeted cancer therapy. Furthermore, targeted drugs can enhance the efficacy of standard chemotherapy when used in combination with it (Gianni L. (2002). Oncology, 63 Suppl 1, 47-56; Klejman A, Rushen L, Morrione A, Slupianek A and Skorski T. (2002). Oncogene, 21, 5868-5876). Therefore, future cancer treatments will probably involve combining conventional drugs with target-specific agents aimed at different characteristics of tumor cells such as angiogenesis and invasiveness.

These modulatory methods can be performed ex vivo or in vitro (e.g., by culturing the cell with the agent) or, alternatively, in vivo (e.g., by administering the agent to a subject). The methods involve administering a protein or combination of proteins or a nucleic acid molecule or combination of nucleic acid molecules as therapy to counteract aberrant expression of the differentially expressed genes or aberrant activity of their gene products.

Diseases and disorders that are characterized by increased (relative to a subject not suffering from the disease or disorder) expression levels or biological activities of genes and gene products, respectively, may be treated with therapeutics that antagonize (i.e., reduce or inhibit) activity of the over-expressed gene or genes. Therapeutics that antagonize activity can be administered therapeutically or prophylactically.

Accordingly, therapeutics that may be utilized in the context of the present invention include, e.g., (i) a polypeptide of the over-expressed or under-expressed gene or genes, or analogs, derivatives, fragments or homologs thereof; (ii) antibodies to the over-expressed gene or gene products; (iii) nucleic acids encoding the over-expressed or under-expressed gene or genes; (iv) antisense nucleic acids or nucleic acids that are "dysfunctional" (i.e., due to a heterologous insertion within the nucleic acids of one or more over-expressed gene or genes); (v) small interfering RNA (siRNA); or (vi) modulators (i.e., inhibitors, agonists and antagonists that alter the interaction between an over-expressed or under-expressed polypeptide and its binding partner). The dysfunctional antisense molecules are utilized to "knockout" endogenous function of a polypeptide by homologous recombination (see, e.g., Capecchi, Science 244: 1288-1292 1989).

Diseases and disorders that are characterized by decreased (relative to a subject not suffering from the disease or disorder) biological activity may be treated with therapeutics that increase (i.e., are agonists to) activity. Therapeutics that up-regulate activity may be administered in a therapeutic or prophylactic manner. Therapeutics that may be utilized include, but are not limited to, a polypeptide (or analogs, derivatives, fragments or homologs thereof) or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a gene whose expression is altered). Methods that are well-known within the art include, but are not limited to, immunoassays (e.g., by Western blot analysis, immunoprecipitation followed by sodium dodecyl sulfate (SDS) polyacrylamide gel electrophoresis, immuno-cytochemistry, etc.) and/or hybridization assays to detect expression of mRNAs (e.g., Northern assays, dot blots, in situ hybridization, etc.).

Prophylactic administration occurs prior to the manifestation of overt clinical symptoms of disease, such that a disease or disorder is prevented or, alternatively, delayed in its progression.

Therapeutic methods of the present invention may include the step of contacting a cell with an agent that modulates one or more of the activities of the gene products of the differentially expressed genes. Examples of agent that modulates protein activity include, but are not limited to, nucleic acids, proteins, naturally-occurring cognate ligands of such proteins, peptides, peptidomimetics, and other small molecule. For example, a suitable agent may stimulate one or more protein activities of one or more differentially under-expressed genes.

Vaccinating Against Breast Cancer:

The present invention also relates to a method of treating or preventing breast cancer in a subject comprising the step of administering to said subject a vaccine comprising a polypeptide encoded by a nucleic acid selected from the group consisting of the BRC-associated genes listed in tables 3, 5, and 7 (i.e., up-regulated genes), an immunologically active fragment of said polypeptide, or a polynucleotide encoding such a polypeptide or fragment thereof. Administration of the polypeptide induces an anti-tumor immunity in a subject. To induce anti-tumor immunity, a polypeptide encoded by a nucleic acid selected from the group consisting of the BRC-associated genes listed in tables 3, 5, and 7, an immunologically active fragment of said polypeptide, or a polynucleotide encoding such a polypeptide or fragment thereof is administered to subject in need thereof. Furthermore, the polypeptide encoded by a nucleic acid selected from the group consisting of the BRC-associated genes listed in tables 5 and 7 may induce antitumor immunity against invasion of breast cancer and IDC, respectively. The polypeptide or the immunologically active fragments thereof are useful as vaccines against BRC. In some cases, the proteins or fragments thereof may be administered in a form bound to the T cell receptor (TCR) or presented by an antigen presenting cell (APC), such as macrophage, dendritic cell (DC), or B-cells. Due to the strong antigen presenting ability of DC, the use of DC is most preferable among the APCs.

In the present invention, a vaccine against BRC refers to a substance that has the ability to induce anti-tumor immunity upon inoculation into animals. According to the present invention, polypeptides encoded by the BRC-associated genes listed in tables 3, 5, and 7, or fragments thereof, were suggested to be HLA-A24 or HLA-A*0201 restricted epitopes peptides that may induce potent and specific immune response against BRC cells expressing the BRC-associated genes listed in tables 3, 5, and 7. Thus, the present invention also encompasses a method of inducing anti-tumor immunity using the polypeptides. In general, anti-tumor immunity includes immune responses such as follows:

induction of cytotoxic lymphocytes against tumors,
    induction of antibodies that recognize tumors, and
    induction of anti-tumor cytokine production.

Therefore, when a certain protein induces any one of these immune responses upon inoculation into an animal, the protein is determined to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. Specifically, a foreign substance that enters the living body is presented to T cells and B cells by the action of antigen presenting cells (APCs). T cells that respond to the antigen presented by the APCs in an antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to a T cell via an APC, and detecting the induction of CTLs. Furthermore, APCs have the effect of activating CD4+ T cells, CD8+ T cells, macrophages, eosinophils, and NK cells. Since CD4+ T cells and CD8+ T cells are also important in anti-tumor immunity, the anti-tumor immunity-inducing action of the peptide can be evaluated using the activation effect of these cells as indicators.

A method for evaluating the inducing action of CTLs using dendritic cells (DCs) as the APC is well known in the art. DCs are a representative APCs having the strongest CTL-inducing action among APCs. In this method, the test polypeptide is initially contacted with DCs, and then the DCs are contacted with T cells. Detection of T cells having cytotoxic effects against the cells of interest after the contact with DC shows that the test polypeptide has an activity of inducing the cytotoxic T cells. Activity of CTLs against tumors can be detected, for example, using the lysis of $^{51}$Cr-labeled tumor cells as the indicator. Alternatively, the method of evaluating the degree of tumor cell damage using $^3$H-thymidine uptake activity or LDH (lactose dehydrogenase)-release as the indicator is also well known.

Apart from DCs, peripheral blood mononuclear cells (PBMCs) may also be used as the APC. The induction of CTLs has been reported to be enhanced by culturing PBMCs in the presence of GM-CSF and IL-4. Similarly, CTLs have been shown to be induced by culturing PBMCs in the presence of keyhole limpet hemocyanin (KLH) and IL-7.

Test polypeptides confirmed to possess CTL-inducing activity by these methods are deemed to be polypeptides having DC activation effect and subsequent CTL-inducing activity. Therefore, polypeptides that induce CTLs against tumor cells are useful as vaccines against tumors. Furthermore, APCs that have acquired the ability to induce CTLs against tumors through contact with the polypeptides are also useful as vaccines against tumors. Furthermore, CTLs that have acquired cytotoxicity due to presentation of the polypeptide antigens by APCs can be also used as vaccines against tumors. Such therapeutic methods for tumors, using anti-tumor immunity due to APCs and CTLs, are referred to as cellular immunotherapy.

Generally, when using a polypeptide for cellular immunotherapy, efficiency of the CTL-induction is known to be increased by combining a plurality of polypeptides having different structures and contacting them with DCs. Therefore, when stimulating DCs with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide is deemed to have the ability to induce anti-tumor immunity.

Anti-tumor immunity is induced by administering the vaccine of this invention, and the induction of anti-tumor immunity enables treatment and prevention of BRC. Therapy against cancer or prevention of the onset of cancer includes any of the following steps, such as inhibition of the growth of cancerous cells, involution of cancer, and suppression of the occurrence of cancer. A decrease in mortality and morbidity of individuals having cancer, decrease in the levels of tumor markers in the blood, alleviation of detectable symptoms accompanying cancer, and such are also included in the therapy or prevention of cancer. Such therapeutic and preventive effects are preferably statistically significant. For example, in observation, at a significance level of 5% or less, wherein the therapeutic or preventive effect of a vaccine against cell proliferative diseases is compared to a control without vaccine administration. For example, Student's t-test, the Mann-Whitney U-test, or ANOVA may be used for statistical analysis.

The above-mentioned protein having immunological activity or a vector encoding the protein may be combined with an adjuvant. An adjuvant refers to a compound that enhances the immune response against the protein when administered together (or successively) with the protein having immunological activity. Exemplary adjuvants include, but are not limited to, cholera toxin, *salmonella* toxin, alum, and such, but are not limited thereto. Furthermore, the vaccine of this invention may be combined appropriately with a pharmaceutically acceptable carrier. Examples of such carriers include sterilized water, physiological saline, phosphate buffer, culture fluid, and such. Furthermore, the vaccine may contain as necessary, stabilizers, suspensions, preservatives, surfactants, and such. The vaccine can be administered systemically or locally. Vaccine administration can be performed by single administration, or boosted by multiple administrations.

When using an APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and following the induction of APCs or CTLs, the cells may be administered to the subject. APCs can be also induced by introducing a vector encoding the polypeptide into PBMCs ex vivo. APCs or CTLs induced in vitro can be cloned prior to administration. By cloning and growing cells having high activity of damaging target cells, cellular immunotherapy can be performed more effectively. Furthermore, APCs and CTLs isolated in this manner may be used for cellular immunotherapy not only against individuals from whom the cells are derived, but also against similar types of tumors from other individuals.

Furthermore, a pharmaceutical composition for treating or preventing a cell proliferative disease, such as cancer, comprising a pharmaceutically effective amount of the polypeptide of the present invention is provided. The pharmaceutical composition may be used for raising anti tumor immunity.

Pharmaceutical Compositions for Inhibiting BRC or Malignant BRC:

In the context of the present invention, suitable pharmaceutical formulations include those suitable for oral, rectal, nasal, topical (including buccal and sub-lingual), vaginal or parenteral (including intramuscular, sub-cutaneous and intravenous) administration, or for administration by inhalation or insufflation. Preferably, administration is intravenous. The formulations are optionally packaged in discrete dosage units.

Pharmaceutical formulations suitable for oral administration include capsules, cachets or tablets, each containing a predetermined amount of active ingredient. Suitable formulations also include powders, granules, solutions, suspensions and emulsions. The active ingredient is optionally administered as a bolus electuary or paste. Tablets and capsules for oral administration may contain conventional excipients, such as binding agents, fillers, lubricants, disintegrant and/or wetting agents. A tablet may be made by compression or molding, optionally with one or more formulational ingredients. Compressed tablets may be prepared by compressing in a suitable machine the active ingredients in a free-flowing form, such as a powder or granules, optionally mixed with a binder, lubricant, inert diluent, lubricating, surface active and/or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives, such as suspending agents, emulsifying agents, non-aqueous vehicles (which may include edible oils), and/or preservatives. The tablets may optionally be formulated so as to provide slow or controlled release of the active ingredient therein. A package of tablets may contain one tablet to be taken on each of the month.

Formulations suitable for parenteral administration include aqueous and non-aqueous sterile injection solutions, optionally contain anti-oxidants, buffers, bacteriostats and solutes which render the formulation isotonic with the blood of the intended recipient; as well as aqueous and non-aqueous sterile suspensions including suspending agents and/or thickening agents. The formulations may be presented in unit dose or multi-dose containers, for example as sealed ampoules and vials, and may be stored in a freeze-dried (lyophilized) condition, requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations suitable for rectal administration include suppositories with standard carriers such as cocoa butter or polyethylene glycol. Formulations suitable for topical administration in the mouth, for example, buccally or sublingually, include lozenges, containing the active ingredient in a flavored base such as sucrose and acacia or tragacanth, and pastilles, comprising the active ingredient in a base such as gelatin and glycerin or sucrose and acacia. For intra-nasal administration, the compounds of the invention may be used as a liquid spray, a dispersible powder, or in the form of drops. Drops may be formulated with an aqueous or non-aqueous base also comprising one or more dispersing agents, solubilizing agents and/or suspending agents.

For administration by inhalation the compounds can be conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base, such as lactose or starch. The powder composition may be presented in unit dosage form, for example, as capsules, cartridges, gelatin or blister packs, from which the powder may be administered with the aid of an inhalator or insufflators.

Other formulations include implantable devices and adhesive patches which release a therapeutic agent.

When desired, the above described formulations, adapted to give sustained release of the active ingredient, may be employed. The pharmaceutical compositions may also contain other active ingredients, such as antimicrobial agents, immunosuppressants and/or preservatives.

It should be understood that in addition to the ingredients particularly mentioned above, the formulations of this invention may include other agents conventional in the art with regard to the type of formulation in question. For example, formulations suitable for oral administration may include flavoring agents.

Preferred unit dosage formulations contain an effective dose, as recited below, or an appropriate fraction thereof, of the active ingredient.

For each of the aforementioned conditions, the compositions, e.g., polypeptides and organic compounds, can be administered orally or via injection at a dose ranging from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The dose employed will depend upon a number of factors, including the age and sex of the subject, the precise disorder being treated, and its severity. Also the route of administration may vary depending upon the condition and its severity. In any event, appropriate and optimum dosages may be routinely calculated by those skilled in the art, taking into consideration the above-mentioned factors.

Aspects of the present invention are described in the following examples, which are not intended to limit the scope of the invention described in the claims. The following examples illustrate the identification and characterization of genes differentially expressed in BRC cells.

EXAMPLES

Tissue obtained from diseased tissue (e.g., epithelial cells from BRC) and normal tissues was evaluated to identify genes which are differently expressed or a disease state, e.g., BRC. The assays were carried out as follows.
Patients and Tissue Samples:

Primary breast cancers were obtained with informed consent from 81 patients (12 ductal carcinoma in situ and 69 invasive ductal carcinoma from 2 cm to 5 cm(T2), median age 45 in a range of 21 to 68 years old) who treated at Department of Breast Surgery, Cancer Institute Hospital, Tokyo, Japan, concerning which all patients had given informed consent (Table 12). Clinical information was obtained from medical records and each tumor was diagnosed according to histopathological subtype and grade by pathologists. Tumor tissue was used to evaluate tumor type (according to the World Health Organization classification and the Japanese cancer society classification). Clinical stage was judged according to the JBCS TNM classification. No significant differences were observed between node-positive and node-negative cases. The presence of angioinvasive growth and extensive lymphocytic infiltrate was determined by pathologists, Estrogen receptor (ER) and progesterone receptor (PgR) expression was determined by EIA (ER negative when less than 13 fmol/mg protein, BML). A mixture of normal breast ductal cells from the 15 premenopausal patients with breast cancer or the 12 post menopausal patients were used as normal controls, respectively. All samples were immediately frozen and stored at −80° C.

Tissue Samples and LMM:

Clinical and pathological information on the tumor is detailed in Table 12. Samples were embedded in TissueTek OCT medium (Sakura) and then stored at −80° C. until use. Frozen specimens were serially sectioned in 8-µm slices with a cryostat and stained with hematoxylin and eosin to define the analyzed regions. To avoid cross-contamination of cancer and noncancerous cells, these two populations were prepared by EZ Cut LMM System (SL Microtest GmbH) followed the manufacture's protocol with several modifications. To minimize the effects during storage process and tissue collection, the cancer tissues were carefully handled by the same procedure. To check the quality of RNAs, total RNA extracted from the residual tissue of each case were electrophoresed under the degenerative agarose gel, and confirmed their quality by a presence of ribosomal RNA bands.

RNA Extraction and T7-Based RNA Amplification:

Total RNA was extracted from each population of laser captured cells into 350 µl RLT lysis buffer (QIAGEN). The extracted RNA was treated for 30 minutes at room temperature with 30 units of DNase I (QIAGEN). After inactivation at 70° C. for 10 min, the RNAs were purified with an RNeasy Mini Kit (QIAGEN) according to the manufacturer's recommendations. All of the DNase I treated RNA was subjected to T7-based amplification using Ampliscribe T7 Transcription Kit (Epicentre Technologies). Two rounds of amplification yielded 28.8-329.41 g of amplified RNAs (aRNAs) for each sample, whereas when RNAs from normal samples from 15 premenopausal patients or 12 postmenopausal patients were amplified, total of 2240.2 µg and 2023.8 µg were yielded, respectively. 2.5 pg aliquots of aRNA from each cancerous cells and noncancerous breast ductal cells were reverse-transcribed in the presence of Cy5-dCTP and Cy3-dCTP (Amersham Biosciences), respectively.

cDNA Microarrays:

A "genome-wide" cDNA microarray system was established containing 23,040 cDNAs selected from the UniGene database (build #131) the National Center for Biotechnology Information (NCBI). Fabrication of cDNA microarray slides has been described elsewhere (Ono K, Tanaka T, Tsunoda T, Kitahara O, Kihara C, Okamoto A, Ochiai K, Katagiri T and Nakamura Y. Identification by cDNA Microarray of Genes Involved in Ovarian Carcinogenesis. *Cancer Res.,* 60, 5007-11, 2000). Briefly, the cDNAs were amplified by reverse transcription-PCR using poly(A)+RNA isolated from various human organs as templates; lengths of the amplicons ranged from 200 to 1100 bp without repetitive or poly(A) sequences. The PCR products were spotted in duplicate on type-7 glass slides (Amersham Bioscience) using a Lucidea Array Spotter (Amersham Biosciences); 4,608 or 9,216 genes were spotted in duplicate on a single slide. Three different sets of slides (total 23,040 genes) were prepared, each of which were spotted with the same 52 housekeeping genes and two kinds of negative-control genes as well.

Hybridization and Acquisition of Data:

Hybridization and washing were performed according to protocols described previously except that all processes were carried out with an Automated Slide Processor (Amersham Biosciences) (Giuliani, N., et al., V. Human myeloma cells stimulate the receptor activator of nuclear factor-kappa B ligand (RANKL) in T lymphocytes: a potential role in multiple myeloma bone disease. Blood, 100: 4615-4621, 2002). The intensity of each hybridization signal was calculated photometrically by the ArrayVision computer program (Amersham Biosciences) and background intensity was subtracted. The fluorescence intensities of Cy5 (tumor) and Cy3 (control) for each target spot were adjusted so the mean Cy5/Cy3 ratio was performed using averaged signals from the 52 housekeeping genes. Because data derived from low signal intensities are less reliable, a cut-off value for signal intensities on each slide was determined and excluded genes from further analysis when both Cy3 and Cy5 dyes gave signal intensities lower than the cut-off. A cut-off value for each expression level was automatically calculated according to background fluctuation. When both Cy5 and Cy3 signal intensities were lower than the cut-off values, expression of the corresponding gene in that sample was assessed as absent. The Cy5/Cy3 ratio was calculated as the relative expression ratio. For other genes, the Cy5/Cy3 ratio was calculated using the raw data for each sample.

Signal intensities of Cy3 and Cy5 from the 23,040 spots were quantified and analyzed by substituting backgrounds, using ArrayVision software (Imaging Research, Inc., St. Catharines, Ontario, Canada). Subsequently the fluorescent intensities of Cy5 (tumor) and Cy3 (control) for each target spot were adjusted so that the mean Cy3/Cy5 ratio of 52 housekeeping genes on the array was equal to one. Because data derived from low signal intensities are less reliable, a cut-off value on each slide was determined as described previously (Ono, K., et al., Identification by cDNA microarray of genes involved in ovarian carcinogenesis. Cancer Res, 60: 5007-5011, 2000) and those genes were excluded from further analysis when both Cy3 and Cy5 dyes yielded signal intensities lower than the cut-off (Saito-Hisaminato, A., Katagiri, T., Kakiuchi, S., Nakamura, T., Tsunoda, T., and Nakamura, Y. Genome-wide profiling of gene expression in 29 normal human tissues with a cDNA microarray. DNA Res, 9: 35-45, 2002). For other genes, the Cy5/Cy3 ratio was calculated using the raw data for each sample.

Calculation of Contamination Percentage:

Perilipin (PLIN) and fatty acid binding protein 4 (FABP4) were expressed exclusively in adipose tissue and mammary gland tissue by gene expression profiles in 29 normal human tissues with a cDNA microarray (Saito-Hisaminato, A. et al., Genome-wide profiling of gene expression in 29 normal human tissues with a cDNA microarray. DNA Res, 9: 35-45, 2002). These were used to evaluate the proportion of adipocytes present in the population of microdissected normal breast ductal epithelial cells. Each aRNA of poly $A^+$RNA isolated from normal whole-mammary gland (Clontech) and of microdissected normal breast ductal epithelial cells were reverse-transcribed in the presence of Cy5-dCTP and Cy3-dCTP, respectively. After hybridization on microarray slides, the Cy5/Cy3 ratio was calculated. The average of each ratio was decided by the result used mammary gland tissue and microdissected normal breast ductal cells in premenopausal patients and postmenopausal patients.

Cluster Analysis Of 102 Samples with 81 Breast Carcinoma According to Gene-Expression Profiles:

An unsupervised hierarchical clustering method was applied to both genes and tumors. To obtain reproducible clusters for classification of the 102 samples, 710 genes for which valid data were obtained in 80% of the experiments, and whose expression ratios varied by standard deviations of more than 1.1, were selected. The analysis was performed using web-available software ("Cluster" and "TreeView") written by M. Eisen (at genome-www5.stanford.edu/MicroArray/SMD/restech.html). Before applying the clustering algorithm, the fluorescence ratio for each spot was log-transformed and then median-centered the data for each sample to remove experimental biases and used average linkage.

Identification of Up or Down-Regulated Genes Between DCIS and IDC:

The relative expression ratio of each gene (Cy5/Cy3 intensity ratio) was classified into one of four categories: (A) up-regulated (expression ratio>2.0); (B) down-regulated (expression ratio<0.5); (C) unchanged (expression ratio between 0.5 and 2.0); and (D) not expressed (or slight expression but under the cutoff level for detection). These categories were used to detect a set of genes for which changes in the expression ratios were common among samples. To detect candidate genes that were commonly up- or down-regulated in each group, the overall expression patterns of 23,040 genes were first screened to select genes with expression ratios >3.0 or <⅓ that were present in >50% of the groups categorized.

Semi-quantitative RT-PCR:

Five up-regulated genes were selected and their expression levels were examined by applying the semi-quantitative RT-PCR experiments. A 1-μg aliquot of aRNA from each sample was reverse-transcribed for single-stranded cDNAs using random primer (Taniguchi, K., et al., Mutational spectrum of beta-catenin, AXIN1, and AXIN2 in hepatocellular carcinomas and hepatoblastomas. Oncogene, 21: 4863-4871, 2002) and Superscript II (Life Technologies, Inc.). Each cDNA mixture was diluted for subsequent PCR amplification with the primer sets that were shown in Table 9. Expression of GAPDH served as an internal control. PCR reactions were optimized for the number of cycles to ensure product intensity within the linear phase of amplification.

Identification of Genes Responsible For Histopathological Status, ER Status and Lymph-Node Metastasis in Breast Cancer:

The discriminating genes were selected using the following two criteria: (1) signal intensities higher than the cut-off level in at least 70% (ER status) or 50% (Histopathological status and lymph-node metastasis) of the cases; (2) |Med$_r$−Med$_n$|>1 (ER status) or 0.5 (Histopathological status and lymph-node metastasis) of the cases, where Med indicates the median derived from log-transformed relative expression ratios in node-positive cases or -negative cases. Next, a random permutation test was applied to identify genes that were expressed differently between one group (group A) and another (group B). Mean ($\mu$) and standard ($\sigma$) deviations were calculated from the log-transformed relative expression ratios of each gene in group A (r) and group B (n) cases. A discrimination score (DS) for each gene was defined as follows:

$$DS=(\mu_r-\mu_n)/(\sigma_r+\sigma_n)$$

Permutation tests were carried out to estimate the ability of individual genes to distinguish between group A and group B; samples were randomly permutated between the two classes 10,000 times. Since the DS dataset of each gene showed a normal distribution, a P value was calculated for the user-defined grouping (Golub, T. et al., Molecular classification of cancer: class discovery and class prediction by gene expression monitoring. Science, 286: 531-537, 1999).

Calculation of Prediction Score for Lymph-Node Metastasis:

Prediction scores were calculated according to procedures described previously (Golub, T. et al., Molecular classification of cancer: class discovery and class prediction by gene expression monitoring. Science, 286: 531-537, 1999). Each gene (gi) votes for either lymph node-negative or lymph node-positive depending on whether the expression level (xi) in the sample is closer to the mean expression level of node-negative or -positive in reference samples. The magnitude of the vote (vi) reflects the deviation of the expression level in the sample from the average of the two classes:

$$V_i=|x_i-(\mu_r-\mu_n)/2|$$

The votes were summed to obtain total votes for the node-negative (Vr) and node-positive (Vn), and calculated PS values as follows:

$$PS=(Vr-Vn)/(Vr+Vn)\times 100,$$

reflecting the margin of victory in the direction of either node-negative or node-positive. PS values range from −100 to 100; a higher absolute value of PS reflects a stronger prediction.

Evaluation of Classification and Leave-One-Out Test:

The classification score (CS) was calculated the using prediction scores of lymph node-negatives (PSr) and node-positives (PSn) in each gene set, as follows:

$$CS=(\mu_{PSr}-\mu_{PSn})/(\sigma_{PSr}+\sigma_{PSn})$$

A larger value of CS indicates better separation of the two groups by the predictive-scoring system. For the leave-one-out test, one sample is withheld, the permutation p-value and mean expression levels are calculated using remaining samples, and the class of the withheld sample is subsequently evaluated by calculating its prediction score. This procedure was repeated for each of the 20 samples.

Cell Lines

Human-breast cancer cell lines HBL-100, HCC1937, MCF-7, MDA-MB-435s, YMB1, SKBR3, T47D, BT-20, BT-474, BT-549, HCC1143, HCC1500, HCC1599, MDA-MB-157, MDA-MB453, OUCB-F, ZR-75-1, COS-7 cell lines are purchased from American Type Culture Collection (ATCC) and are cultured under their respective depositors' recommendation. HBC4, HBC5 and MDA-MB-231 cells lines are kind gifts from Dr. Yamori of Molecular Pharmacology, Cancer Chemotherapy Centre of the Japanese Foundation for Cancer Research. All cells were cultured in appropriate media; i.e. RPMI-1640 (Sigma, St. Louis, Mo.) for HBC4, HBC5, T47D, YMB1, OUCB-F, ZR-75-1, BT-549, HCC1143, HCC1500, HCC1599 and HCC1937 (with 2 mM L-glutamine); Dulbecco's modified Eagle's medium (Invitrogen, Carlsbad, Calif.) for BT474, HBL100, COS7; EMEM (Sigma) with 0.1 mM essential amino acid (Roche), 1 mM sodium pyruvate (Roche), 0.01 mg/ml Insulin (Sigma) for BT-20 and MCF-7; McCoy (Sigma) for SKBR3 (with 1.5 mM L-glutamine); L-15 (Roche) for MDA-MB-231, MDA-MB-157, MDA-MB453 and MDA-MB-435S. Each medium was supplemented with 10% fetal bovine serum (Cansera) and 1% antibiotic/antimycotic solution (Sigma). MDA-MB-231 and MDA-MB-435S cells were maintained at 37° C. an atmosphere of humidified air without $CO_2$. Other cell lines were maintained at 37° C. an atmosphere of humidified air with 5% $CO_2$. Clinical samples (breast cancer and normal breast duct) were obtained from surgical specimens, concerning which all patients had given informed consent.

Northern-blot Analysis

Total RNAs were extracted from all breast cancer cell lines using RNeasy kit (QIAGEN) according to the manufacturer's instructions. After treatment with DNase I (Nippon Gene, Osaka, Japan), mRNA was isolated with mRNA purification kit (Amersham Biosciences) following the manufacturer's instructions. A 1-μg aliquot of each mRNA, along with polyA(+) RNAs isolated from normal adult human breast (Biochain), lung, heart, liver, kidney, bone marrow (BD, Clontech, Palo Alto, Calif.), were separated on 1% denaturing agarose gels and transferred to nylon membranes (Breast cancer-Northern blots). Breast cancer- and Human multiple-tissue Northern blots (Clontech, Palo Alto, Calif.) were hybridized with an [$\alpha^{32}$P]-dCTP-labeled PCR products of A7870 prepared by RT-PCR (see below). Pre-hybridization, hybridization and washing were performed according to the supplier's recommendations. The blots were autoradiographed with intensifying screens at −80° C. for 14 days. Specific probes for A7870 (320 bp) was prepared by RT-PCR using the following primer set; 5'-AGACCCTAAA-GATCGTCCTTCTG-3' (SEQ ID NO:13) and 5'-GTGTTT-TAAGTCAGCATGAGCAG-3' (SEQ ID NO:14) and is radioactively labeled with megaprime DNA labeling system (Amersham bioscience).

Immunocytochemical Staining

For constructing of A7870 expression vectors, the entire coding sequence of A7870 cDNA was amplified by the PCR using KOD-Plus DNA polymerase (Toyobo, Osaka, Japan). The PCR products were inserted into the EocRI and Xho I sites of pCAGGSn3FH-HA expression vector. This construct (pCAGGS-A7870-HA) was confirmed by DNA sequencing. Next, to initially examine the sub-cellular localization of exogenous A7870, we seeded COS7 cells at 1×10⁵ per well for exogenous expression. After 24 hours, we transiently transfected with 1 µg of pCAGGS-A7870-HA into COS7 cells using FuGENE 6 transfection reagent (Roche) according to the manufacturer's instructions, respectively. Then, cells were fixed with PBS containing 4% paraformaldehyde for 15 min, and rendered permeable with PBS containing 0.1% Triton X-100 for 2.5 min at 4° C. Subsequently the cells were covered with 3% BSA in PBS for 12 hours at 4° C. to block non-specific hybridization. Next, A7870-HA-transfected COS7 cells were incubated with a mouse anti-HA antibody (SANTA CRUZ) at 1:1000 dilution and anti-TOPK polyclonal antibody (Cell Signaling) at 1:1000 dilution. After washing with PBS, both transfected-cells were stained by an Alexa594-conjugated anti-mouse secondary antibody (Molecular Probe) at 1:5000 dilution.

We further confirmed the sub-cellular localization of endogenous A7870 protein in breast cancer cell lines, T47D, BT-20 and HBC5 at 2×10⁵ cells per well. Cells were with a rabbit anti-TOPK polyclonal antibody made of synthetic peptide corresponding to amino acids at the c-terminus of human PBK/TOPK at 1:1000 dilution. After washing with PBS, the cells were stained by an Alexa488-conjugated anti-rabbit secondary antibody (Molecular Probe) at 1:3000 dilution. Nuclei were counter-stained with 4',6'-diamidine-2'-phenylindole dihydrochloride (DAPI). Fluorescent images were obtained under a TCS SP2 AOBS microscope (Leica, Tokyo, Japan).

Construction of A7870 Specific-siRNA Expression Vector Using psiU6BX3.0

We established a vector-based RNAi system using psiU6BX3.0 siRNA expression vector according to the previous report (Shimokawa T, Furukawa Y, Sakai M, Li M, Miwa N, Lin Y M, Nakamura Y (2003). Cancer Res, 63, 6116-6120). A siRNA expression vector against A7870 (psiU6BX-A7870) was prepared by cloning of double-stranded oligonucleotides in Table 13 into the BbsI site in the psiH1BX3.0 vector. Control plasmids, psiU6BX-SC and psiU6BX-LUC was prepared by cloning double-stranded oligonucleotides of 5'-TCCCGCGCGCTTTGTAGGATTCGT-TCAAGAGACGAATCCTACAAAGCGCGC-3'(SEQ ID NO:15) and 5'-AAAAGCGCGCTTTGTAGGAT-TCGTCTCTTGAACGAATCCTACAAAGCGCGC-3'(SEQ ID NO:16) for SC (scrambled control); 5'-TCCCCG-TACGCGGAATACTTCGATTCAAGAGATC-GAAGTATTCCGCGTACG-3'(SEQ ID NO:17) and 5'-AAAACGTACGCGGAATACTTCGATCTCT-TGAATCGAAGTATTCCGCGTACG-3' (SEQ ID NO:18) for LUC (luciferase control) into the BbsI site in the psiU6BX3.0 vector, respectively.

Gene-silencing Effect of A7870

Human breast cancer cells lines, T47D or BT-20 was plated onto 15-cm dishes (4×10⁶ cells/dish) and transfected with 16 µg of each psiU6BX-LUC (luciferase control), psiU6BX-SC (scrambled control) as negative controls and psiU6BX-A7870 using FuGENE6 reagent according to the supplier's recommendations (Roche). 24 hour after transfection, cells are re-seeded again for colony formation assay (2×10⁶ cells/10 cm dish), RT-PCR (2×10⁶ cells/10 cm dish) and MTT assay (2×10⁶ cells/well). We selected the A7870-introducing cells with medium containing 0.7 mg/ml or 0.6 mg/ml of neomycin (Geneticin, Gibco) in T47D or BT-20 cells, respectively. Afterward, we changed medium every two days for 3 weeks. To evaluate the functioning of siRNA, total RNA was extracted from the cells at 11 days after neomycin selection, and then the knockdown effect of siRNAs was confirmed by a semi-quantitative RT-PCR using specific primer sets for A7870 and GAPDH; 5'-ATGGAAATCCCATCACCATCT-3' (SEQ ID NO:19) and 5'-GGTTGAGCACAGGGTACTT-TATT-3' (SEQ ID NO:20) for GAPDH as an internal control, and 5'-GCCTTCATCATCCAAACATT-3' (SEQ ID NO:21) and 5'-GGCAAATATGTCTGCCTTGT-3' (SEQ ID NO:22) for A7870.

Moreover, transfectants expressing siRNAs using T47D or BT-20 cell lines were grown for 23 days in selective media containing neomycin, respectively. After fixation with 4% paraformaldehyde, transfected cells were stained with Giemsa solution to assess colony formation. MTT assays were performed to quantify cell viability. After 10 days of culture in the neomycin-containing medium, MTT solution (3-(4,5-dimethylthiazol-2-yl)-2,5-diphenyl tetrazolium bromide) (Sigma) was added at a concentration of 0.5 mg/ml. Following incubation at 37° C. for 2.5 hours, acid-SDS (0.01N HCl/10% SDS) was added; the suspension was mixed vigorously and then incubated overnight at 37° C. to dissolve the dark blue crystals. Absorbance at 570 nm was measured with a Microplate Reader 550 (BioRad). To evaluate the functioning of siRNA, total RNA is extracted from cells 7 days after selection, MTT assay is performed at 10 days after selection using Cell Counting Kit-8 (Dojindo) according to manufacture's protocol. Absorbance is measured at 570 nm wavelength with a Microplate Reader 550 (BioRad). For colony formation assay, cells are fixed with 4% paraformaldehyde for 15 min before staining with Giemsa's solution (Merck). Each experiment is triplicated.

Results

Classification Analysis on the Basis of Precise Gene Expression Profiles of Breast Cancer:

Since breast cancer contains a low population of cancer cells in tumor mass and originates from normal epithelial duct cells, microdissection was carried out to avoid contamination of the surrounding non-cancerous cells or non-normal ductal epithelial cells. As the great majority of cells in breast tissue are adipocytes, it was considered to not be suitable to use the whole breast tissue to analyze cancer-specific expression profiles in that organ. As shown in FIG. 1, the representative examples of DCIS (case 10326T), IDC (10502T), and normal ductal epithelium (10341N) were microdissected from each clinical specimen. This allows the subsequent gene expression profiles to be obtained more precisely. The proportion of adipocytes that contaminated the microdissected population of normal breast ductal epithelial cells serving as a universal control were examined by measuring the signal intensities of two genes (i.e., PLIN and FABP4) that are highly expressed in adipose and mammary gland tissues as described previously (Saito-Hisaminato, A., et al., Genome-wide profiling of gene expression in 29 normal human tissues with a cDNA microarray. DNA Res, 9: 35-45, 2002). When the signal intensities of these genes were investigated in whole mammary gland tissue, which contains a large number of adipocytes, the average of ratio of signal intensities of these gene were approximately 99.4%; the ratio in microdissected normal breast ductal epithelial cells was approximately 0.6% (see Contamination percentage section in Materials and Methods). Therefore, it was estimated that the average proportion of contaminating adipocytes in the populations of control cells to be 0.6% after microdissection. First, an unsupervised two-dimensional hierarchical clustering algorithm was applied to group genes on the basis of similarity in their expression pattern over 102 clinical samples: 81 microdissected different clinical breast cancer specimens, 11 microdissected different histological types in 10 individuals, 2 whole breast cancer tissues, 6 microdissected normal breast ductal cells and two whole mammary gland tissues. Reproducible clusters were obtained with 710 genes (see Material and methods); their expression patterns across the 102 samples are shown in FIG. 2A. In the sample axis, the 102 samples were clustered into three major groups (Group A, B and C) on the basis of their expression profiles. Then, this classification was associated with clinical parameters, especially estrogen receptor (ER) as determined with EIA. Out of 55 ER-positive tumors, 45 cases clustered into same branch (Group B) of the tumor dendrogram, suggesting a tendency with ER status. Moreover, 7 of 10 cases with different histological type (sample#10864, 10149, 10818, 10138, 10005, 10646 and 10435) were labeled and hybridized in independent experiments were clustered most closely within same group. In particular, among them, the one duplicated case (10149a1 and 10149a1T) was also clustered into the shortest branch, supporting the reproducibility and reliability of the microarray data. Remarkably, Group C contained microdissected non-cancerous cells and breast cancer whole tissues, with the exception of one microdissected tumor case, suggesting this data represents accurate breast cancer specific-expression profiles.

Furthermore, a two-dimensional hierarchical clustering analysis of 89 genes was performed across 16 samples with 2 differentiated lesions microdissected from 8 breast cancer patients. As a result, breast cancer samples with different phenotype lesions were closely adjacent (FIG. 2B). Next, a random permutation test was carried out to identify the genes that were differentially expressed in the patient-matched phenotypically well- or poorly-differentiated lesions from microdissected 8 cancer specimen. As shown in FIG. 2C, clustering analysis using 25 genes that showed differential expression can separate between well- or poorly-differentiated invasive ductal cancer cells. These 25 genes (Table 1) included some key factors whose possible roles in invasion and cell growth had been reported previously: TNFSF11, ITGA5 and NFAT5 (Giuliani, N., et al., Human myeloma cells stimulate the receptor activator of nuclear factor-kappa B ligand (RANKL) in T lymphocytes: a potential role in multiple myeloma bone disease. Blood, 100: 4615-4621, 2002; Sebastien J. et al., The role of NFAT transcription factors in integrin-mediated carcinoma invasion. Nature cell biology, 4: 540-544, 2002; Klein, S. et al., Alpha 5 beta 1 integrin activates an NF-kappa B-dependent program of gene expression important for angiogenesis and inflammation. Mol Cell Biol, 22: 5912-5922, 2002).

Figure 3:
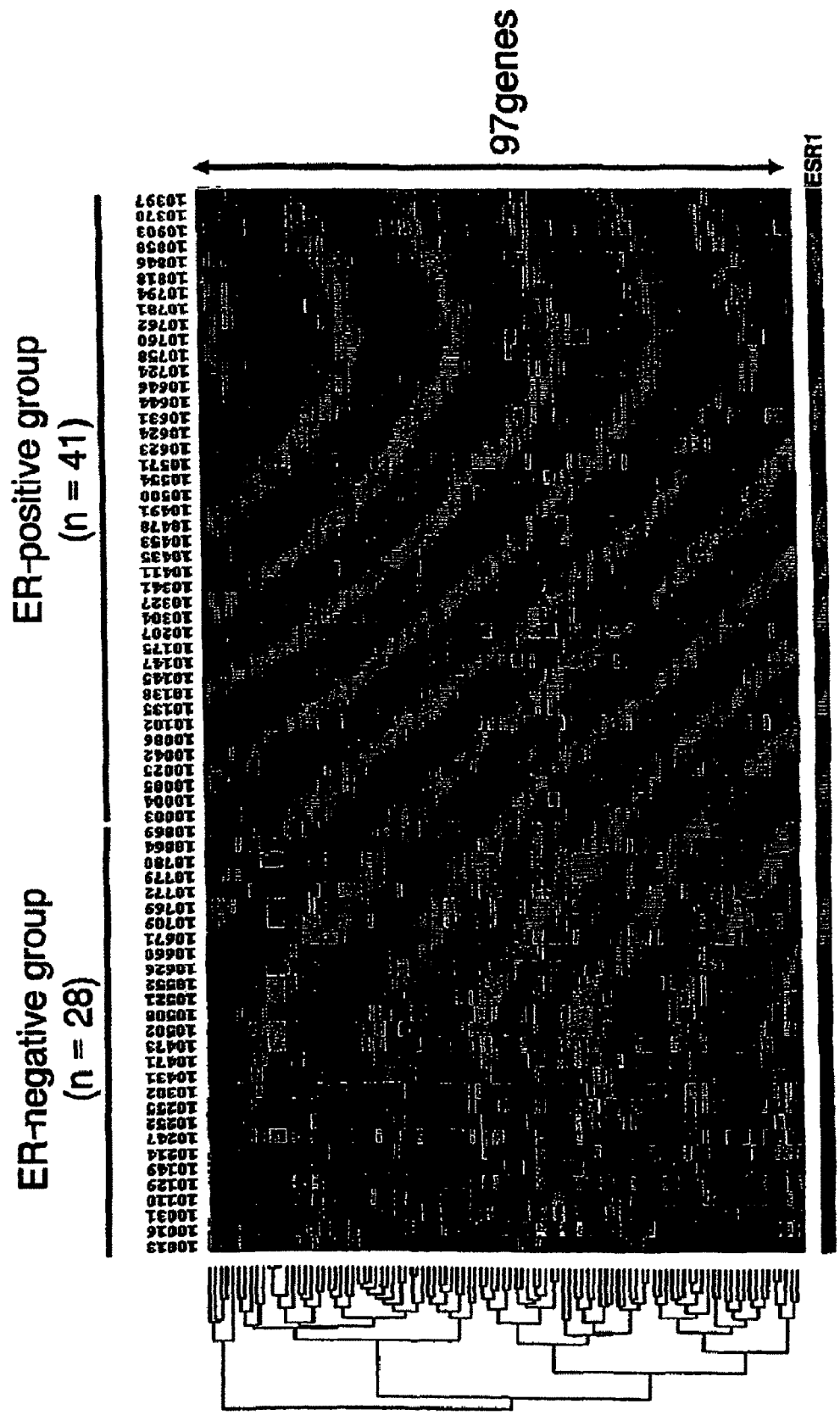
FIG. 3 depicts the supervised hierarchical clustering analysis of genes using 97 genes selected by a random-permutation test. In the horizontal row, 41 ER-positive samples and 28 ER-negative samples (selected from premenopausal patients) are shown. In the vertical column, 97 genes were clustered in different branches according to similarity in relative expression ratios. Genes in the lower main branch were preferentially expressed in a manner similar to the expression level of ESR1 as well as FIG. 2(A). Those in the upper branch were in inverse proportion of ESR1.

Next, a random permutation test was carried out to identify the genes that were differentially expressed in 41 ER-positive tumor and 28 ER-negative tumors in IDC. These all samples were from premenopausal patients. 97 genes that were able to distinguish between ER positive and negative with permutation P-value of less than 0.0001 were listed (see "Materials and Methods") (FIG. 3 and Table 2). Among them 96 genes were selected as BRC related genes of the present invention. Expression levels were increased for 92 of those genes and decreased for the other five in ER-positive group, as compared to the ER-negative group. Among these genes, GATA binding protein 3 (GATA3), trefoil factor 3 (TFF3), cyclin D1 (CCND1), MAPKK homolog (MAP2K4) and tissue inhibitor of metalloprotease 1 (TIMP1), insulin receptor substrate 1 (IRS1), X-box binding protein 1 (XBP1), GLI-Kruppel family member GLI3 (GLI3) were over-expressed in the ER-positives (Table 2). In addition, since estrogen receptor (ESR1) was rank-ordered at $6^{th}$ gene on the basis of magnitude of p-value (bottom panel in FIG. 3), it may be possible to distinguish breast cancers according to expression profiles of ER.

Figure 4:
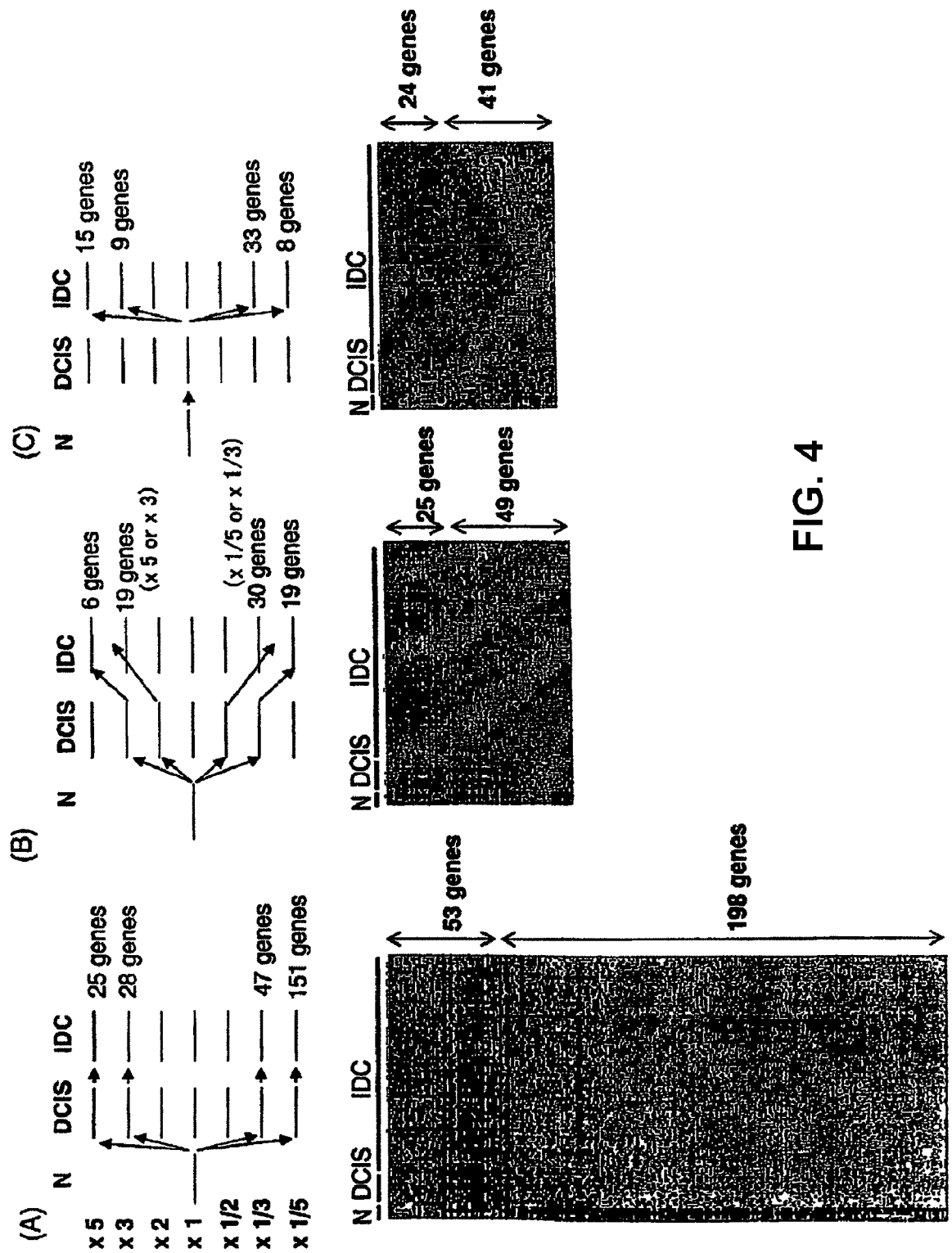
FIG. 4 depicts genes with altered expression in DCIS relative to normal duct and in IDC relative to DCIS.

Identification of Commonly Up- or Down-Regulated Genes in DCIS or IDC:

To further clarify mechanisms underlying carcinogenesis of breast cancer, genes commonly up- or down-regulated in DCIS and IDC were investigated, respectively. Gene expression profiles in 77 breast tumors (8 DCIS and 69 IDC premenopausal patients) identified 325 genes with commonly altered expression (FIG. 4A, 4B); 78 genes that were commonly up-regulated more than three-fold over their levels in normal breast ductal cells (FIG. 4A, 4B, Table 3, 5), whereas 247 genes whose expression were reduced to less than ⅓ in breast cancer cells (FIG. 4A, 4B, Table 4, 6). In particular, as shown in FIG. 4B, expression level of 25 genes was increased and that of 49 genes was decreased in transition from DCIS to IDC (Table 5 and 6). Among genes with elevated expression, fibronectin (FN1) which had already been reported as over-expressed in breast cancers (Mackay, A. et al., cDNA microarray analysis of genes associated with ERBB2 (HER2/neu) overexpression in human mammary luminal epithelial cells. Oncogene, 22: 2680-2688, 2003; Lalani, E. N. et al., Expression of the gene coding for a human mucin in mouse mammary tumor cells can affect their tumorigenicity. J Biol Chem, 266: 15420-15426, 1991; 22. Martin-Lluesma, S., et al., A. Role of Heel in spindle checkpoint signaling and kinetochore recruitment of Mad1/Mad2. Science, 297: 2267-2270, 2002.) was included (Table 4). On the other hand, among genes with decreased expression, ST5 and SCHIP1 which were known to function as tumor suppressor were also included (Table 6).

Next, genes with specifically altered expression exclusively in IDC were investigated. As a result, 24 up-regulated genes (FIG. 4C, Table 7) and 41 down-regulated genes (FIG. 4C, Table 8) were identified. Of the up-regulated genes, ERBB2, CCNB1, BUB1B were already known to be involved in carcinogenesis of breast cancers (Latta, E. K., et al., The role of HER2/neu overexpression/amplification in the progression of ductal carcinoma in situ to invasive carcinoma of the breast. Mod Pathol, 15: 1318-1325, 2002; Takeno, S., et al., Prognostic value of cyclin B1 in patients with esophageal squamous cell carcinoma. Cancer, 94: 2874-2881, 2002; Slamon, D. J., et al., Human breast cancer: correlation of relapse and survival with amplification of the HER-2/neu oncogene. Science, 235: 177-182, 1987). Of the down-regulated genes, AXUD1, a gene induced by AXIN, which was frequently down-regulated in lung, liver, colon and kidney cancers (Ishiguro, H., et al., Identification of AXUD1, a novel human gene induced by AXIN1 and its reduced expression in human carcinomas of the lung, liver, colon and kidney. Oncogene, 20: 5062-5066, 2001.) was included, suggesting that AXUD1 may also be involved in breast cancer carcinogenesis.

Figure 5:
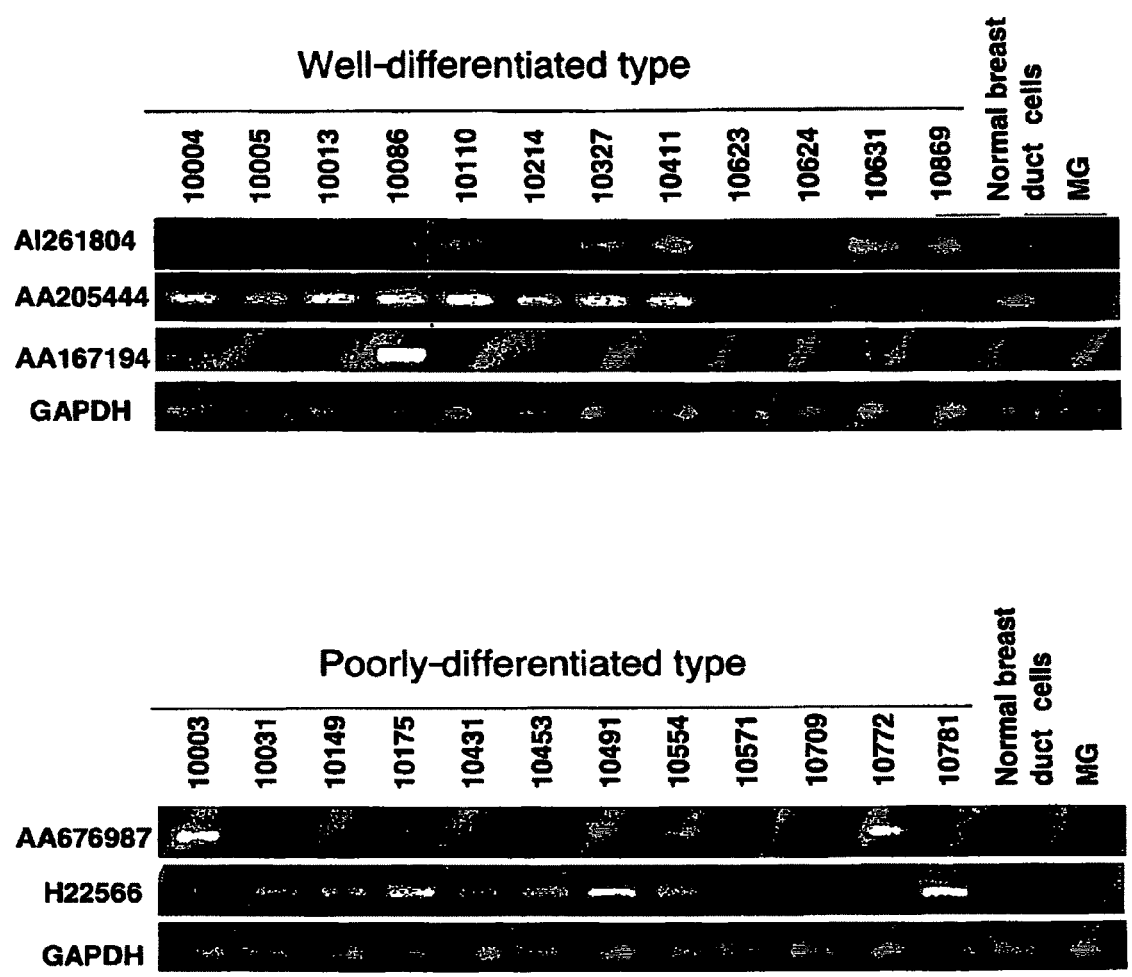
FIG. 5 depicts the results of semi-quantitative RT-PCR validation of highly expressed genes. Specifically, expression of 5 genes (AI261804, AA205444 and AA 167194 in well-differentiated 12 cases, and AA676987 and H22566 in poorly-differentiated 12 cases) and GAPDH (internal control) was examined by semi-quantitative RT-PCR. Signals of the microarray corresponded to the results of semi-quantitative RT-PCR experiments. Normal breast duct cells were prepared from normal ductal epithelial cells in premenopausal 15 patients used in this microarray. MG refers to whole human mammary gland.

Verification of Selected Genes by Semi-Quantitative RT-PCR:

To confirm the reliability of the expression data obtained by cDNA microarray analysis, semi-quantitative RT-PCR experiments were performed for 3 genes (Accession No. AI261804, AA205444, AA167194) that were highly up-regulated in informative cases with well-differentiated type, and 2 genes (AA676987 and H22566) that were also highly up-regulated in informative cases with poorly-differentiated type. The RT-PCR results were highly concordant with those of the microarray analysis in the great majority of the tested cases (FIG. 5, Table 9).

Figure 6:
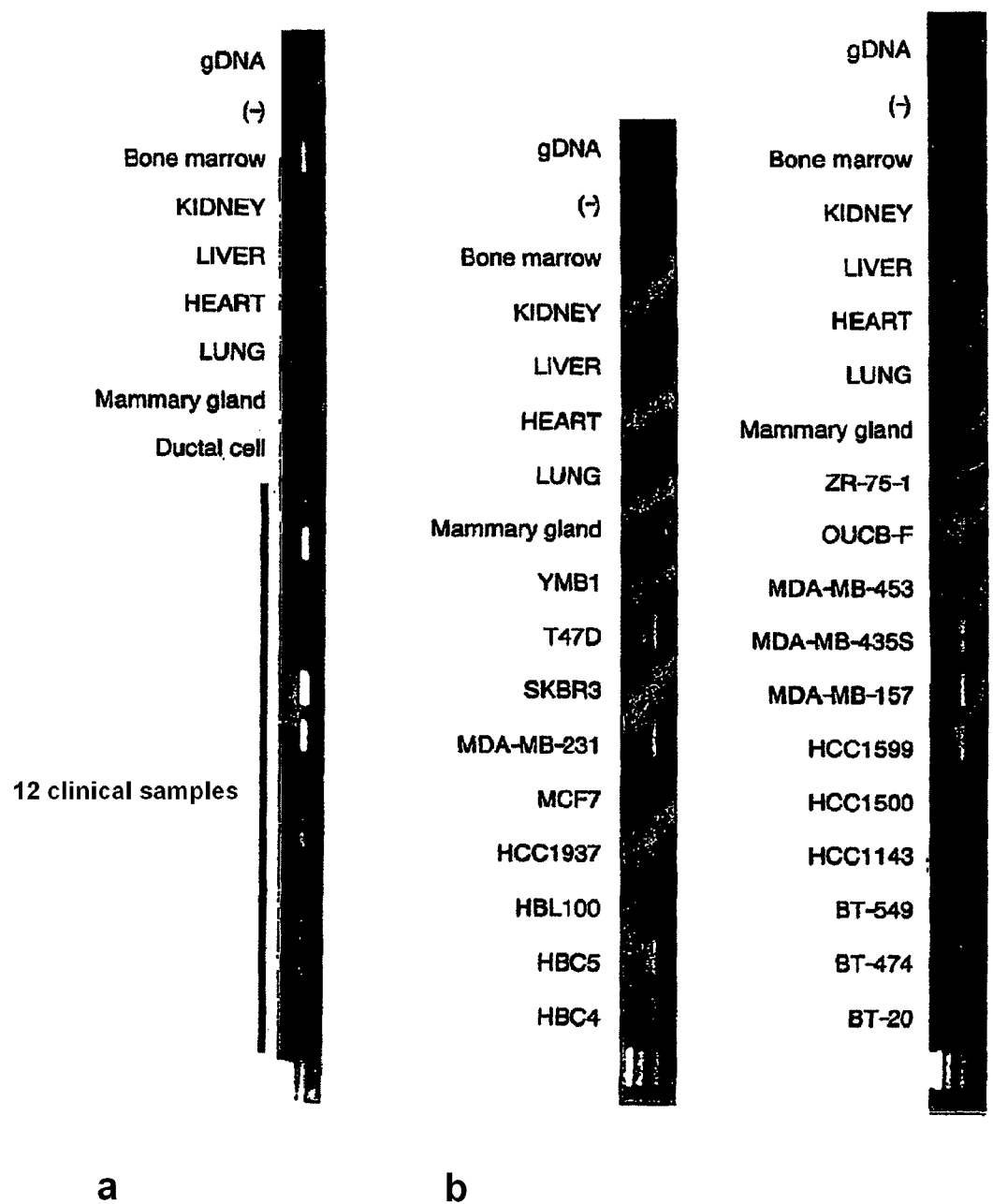
FIG. 6 depicts the results of semi-quantitative RT-PCR. Expression levels of A 7870 in tumor cells from (a) 12 breast cancer patients, (b) breast cancer cell lines (HBC4, HBC5, HBL100, HCC1937, MCF7, MDA-MB-231, SKBR3, T47D, YMB1, BT-20, BT-474, BT-549, HCC1143, HCC1500, HCC1599, MDA-MB-157, MDA-MB-435S, MDA-MB-453, OCUB-F and ZR-75-1), and normal human tissues are shown.
Figure 7:
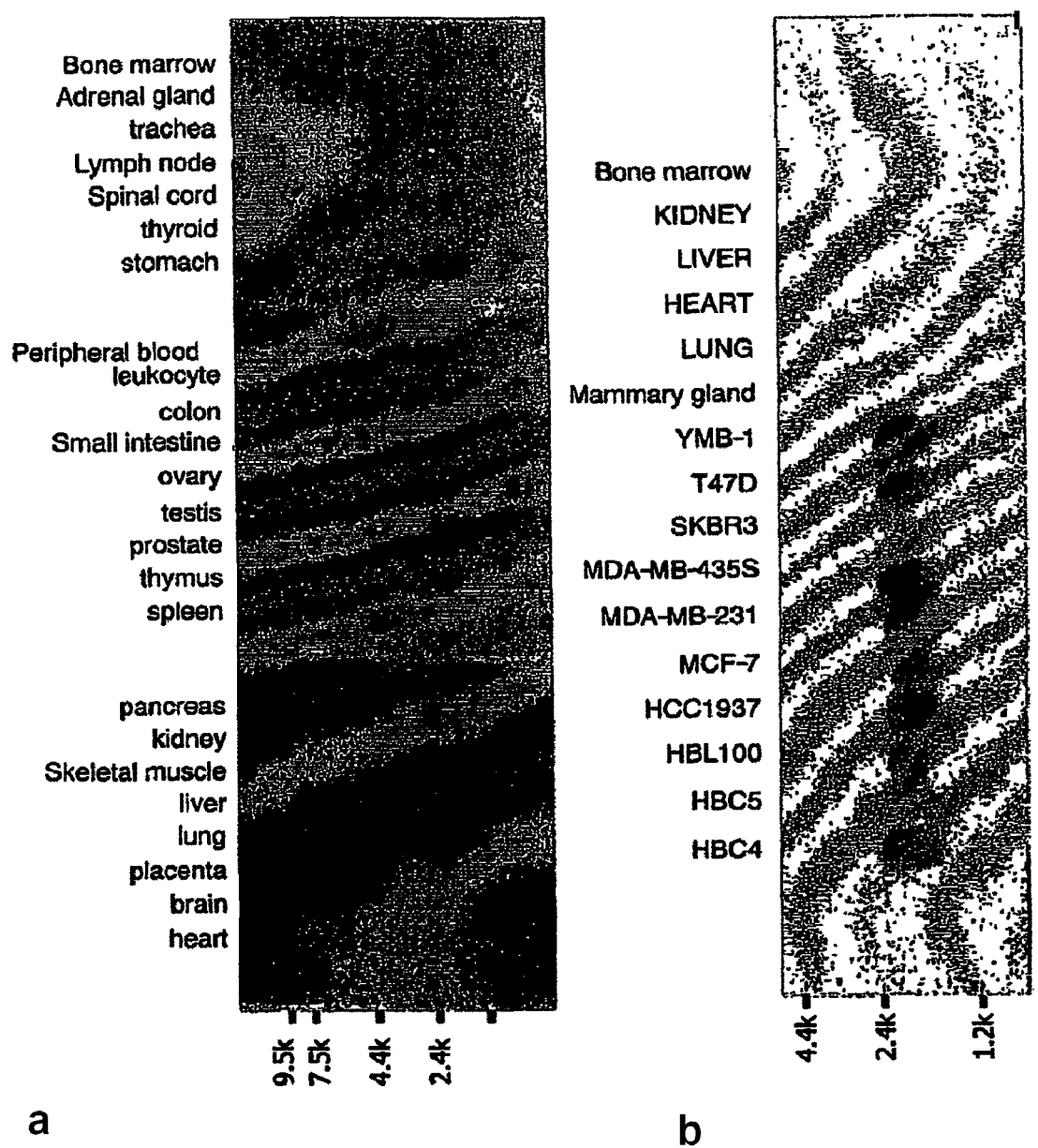
FIG. 7 depicts the results of Northern blot analysis of A7870 transcripts in (a) various human tissues, and (b) breast cancer cell lines and normal human vital organs.

Identification of A7870, Designed T-LAK Cell Originated Protein Kinase, as an Up-regulated Gene in Breast Cancer Cells We identified 24 genes that were up-regulated in IDC (table 7). Among them, we focused on A7870, designed to T-LAK cell originated protein kinase, TOPK (Genbank Accession, NM_018492) is located at chromosome 8p21.2 with a mRNA transcript 1899 bases in length consisting of 8 exons. Expression of A7870 was elevated in 30 of 39 (77%) breast cancer cases which were able to obtain expression data, especially in 29 of 36 (81%) cases with invasive ductal carcinoma specimens. To confirm the expression pattern of this gene in breast cancers, we performed semi-quantitative RT-PCR analysis using breast cancer cell lines and normal human tissues including normal breast cells. As a result, we found that A7870 whose expression showed the elevated expression in 7 of 12 clinical breast cancer specimens (well-differentiated type) compared to normal breast ductal cells and other normal tissues (FIG. 6a), and was overexpressed in 17 of 20 breast cancer cell lines (FIG. 6b). To further examine the expression pattern of this gene, we performed Northern blot analyses with multiple-human tissues and breast cancer cell lines using a cDNA fragment (320 bp) of A7870 as a probe (FIG. 7a). As a result, we observed that two transcripts (approximately 1.9 kb and 1.8 kb) were exclusively expressed in normal human testis and thymus. When we further examined the expression pattern of these transcripts with breast cancer-northern blot, we found that both transcripts were specifically overexpressed in breast cancer cell lines, compared to normal human tissues (FIG. 7b).

Isolation of Breast Cancer Specific-expressed Transcript of A7870.

Through the sequencing analysis of two transcript of A7870, since two variants of A7870 contain same open reading frame (ORF), we focused on TOPK, (Genbank accession number NM_018492), encodes a protein which is a serine/threonine kinase related to the dual specific mitogen-activated protein kinase kinase (MAPKK) family. SMART computer prediction shows TOPK contains pfam, pkinase motif in 32 to 320 residues, suggesting that this protein might involved in a signal transduction pathway that play a role in cell morphogenesis and cell growth.

Subcellular localization of A7870

Figures 1, 8:
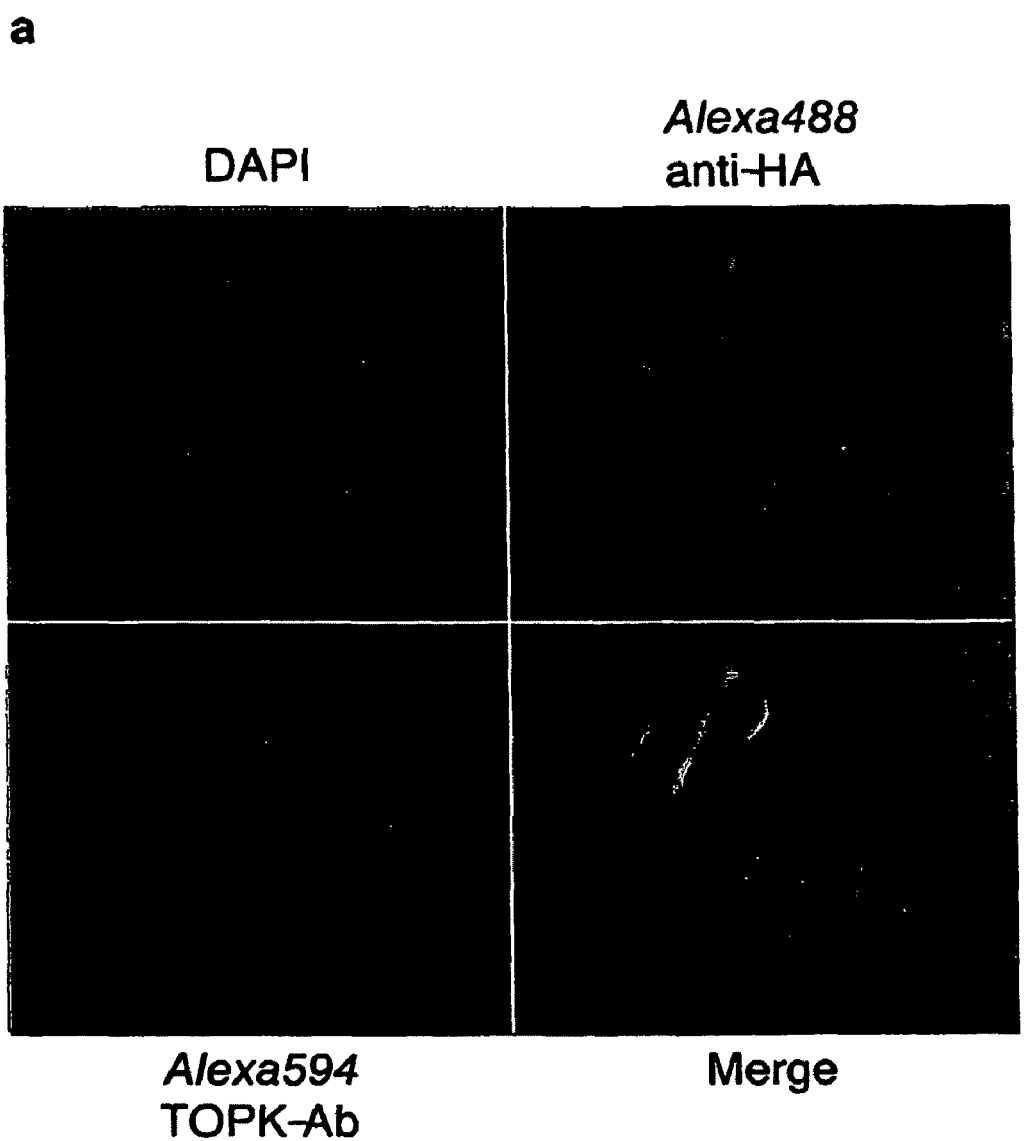
FIG. 8 depicts the subcellular localization of (a) exogenous A 7870 in transfected-COS7 cells and (b) exogenous A 7870 in T47D, BT-20 and HBC5 cells.
Figures 2, 8:
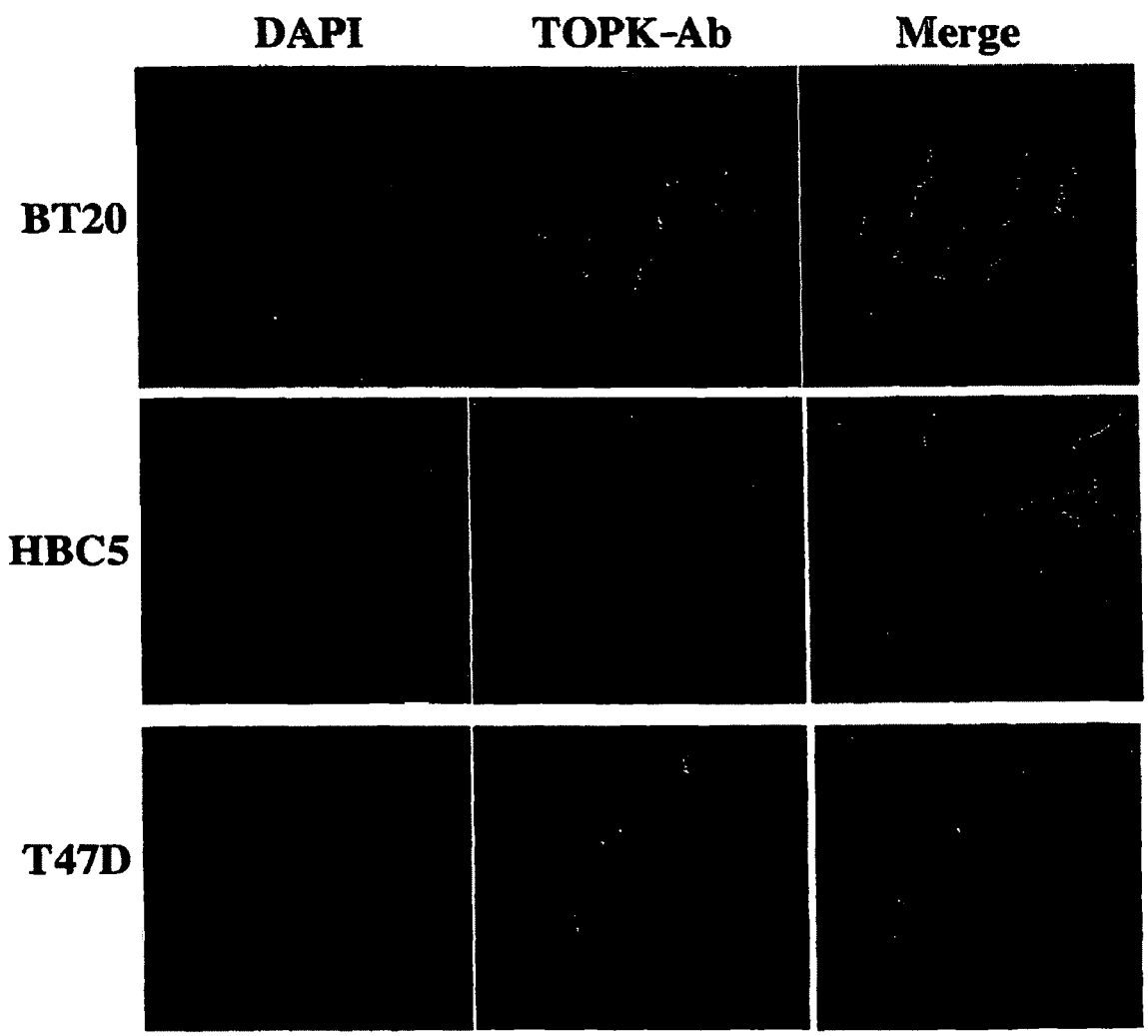

To further examine the characterization of A7870, we examined the sub-cellular localization of these gene products in mammalian cells. Firstly, when we transiently transfected plasmids expressing A7870 protein (pCAGGS-A7870-HA) into COS7 cells, immunocytochemical analysis with anti-HAtag antibody and TOPK polyclonal antibody reveals that exogenous A7870 protein localized to the cytoplasm and especially, strong signal around the nucleus membrane in all transfected-COS7 cells (FIG. 8a). Moreover, we examined the sub-cellular localization of endogenous protein with immunocytochemical staining using an anti-TOPK polyclonal antibody. Similarly, A7870 protein was also observed to be cytoplasmic apparatus and around nucleus in T47D, BT-20 and HBC5 cells (FIG. 8b).

Growth-inhibitory Effects of Small-interfering RNA (siRNA) Designed to Reduce Expression of A7870

To assess the growth-promoting role of A7870, we knocked down the expression of endogenous A7870 in breast cancer line T47D and BT-20, that have shown the overexpression of A7870, by means of the mammalian vector-based RNA interference (RNAi) technique (see Materials and Methods). We examined expression levels of A7870 by semi-quantitative RT-PCR experiments. A7870 (si1, si3 and si4)-specific siRNAs significantly suppressed expression, compared with control siRNA constructs (psiU6BX-LUC or -SC). To confirm the cell growth inhibition with A7870-specific siRNAs, we performed colony-formation and MTT assays, respectively. As a result, introduction of A7870 siRNA constructs suppressed growth of these breast cancer cells, consisting with the result of above reduced expression of this gene. Each result was verified by three independent experiments. Thus, our findings suggest that A7870 has a significant function in the cell growth of the breast cancer.

Figures 1, 2:
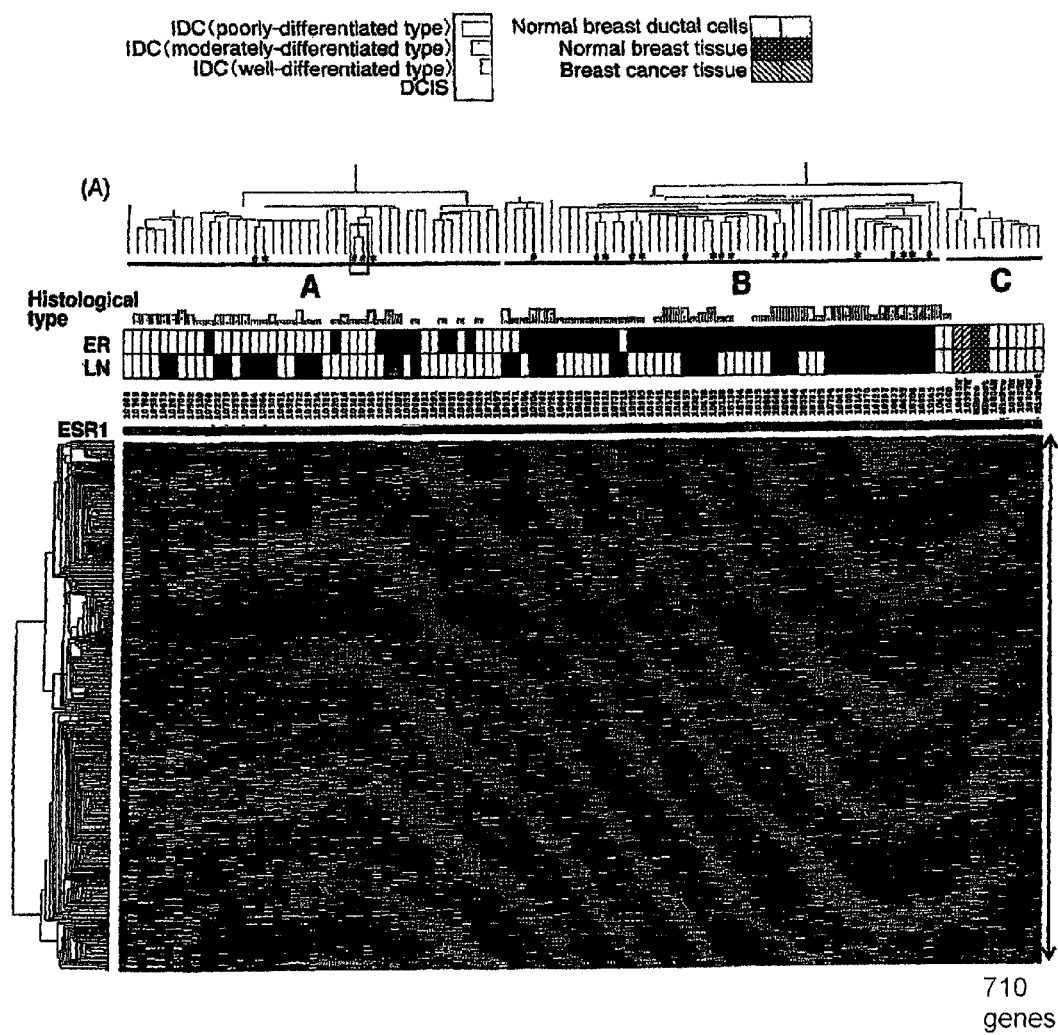
FIG. 2 depicts the results of unsupervised two-dimensional hierarchical clustering analysis of 710 genes across 102 samples.
Figure 2:
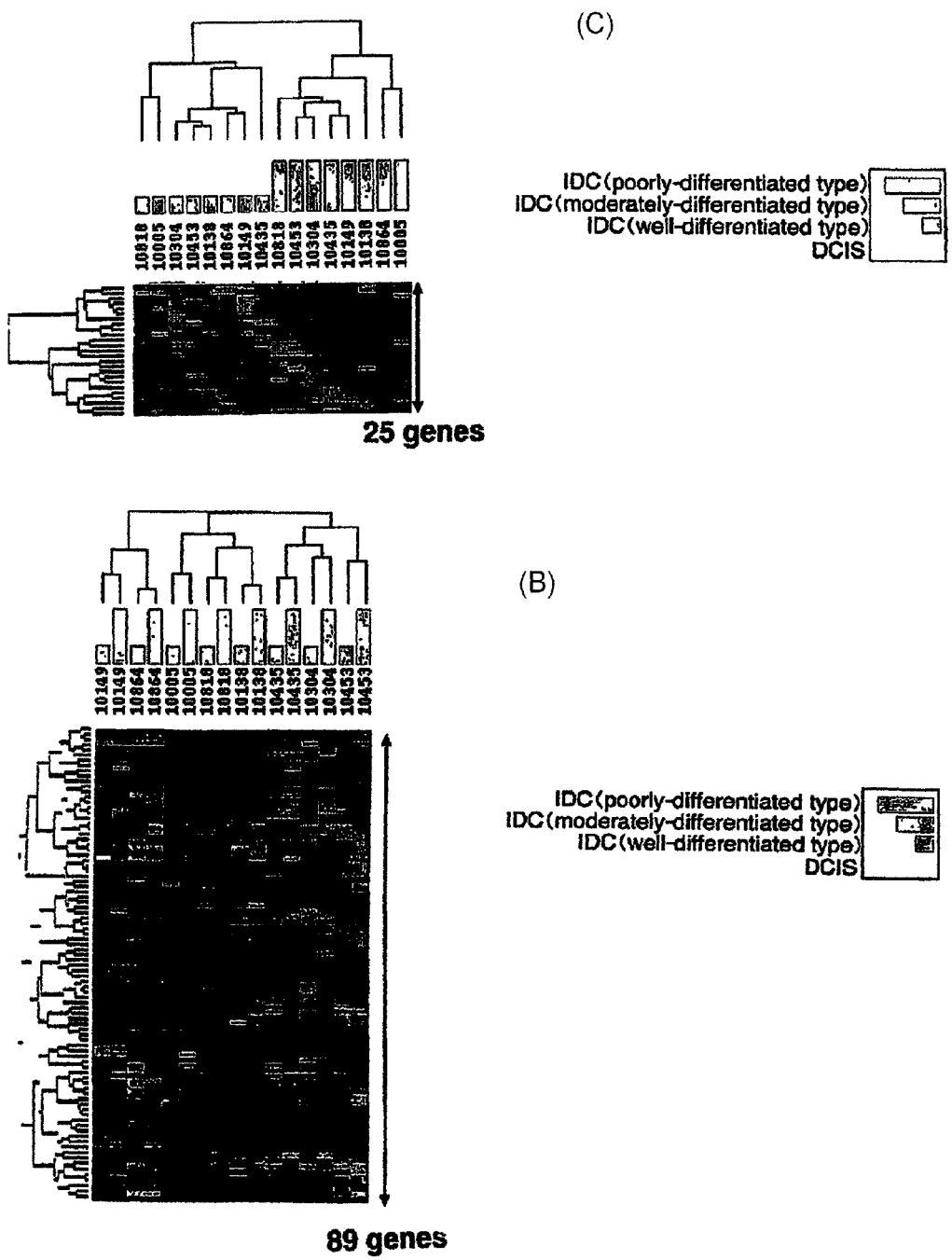
Figure 9:
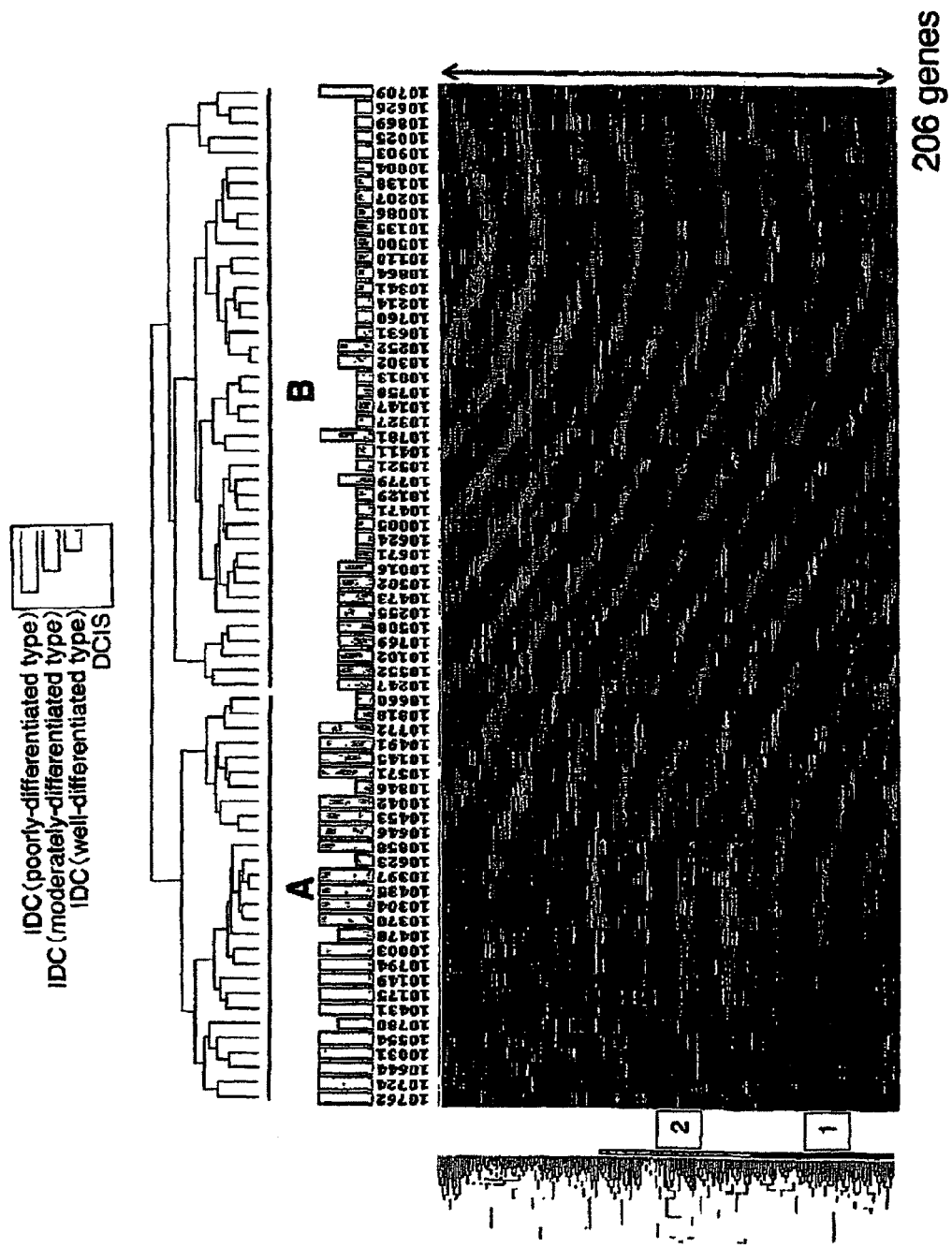
FIG. 9 depicts the supervised hierarchical clustering analysis of genes using 206 genes selected by a random-permutation test. In the horizontal row, 69 samples (selected from IDC patients) are depicted. In the vertical column, 97 genes were clustered in different branches according to similarity in relative expression ratios. Genes in the branch 1 and branch 2 were preferentially expressed similarly to the expression level of poorly-differentiated type and well-differentiated type.

Identification of Genes with Differentially Expressed in Histopathological Types, and Phenotypical Difference in Individual Patients:

One goal of the present invention was to discover consistently up- or down-regulated genes at different phenotype in some patients. However, since breast cancer shows heterogeneous and various phenotypes, histopathological differentiation by microscopy was not clearly discerned using unsupervised classification by gene expression patterns as shown in FIG. 2. To examine this observation more closely, a random-permutation test was performed and 206 genes that can distinguish between well-differentiated and poorly-differentiated cases were extracted. These 206 discriminating genes were all significant at the level of $P<0.01$ between 31 well- and 24 poorly-differentiated cancers (FIG. 9, Table 10). Two-dimensional hierarchical clustering analysis using these 206 genes was also able to classify the groups with regard to the distinct components of IDC (well-differentiated, moderately-differentiated and poorly-differentiated). Group A cluster contained genes with markedly increased expression in poorly-differentiated samples (branch 1 in the horizontal row); extracellular matrix structure (COL1A2, COL3A1 and P4HA2), cell adhesion (LOXL2, THBS2 and TAGLN2), whereas group B cluster contained the genes with increased expression primarily in well-differentiated and moderately-differentiated samples (branch 2 in the horizontal row); regulation of transcription (BTF, WTAP, HTATSF1), cell cycle regulator (CDC5L, CCT7). Two poorly-differentiated samples (sample #10709 and 10781) in group B, however, showed an expression pattern that was similar to well-differentiated signature rather than poorly-differentiated types. Some well-differentiated samples demonstrated co-expression of some genes that are characteristic of the poorly-differentiated signature.

Development of Predictive Scores for Lymph Node Metastasis:

In breast cancer, invasion into axillary lymph nodes is the most important prognostic factor (Shek, L. L. and Godolphin, W. Model for breast cancer survival: relative prognostic roles of axillary nodal status, TNM stage, estrogen receptor concentration, and tumor necrosis. Cancer Res, 48: 5565-5569, 1988). To develop an equation to achieve a scoring parameter for the prediction of axially lymph node metastasis using expression profiles of selected genes, the expression profiles of 20 node-positive cases and 20 node-negative cases were compared. Following the criteria described above, the 93 discriminating genes that showed permutation p-values of less than 0.0001 were first selected. Then, the top 34 genes in the candidate list that showed the best separation of node-positive from -negative cases were obtained (Table 11). As shown in FIG. 10A, a hierarchical clustering analysis using these 34 genes clearly classified all 40 breast cancer cases into one of two groups according to lymph-node status.

Finally, a predictive-scoring system that could clearly distinguish node-positive cases from node-negative cases using the expression profiles of the set of 34 genes was constructed. To further validate this scoring system, scores for 20 node-positive cases and 20 lymph node-negative cases that had not been among those used for construction of the scoring system, were calculated (see "Materials and Methods"). When 15.8 as a borderline score for 40 patients belonging to positive-metastasis group and negative were clearly separated (FIG. 10B) and scores of over 15.8 as "positive", and those of 15.8 or lower as "negative". To clarify the system further, the prediction score of metastasis from primary tumors, 17 node-positive cases and 20 negative cases who had not been part of the original procedure for selecting discrimination genes, were calculated. As shown in FIGS. 10B and 10C, among the 17 cases with lymph-node metastasis, all cases had positive scores according to the definition herein, whereas 18 (90%) of the 20 cases without lymph-node metastasis showed negative scores. 75 (97%) cases of 77 were placed correctly according to their lymph-node status, but two node-negative cases were misplaced or placed to the borderline or positive region.

Discussion

Breast cancer is a multifactor disease that develops as a result of interactions among genetic, environmental, and hormonal factors. Although distinct pathological stages of breast cancer have been described, the molecular differences among these stages are largely unknown (McGuire, W. L. Breast cancer prognostic factors: evaluation guidelines. J Natl Cancer Inst, 83: 154-155, 1991; Eifel, P., et al., National Institutes of Health Consensus Development Conference Statement: adjuvant therapy for breast cancer, Nov. 1-3, 2000. Natl Cancer Inst, 93: 979-989, 2001; Fisher, B., et al., Twenty-year follow-up of a randomized trial comparing total mastectomy, lumpectomy, and lumpectomy plus irradiation for the treatment of invasive breast cancer. N Engl J Med, 347: 1233-1241, 2002).

The development of genome-wide analysis of gene expression and laser microbeam microdissection (LMM) isolating pure cancerous cell populations of breast cancer enable the search for molecular-target genes having cancer-specific classification, treatment and outcome prediction in a variety of tumor types, especially in breast cancer.

Since, adipocytes account for more than 90% of mammary gland tissue, and epithelial cells in the organ, from which the carcinoma originates, correspond to a very small percentage, an analysis of gene-expression profiles using whole cancer tissues and normal whole mammary gland is significantly influenced by the particular mixture of cells in the tissues examined; proportional differences of adipocytes, fibroblasts, and inflammatory cells can mask significantly specific-expression of genes involved in breast carcinogenesis. Hence, an LMM system was used to purify as much as possible the populations of cancerous cells and normal epithelial cells obtained from surgical specimens (Hasegawa, S., et al. Genome-wide analysis of gene expression in intestinal-type gastric cancers using a complementary DNA microarray representing 23,040 genes. Cancer Res, 62: 7012-7017, 2002; Kitahara et al., and Tsunoda, T. Alterations of gene expression during colorectal carcinogenesis revealed by cDNA microarrays after laser-capture microdissection of tumor tissues and normal epithelia. Cancer Res, 61: 3544-3549, 2001; Kikuchi, T., et al. Expression profiles of non-small cell lung cancers on cDNA microarrays: identification of genes for prediction of lymph-node metastasis and sensitivity to anti-cancer drugs. Oncogene, 22: 2192-2205, 2003; Gjerdrum, L. M., et al., Laser-assisted microdissection of membrane-mounted paraffin sections for polymerase chain reaction analysis: identification of cell populations using immunohistochemistry and in situ hybridization. J Mol Diagn, 3: 105-110, 2001), (FIG. 1). To evaluate the purity of microdissected cell populations, expression of PLIN and FABP4, which are highly expressed in adipose tissue and mammary gland, was analyzed by gene expression profiles in 29 normal human tissues using a cDNA microarray (Saito-Hisaminato, A., et al., Genome-wide profiling of gene expression in 29 normal human tissues with a cDNA microarray. DNA Res, 9: 35-45, 2002). After the dissection procedure the proportion of contaminating adipocytes among the normal breast ductal epithelial cells was estimated to be smaller than 0.6%. In particular, when expression levels of PLIN were examined (Nishiu, J., et al., Isolation and chromosomal mapping of the human homolog of perilipin (PLIN), a rat adipose tissue-specific gene, by differential display method. Genomics, 48: 254-257, 1998), the purity of cell populations subjected to the LMM technique could therefore be approximately 100%. As shown in FIG. 2, unsupervised cluster analysis represented that breast cancer whole tissues were separated from microdissected breast cancer cells by LMM, whereas normal breast ductal cells and mammary glands were clustered in the same branch. Hence, to obtain accurately the breast cancer specific expression profile in some studies, it is essential to microdissect breast cancer cells and normal breast ductal epithelial cells from which breast cancer originates. The combined use of LMM and cDNA microarray analysis provides a powerful approach to elucidate precise molecular events surrounding the development and progression of breast cancer, and lead to the understanding of the mechanism of multistep carcinogenesis of breast cancer cells and tumor heterogeneneity.

As shown in FIG. 2A, through an unsupervised classification analysis on the basis of expression profiles, primary breast cancer can be divided into two groups and shown to associate with ER status by EIA. It was discovered that ER+ and ER− tumors display very different gene expression phenotypes. This result suggests that these two histologically distinct lesions have different biological natures that may play an important role in carcinogenesis of breast cancer, and further suggests that ER status can be used to establish the necessity of hormone therapy in the adjuvant setting (Eifel, P., et al National Institutes of Health Consensus Development Conference Statement: adjuvant therapy for breast cancer, Nov. 1-3, 2000. J Natl Cancer Inst, 93: 979-989, 2001; Hartge, P. Genes, hormones, and pathways to breast cancer. N Engl J Med, 348: 2352-2354, 2003). In addition, through supervised statistical analysis, a subset of genes that were able to separate ER-positive from ER-negative to investigate hormone dependent progression were selected and novel molecular-target for anti-cancer drug were explored. 97 genes whose expression is significantly different between these two groups consisting of premenopausal patients were identified by a random permutation test (FIG. 3). Among these genes, MAP2K4, which is a centrally-placed mediator of the SAPK pathways, was included. Cyclin D1, a gene that is strongly associated with ER expression in breast cancer in this and other studies (May, F. E. and Westley, B. R. Expression of human intestinal trefoil factor in malignant cells and its regulation by oestrogen in breast cancer cells. J Pathol, 182: 404-413, 1997), was also included. Estrogens are important regulators of growth and differentiation in the normal mammary gland and are also important in the development and progression of breast carcinoma (Shek, L. L. and Godolphin, W. Model for breast cancer survival: relative prognostic roles of axillary nodal status, TNM stage, estrogen receptor concentration, and tumor necrosis. Cancer Res, 48: 5565-5569, 1988). Estrogens regulate gene expression via ER; however, the details of the estrogen effect on downstream gene targets, the role of cofactors, and cross-talk between other signaling pathways are far from fully understood. As approximately two-thirds of all breast cancers are ER+ at the time of diagnosis, the expression of the receptor has important implications for their biology and therapy. Since recently novel selective estrogen receptor modulators (SERMs) have been developing as hormonal treatment against ER-positive breast cancer patients, these genes associated with ER status might be novel potential molecular-targets for SERMs (Smith, I. E. and Dowsett, M. Aromatase inhibitors in breast cancer. N Engl J Med, 348: 2431-2442, 2003). These findings suggest that the comparison of expression profiles and ER-status provides useful information to elucidate the hormonal regulation of cell proliferation and progression of ER-independent breast cancer cells.

The development and use of molecular-based therapy for breast cancer and other human malignancies requires a detailed molecular genetic analysis of patient tissues. Histological evidence suggests that several pre-neoplastic states exist that precede invasive breast tumors. These histological lesions include atypical ductal hyperplasia, atypical lobular hyperplasia, ductal carcinoma in situ (DCIS), and lobular carcinoma in situ (Lakhani, S. R. The transition from hyperplasia to invasive carcinoma of the breast. J Pathol, 187: 272-278, 1999). These lesions are thought to fall on a histological continuum between normal breast epithelium or the terminal duct lobular units from which breast cancers arise, and the final invasive breast cancer. Several models have been proposed to explain the genetic abnormalities between pre-neoplasia and neoplasia.

Various genes that showed commonly increased or decreased expression among the pathologically discrete stages, such as comparison of between DCIS and IDC, were observed, resulting in total identification of 325 genes. These genes may underlie the molecular basis of the pathological grade for breast cancer, and expression levels of these genes were correlated with advanced tumor grade. 78 commonly up-regulated genes (Table 3, 5) and 247 commonly down-regulated genes (Table 4, 6) in DCIS and IDC were also identified. Among up-regulated genes, NAT1, HEC, GATA3 and RAI3, which have been reported to be over-expressed in breast cancer, were noted as potentially expressed in preinvasive stages (Geylan, Y. S., et al., Arylamine N-acetyltransferase activities in human breast cancer tissues.

Neoplasma, 48: 108-111, 2001; Chen, Y., et al., HEC, a novel nuclear protein rich in leucine heptad repeats specifically involved in mitosis. Mol Cell Biol, 17: 6049-6056, 1997; Bertucci, F., et al., Gene expression profiling of primary breast carcinomas using arrays of candidate genes. Hum Mol Genet, 9: 2981-2991, 2000; Cheng, Y. and Lotan, R. Molecular cloning and characterization of a novel retinoic acid-inducible gene that encodes a putative G protein-coupled receptor. J Biol Chem, 273: 35008-35015, 1998). On the other hand, TGFBR2, included as a down-regulated gene in the present invention, is known to lead to reduced malignancy (Sun, L., et al., Expression of transforming growth factor beta type II receptor leads to reduced malignancy in human breast cancer MCF-7 cells. J Biol Chem, 269: 26449-26455, 1994). These findings suggest that these genes may be involved in transition from DCIS to IDC.

In particular, 25 up-regulated genes (Table 5) and 49 down-regulated genes (Table 6) were identified with elevated or decreased expression according to transition from DCIS to IDC. The list of up-regulated elements included genes encoding transcriptional factors and proteins involved in the signal transduction pathway, and in the cell cycle, and that play an important role in invasive tumorigenesis. Over-expression of FoxM1 and cyclin B1 have been reported in various tumour types. Over-expression of FoxM1 stimulates cyclin B1 expression (Leung T W, 2001). CCNB1 is a cell cycle control protein that is required for passage through G2 and mitosis (Pines, J. and Hunter, T. Cyclins A and B1 in the human cell cycle. Ciba Found Symp, 170: 187-196; discussion 196-204, 1992). TOP2A inhibitors are widely used as chemotherapeutic agents in lung cancer treatment (Miettinen, H. E., et al., High topoisomerase II alpha expression associates with high proliferation rate and poor prognosis in oligodendrogliomas. Neuropathol Appl Neurobiol, 26: 504-512, 2000). BUB1B may be responsible for a chromosomal instability phenotype contributing to tumor progression in mitotic checkpoint and genetic instability (Bardelli, A., et al. Carcinogen-specific induction of genetic instability. Proc Natl Acad Sci USA, 98: 5770-5775, 2001). MMP11, its expression was shown to have a direct negative effect on patients' survival (Boulay, A., et al. High cancer cell death in syngeneic tumors developed in host mice deficient for the stromelysin-3 matrix metalloproteinase. Cancer Res, 61: 2189-2193, 2001). ECM1 has angiogenic properties and is expressed by breast tumor cells (Han, Z., et al., Extracellular matrix protein 1 (ECM1) has angiogenic properties and is expressed by breast tumor cells. Faseb J, 15: 988-994, 2001). Although the most of these functions are still unknown, evaluation of the functional analysis of these genes may indicate that these play a role in mediating invasive activity.

In this report, through the precise expression profiles of breast cancer by means of genome wide cDNA microarray, we isolated novel genes, A7870 that were significantly over-expressed in breast cancer cells, compared to normal human tissues. Furthermore, we demonstrated treatment of breast cancer cells with siRNA effectively inhibited expression of target gene, A7870 and significantly suppressed cell/tumor growth of breast cancer. These findings suggest that A7870 might play key roles in tumor cell growth proliferation, and might be promising targets for development of anti-cancer drugs.

A7870, designed to TOPK, a new member of the MAPKK family, is selected for study as its significant elevated-expression in breast cancer. We identified the approximately 1.8 and 1.9 kb transcripts showed cancer specific expression. These transcripts have different sequence of 5' UTR, but same ORF. We demonstrated treatment of breast cancer cells with siRNA effectively inhibited expression of A7870 and significantly suppressed cell/tumor growth of breast cancer. These findings suggest that A7870 might play key roles in tumor cell growth proliferation, and might be promising targets for development of anti-cancer drugs.

The ability of some criteria to predict disease progression and clinical outcome is, however, imperfect. Patients with more aggressive disease can benefit from adjuvant chemotherapy or hormone therapy and are currently identified according to a combination of criteria: age, the size of the tumor, axillary-node status, the histologic type and pathological grade of cancer, and hormone-receptor status. Histologically different tumors were classified by subset of genes, a process that provides pathologically relevant information. Most investigators have suggested that patients have a poorer prognosis if the tumor showed a significantly higher percentage of poorly differentiated histology.

A surprising result from this study was the remarkable similarity in the expression profiles of different histological type in each patient. Through microdissection and global gene expression analysis, changes in gene expression associated with invasion and prognosis were examined using mRNA expression profiles from breast cancer cells at well-differentiated type and poorly differentiated type using supervised analysis. Through an unsupervised classification analysis on the basis of expression profiles, breast cancer can be divided into two groups and shown to associate with different pathologically lesions. 25 genes whose expression is significantly different between these two groups consisting of each patient were identified by a random permutation test (FIG. 2C). Among these genes, nuclear factor of activated T-cells 5 (NFAT5) is restricted to promoting carcinoma cell migration, which highlights the possibility of distinct genes that are induced by these transcription factors (Sebastien J. et al., The role of NFAT transcription factors in integrin-mediated carcinoma invasion. Nature cell biology, 4: 540-544, 2002). Thrombospondin 2 (THSB2) is extracellular matrix proteins that appears to play a role in cell adhesion and cell migration. One important advantage of the LMM-based approach is the ability to select cancer cells of different phenotypes from the one specimen. Systematic analysis of gene-expression patterns provides a window on the biology and pathogenesis of invasion.

Furthermore, lymph-node metastasis is a critical step in tumor progression and one of the major component of poor prognosis in breast cancer patients (Shek, L. L. and Godolphin, W. Model for breast cancer survival: relative prognostic roles of axillary nodal status, TNM stage, estrogen receptor concentration, and tumor necrosis. Cancer Res, 48: 5565-5569, 1988), but only a minority of patients exhibits clinically detectable metastases at diagnosis. Lymph-node status at diagnosis is the most important measure for future recurrence and overall survival, it is a surrogate that is imperfect at best. About a third of patients with no detectable lymph-node involvement, for example, will develop recurrent disease within 10 years (Saphner, T., et al., Annual hazard rates of recurrence for breast cancer after primary therapy. J Clin Oncol, 14: 2738-2746, 1996). Sentinel lymph node biopsy was shown to be an accurate procedure in the study of axillary lymph nodes; it allowed a marked decrease in surgery-related morbidity of breast cancer and axillary dissection could be avoided. Other parameters, such as nuclear grading, patient age, tumor size, are not able to predict the axillary lymph node status, and it is not possible to effectively diagnose lymph node status by sentinel lymph node biopsy. Therefore, the present identification of a subset of genes differentially expressed between node-positive and node-negative tumors can contribute to improve clinical diagnosis and understanding of the precise biophysical events. Cluster analysis (FIG. 10) suggested to separate cases with lymph-node metastasis from those without metastasis. The genes that contributed to separation of the two patient groups according to the status of lymph-node metastasis may serve as molecular markers for metastasis (Ramaswamy, S., et al., A molecular signature of metastasis in primary solid tumors. Nat Genet, 33: 49-54, 2003). For example, among these 34 genes, FUS which is known as TLS for translocated in liposarcoma, is decreased in node-negative cancers, is translocated with the gene encoding the transcription factor ERG-1 in human myeloid leukaemias. One of the important functions of wild-type FUS is genome maintenance, particularly the maintenance of genomic stability (Hicks, G. G., et al., Fus deficiency in mice results in defective B-lymphocyte development and activation, high levels of chromosomal instability and perinatal death. Nat Genet, 24: 175-179, 2000). Expression levels were increased for some of the genes in the metastasis-positive group as compared to the negative group. For example, regarding EEF1D, the higher expression of EF-1 delta in the tumours suggested that malignant transformation in vivo requires an increase in translation factor mRNA and protein synthesis for entry into and transition through the cell cycle. CFL1, Rho protein signal transduction, and Rho family GTPases regulate the cytoskeleton and cell migration and are frequently overexpressed in tumours (Yoshizaki, H., et al., Activity of Rho-family GTPases during cell division as visualized with FRET-based probes. J Cell Biol, 162: 223-232, 2003; Arthur, W. T., et al., Regulation of Rho family GTPases by cell-cell and cell-matrix adhesion. Biol Res, 35: 239-246, 2002). BRAF, the B-Raf kinase, was shown to be capable of phosphorylating and activating MEK as a result of growth factor stimulation. Although the function of some of these genes is still unknown, understanding the function of these gene products may clarify their roles in metastasis in breast cancer.

The causes and clinical course of recurrence are presently unknown. Furthermore, it is not possible to predict outcome reliably on the basis of available clinical, pathological, and genetic markers. Although it is believed that the predicting score system of the present invention, using the expression profiles of these 34 genes, may be useful for improvement of prognosis, verification using a larger number of cases may be needed for introduction into clinical stages. In any event, the present invention appears to provide precise information about the biological nature of cancer cells that have been misunderstood by conventional histological diagnosis.

Cancer therapies directed at specific molecular alterations that occur in cancer cells have been validated through clinical development and regulatory approval of anti-cancer drugs such as trastuzumab (Herceptin) for the treatment of advanced breast cancer (Coussens, L., et al. Tyrosine kinase receptor with extensive homology to EGF receptor shares chromosomal location with neu oncogene. Science, 230: 1132-1139, 1985). This drug is clinically effective and better tolerated than traditional anti-cancer agents because it targets only transformed cells. Hence, this drug not only improves survival and quality of life for cancer patients, but also validates the concept of molecularly targeted cancer therapy. Furthermore, targeted drugs can enhance the efficacy of standard chemotherapy when used in combination therewith (Gianni, L. and Grasselli, G. Targeting the epidermal growth factor receptor a new strategy in cancer treatment. Suppl Tumori, 1: S60-61, 2002; Klejman, A., et al., Phosphatidylinositol-3 kinase inhibitors enhance the anti-leukemia effect of STI571. Oncogene, 21: 5868-5876, 2002). Therefore, future cancer treatments will probably involve combining conventional drugs with target-specific agents aimed at different characteristics of tumor cells such as angiogenesis and invasiveness. Furthermore, the present invention demonstrates that the novel tumor markers, substances that may be present in abnormal amounts in the blood, or nipple aspirates of a woman who has breast cancer, may be reliable enough to be used routinely to detect early breast cancer.

Currently, no effective treatment is available for patients in advanced breast cancer. Thus, new therapeutic approaches and tailor-made treatment are urgently required. The cancer-specific expression profiles of the present invention, including up- and down-regulated genes in breast cancers, should provide useful information for identifying molecular targets for the treatment of patents.

TABLE 1

List of genes with altered expression between well and poorly differentiated type in histological phenotype

| BRC NO. | ACCESSION NO. | Symbol | TITLE | p-value |
|---|---|---|---|---|
| 1 | AF053712 | TNFSF11 | tumor necrosis factor (ligand) superfamily, member 11 | 1.2E−06 |
| 2 | BF973104 | LOC201725 | hypothetical protein LOC201725 | 3.2E−05 |
| 3 | AV752313 | KPNA6 | karyopherin alpha 6 (importin alpha 7) | 1.1E−04 |
| 4 | AK026898 | FOXP1 | forkhead box P1 | 7.4E−04 |
| 5 | AA148107 | ITGA5 | integrin, alpha 5 (fibronectin receptor, alpha polypeptide) | 7.9E−04 |
| 6 | AK001067 | NFAT5 | nuclear factor of activated T-cells 5, tonicity-responsive | 8.2E−04 |
| 7 | AB007919 | KIAA0450 | KIAA0450 gene product | 1.8E−03 |
| 8 | BG026429 | SFRS2 | splicing factor, arginine/serine-rich 2 | 2.0E−03 |
| 9 | M87770 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | 2.1E−03 |
| 10 | L02785 | SLC26A3 | solute carrier family 26, member 3 | 2.7E−03 |
| 11 | BF037402 | | *Homo sapiens*, clone MGC: 17296 IMAGE: 3460701, mRNA, complete cds | 2.8E−03 |
| 12 | L12350 | THBS2 | thrombospondin 2 | 2.8E−03 |
| 13 | N36875 | | *Homo sapiens*, clone IMAGE: 4994678, mRNA | 3.8E−03 |
| 14 | AL135342 | | ESTs, Weakly similar to neuronal thread protein [*Homo sapiens*] [*H. sapiens*] | 4.3E−03 |
| 15 | AL049426 | SDC3 | syndecan 3 (N-syndecan) | 4.5E−03 |
| 16 | AW961424 | KIAA1870 | KIAA1870 protein | 5.2E−03 |
| 17 | AA523117 | DC-TM4F2 | tetraspanin similar to TM4SF9 | 5.5E−03 |
| 18 | Z11531 | EEF1G | eukaryotic translation elongation factor 1 gamma | 6.1E−03 |
| 19 | AI423028 | SMARCD3 | SWI/SNF related, matrix associated, actin dependent regulator of chromatin, subfamily d, member 3 | 6.8E−03 |
| 20 | AB002391 | MN7 | D15F37 (pseudogene) | 7.1E−03 |
| 21 | D32050 | AARS | alanyl-tRNA synthetase | 7.2E−03 |
| 22 | BE876949 | RAB7 | RAB7, member RAS oncogene family | 7.9E−03 |
| 23 | AW291083 | | ESTs | 8.0E−03 |
| 24 | AI568910 | | ESTs | 8.2E−03 |
| 25 | AK023480 | SRP72 | signal recognition particle 72 kDa | 8.7E−03 |

TABLE 2

List of genes with altered expression between ER-positive and ER-negative tumors

| BRC NO. | ACCESSION NO. | Symbol | TITLE | p-value |
|---|---|---|---|---|
| 26 | AW949747 | GATA3 | GATA binding protein 3 | 3.2E−20 |
| 27 | BE868254 | ESTs | ESTs | 2.2E−14 |
| 28 | AF037335 | CA12 | carbonic anhydrase XII | 1.6E−13 |
| 29 | BF724977 | ASB13 | ankyrin repeat and SOCS box-containing 13 | 8.5E−13 |
| 30 | NM_004636 | SEMA3B | sema domain, immunoglobulin domain (Ig), short basic domain, secreted, (semaphorin) 3B | 9.7E−13 |
| 31 | NM_000125 | ESR1 | estrogen receptor 1 | 1.2E−12 |
| 32 | M73554 | CCND1 | cyclin D1 (PRAD1: parathyroid adenomatosis 1) | 3.9E−12 |
| 33 | NM_005544 | IRS1 | insulin receptor substrate 1 | 4.4E−12 |
| 34 | M14745 | BCL2 | B-cell CLL/lymphoma 2 | 5.1E−12 |
| 35 | BE826171 | BCMP11 | breast cancer membrane protein 11 | 2.8E−11 |
| 36 | AI087270 | SIAH2 | seven in absentia homolog 2 (*Drosophila*) | 2.8E−11 |
| 37 | L07033 | HMGCL | 3-hydroxymethyl-3-methylglutaryl-Coenzyme A lyase (hydroxymethylglutaricaciduria) | 2.8E−11 |
| 38 | AB014523 | ULK2 | unc-51-like kinase 2 (*C. elegans*) | 4.0E−11 |
| 39 | AL137588 | DKFZp434K1210 | hypothetical protein DKFZp434K1210 | 5.2E−11 |

TABLE 2-continued

List of genes with altered expression between ER-positive and ER-negative tumors

| BRC NO. | ACCESSION NO. | Symbol | TITLE | p-value |
|---|---|---|---|---|
| 40 | AL137566 | EST | *Homo sapiens* mRNA; cDNA DKFZp586G0321 (from clone DKFZp586G0321) | 5.4E−11 |
| 41 | AF038421 | GFRA1 | GDNF family receptor alpha 1 | 8.4E−11 |
| 42 | AI194045 | FE65L2 | FE65-like protein 2 | 9.2E−11 |
| 43 | BG163478 | ESTs | ESTs, Weakly similar to BAI1_HUMAN Brain-specific angiogenesis inhibitor 1 precursor [*H. sapiens*] | 1.1E−10 |
| 44 | M31627 | XBP1 | X-box binding protein 1 | 1.1E−10 |
|  | AA156269 | EST | *Homo sapiens*, clone IMAGE: 4794107, mRNA | 1.3E−10 |
| 46 | NM_006763 | BTG2 | BTG family, member 2 | 1.9E−10 |
| 47 | AW504052 | SEC15L | SEC15 (*S. cerevisiae*)-like | 2.1E−10 |
| 48 | NM_005400 | PRKCE | protein kinase C, epsilon | 2.3E−10 |
| 49 | AI628151 | XBP1 | X-box binding protein 1 | 2.7E−10 |
| 50 | AF043045 | FLNB | filamin B, beta (actin binding protein 278) | 3.5E−10 |
| 51 | U31383 | GNG10 | guanine nucleotide binding protein (G protein), gamma 10 | 4.6E−10 |
| 52 | L10333 | RTN1 | reticulon 1 | 5.6E−10 |
| 53 | AK025099 | SIGIRR | single Ig IL-1R-related molecule | 6.2E−10 |
| 54 | AL039253 | LIV-1 | LIV-1 protein, estrogen regulated | 7.4E−10 |
| 55 | AW949662 | KIAA0239 | KIAA0239 protein | 8.0E−10 |
| 56 | D13629 | KTN1 | kinectin 1 (kinesin receptor) | 1.5E−09 |
| 57 | NM_000165 | GJA1 | gap junction protein, alpha 1, 43 kDa (connexin 43) | 1.5E−09 |
| 58 | AA533079 | C1orf21 | chromosome 1 open reading frame 21 | 1.8E−09 |
| 59 | AF251056 | CAPS2 | calcyphosphine 2 | 1.9E−09 |
| 60 | AF061016 | UGDH | UDP-glucose dehydrogenase | 2.0E−09 |
| 61 | U92544 | MAGED2 | melanoma antigen, family D, 2 | 2.1E−09 |
| 62 | BE617536 | RPL13A | ribosomal protein L13a | 2.4E−09 |
| 63 | AK024102 | MYST1 | MYST histone acetyltransferase 1 | 2.5E−09 |
| 64 | BF212902 | EST | *Homo sapiens* mRNA; cDNA DKFZp564F053 (from clone DKFZp564F053) | 2.8E−09 |
| 65 | AK025480 | FLJ21827 | hypothetical protein FLJ21827 | 3.0E−09 |
| 66 | AI376713 | ESTs | ESTs, Weakly similar to hypothetical protein FLJ20378 [*Homo sapiens*] [*H. sapiens*] | 3.6E−09 |
| 67 | AI028483 | ESTs | ESTs | 3.8E−09 |
| 68 | AK022249 | EST | *Homo sapiens* cDNA FLJ12187 fis, clone MAMMA1000831. | 4.2E−09 |
| 69 | AI568527 | EST | *Homo sapiens* cDNA FLJ34849 fis, clone NT2NE2011687. | 5.0E−09 |
| 70 | AL133074 | TP53INP1 | tumor protein p53 inducible nuclear protein 1 | 5.3E−09 |
| 71 | AF022116 | PRKAB1 | protein kinase, AMP-activated, beta 1 non-catalytic subunit | 6.1E−09 |
| 72 | AF007170 | C1orf34 | chromosome 1 open reading frame 34 | 9.7E−09 |
| 73 | AF042081 | SH3BGRL | SH3 domain binding glutamic acid-rich protein like | 1.2E−08 |
| 74 | AK027813 | MGC10744 | hypothetical protein MGC10744 | 1.4E−08 |
| 75 | M57609 | GLI3 | GLI-Kruppel family member GLI3 (Greig cephalopolysyndactyly syndrome) | 1.7E−08 |
| 76 | AL359600 | EST | *Homo sapiens* mRNA; cDNA DKFZp547C136 (from clone DKFZp547C136) | 1.9E−08 |
| 77 | BQ006049 | TIMP1 | tissue inhibitor of metalloproteinase 1 (erythroid potentiating activity, collagenase inhibitor) | 2.1E−08 |
| 78 | AF111849 | HELO1 | homolog of yeast long chain polyunsaturated fatty acid elongation enzyme 2 | 2.2E−08 |
| 79 | AL157499 | RAB5EP | rabaptin-5 | 2.2E−08 |
| 80 | AK023199 | EST | *Homo sapiens* cDNA FLJ13137 fis, clone NT2RP3003150. | 2.5E−08 |
| 81 | J05176 | SERPINA 3 | serine (or cysteine) proteinase inhibitor, clade A (alpha-1 antiproteinase, antitrypsin), member 3 | 3.2E−08 |
| 82 | AA028101 | KIAA0303 | KIAA0303 protein | 3.3E−08 |
| 83 | AI300588 | MAP2K4 | mitogen-activated protein kinase kinase 4 | 4.1E−08 |
| 84 | AA682861 | ESTs | ESTs, Moderately similar to hypothetical protein FLJ20378 [*Homo sapiens*] [*H. sapiens*] | 4.6E−08 |
| 85 | M26393 | ACADS | acyl-Coenzyme A dehydrogenase, C-2 to C-3 short chain | 5.4E−08 |
| 86 | NM_001609 | ACADSB | acyl-Coenzyme A dehydrogenase, short/branched chain | 5.5E−08 |

TABLE 2-continued

List of genes with altered expression between ER-positive and ER-negative tumors

| BRC NO. | ACCESSION NO. | Symbol | TITLE | p-value |
|---|---|---|---|---|
| 87 | U91543 | CHD3 | chromodomain helicase DNA binding protein 3 | 5.7E−08 |
| 88 | AK023813 | FLJ10081 | hypothetical protein FLJ10081 | 6.0E−08 |
| 89 | BF111711 | FLJ20727 | hypothetical protein FLJ20727 | 7.0E−08 |
| 90 | AL049987 | EST | *Homo sapiens* mRNA; cDNA DKFZp564F112 (from clone DKFZp564F112) | 7.2E−08 |
| 91 | AW081894 | EST | EST | 8.2E−08 |
| 92 | AK000350 | FLJ20343 | hypothetical protein FLJ20343 | 1.1E−07 |
| 93 | AA418493 | DPP7 | dipeptidylpeptidase 7 | 1.1E−07 |
| 94 | BE674061 | PIN4 | protein (peptidyl-prolyl cis/trans isomerase) NIMA-interacting, 4 (parvulin) | 1.2E−07 |
| 95 | AB011155 | DLG5 | discs, large (*Drosophila*) homolog 5 | 1.2E−07 |
| 96 | L15203 | TFF3 | trefoil factor 3 (intestinal) | 1.4E−07 |
| 97 | NM_001552 | IGFBP4 | insulin-like growth factor binding protein 4 | 1.4E−07 |
| 98 | M57230 | IL6ST | interleukin 6 signal transducer (gp130, oncostatin M receptor) | 1.5E−07 |
| 99 | N92706 | EST | *Homo sapiens* cDNA FLJ38461 fis, clone FEBRA2020977. | 1.5E−07 |
| 100 | M30704 | AREG | amphiregulin (schwannoma-derived growth factor) | 1.8E−07 |
| 101 | AB004066 | BHLHB2 | basic helix-loop-helix domain containing, class B, 2 | 2.2E−07 |
| 102 | M15518 | PLAT | plasminogen activator, tissue | 2.3E−07 |
| 103 | BM697477 | ShrmL | Shroom-related protein | 2.4E−07 |
| 104 | R45979 | CELSR1 | cadherin, EGF LAG seven-pass G-type receptor 1 (flamingo homolog, *Drosophila*) | 3.0E−07 |
| 105 | AL049365 | EST | *Homo sapiens* mRNA; cDNA DKFZp586A0618 (from clone DKFZp586A0618) | 6.5E−07 |
| 106 | NM_003225 | TFF1 | trefoil factor 1 (breast cancer, estrogen-inducible sequence expressed in) | 7.1E−07 |
| 107 | AI733356 | EST | *Homo sapiens* cDNA FLJ31746 fis, clone NT2RI2007334. | 7.8E−07 |
| 108 | AF078853 | KIAA1243 | KIAA1243 protein | 8.2E−07 |
| 109 | N30179 | PLAB | prostate differentiation factor | 1.0E−06 |
| 110 | BG026429 | SFRS2 | splicing factor, arginine/serine-rich 2 | 2.4E−06 |
| 111 | AU149272 | ESTs | ESTs | 2.5E−06 |
| 112 | J03827 | NSEP 1 | nuclease sensitive element binding protein 1 | 3.0E−06 |
| 113 | AJ276469 | C20orf35 | chromosome 20 open reading frame 35 | 3.4E−06 |
| 114 | AW295100 | LOC201562 | hypothetical protein LOC201562 | 3.9E−06 |
| 115 | J03817 | GSTM1 | glutathione S-transferase M1 | 4.8E−06 |
| 116 | AF288571 | LEF1 | lymphoid enhancer-binding factor 1 | 5.1E−06 |
| 117 | AF069301 | PECI | peroxisomal D3,D2-enoyl-CoA isomerase | 5.3E−06 |
| 118 | AA621665 | EST | EST | 6.7E−06 |
| 119 | AI739486 | ESTs | ESTs | 8.0E−06 |
| 120 | X81438 | AMPH | amphiphysin (Stiff-Man syndrome with breast cancer 128 kDa autoantigen) | 8.7E−06 |
| 121 | U89606 | PDXK | pyridoxal (pyridoxine, vitamin B6) kinase | 8.8E−06 |
| 122 | NM_017555 | EGLN2 | egl nine homolog 2 (*C. elegans*) | 9.2E−06 |

TABLE 3

Genes commonly up-regulated in DCIS and IDC

| BRC NO. | ACCESSION NO. | | Symbol | TITLE |
|---|---|---|---|---|
| 123 | D90041 | | NAT1 | N-acetyltransferase 1 (arylamine N-acetyltransferase) |
| 124 | M13755 | | G1P2 | interferon, alpha-inducible protein (clone IFI-15K) |
| 125 | D88308 | | SLC27A2 | solute carrier family 27 (fatty acid transporter), member 2 |
| 126 | AW235061 | NM_004170 | SLC1A1 | solute carrier family 1 (neuronal/epithelial high affinity glutamate transporter, system Xag), member 1 |
| 127 | K02215 | | AGT | angiotensinogen (serine (or cysteine) proteinase inhibitor, clade A (alpha-1 antiproteinase, antitrypsin), member 8) |
| 128 | AB032261 | | SCD | stearoyl-CoA desaturase (delta-9-desaturase) |

TABLE 3-continued

Genes commonly up-regulated in DCIS and IDC

| BRC NO. | ACCESSION NO. | | Symbol | TITLE |
|---|---|---|---|---|
| 129 | NM_000909 | | NPY1R | neuropeptide Y receptor Y1 |
| 130 | AF017790 | | HEC | highly expressed in cancer, rich in leucine heptad repeats |
| 131 | NM_007019 | | UBE2C | ubiquitin-conjugating enzyme E2C |
| 132 | AF065388 | | TSPAN-1 | tetraspan 1 |
| 133 | N70334 | | DUSP10 | dual specificity phosphatase 10 |
| 134 | AA621719 | NM_005496 | SMC4L1 | SMC4 structural maintenance of chromosomes 4-like 1 (yeast) |
| 135 | AA676987 | | | ESTs |
| 136 | AK001402 | NM_018131 | C10orf3 | chromosome 10 open reading frame 3 |
| 137 | AW949747 | NM_002051 | GATA3 | GATA binding protein 3 |
| 138 | AK001472 | NM_018685 | ANLN | anillin, actin binding protein (scraps homolog, *Drosophila*) |
| 139 | AA789233 | NM_000088 | COL1A1 | collagen, type I, alpha 1 |
| 140 | AF070632 | | | *Homo sapiens* clone 24405 mRNA sequence |
| 141 | H04544 | | NPY1R | neuropeptide Y receptor Y1 |
| 142 | AI015982 | | CDCA1 | cell division cycle associated 1 |
| 143 | NM_003979 | | RAI3 | retinoic acid induced 3 |
| 144 | BF516445 | NM_053277 | CLIC6 | chloride intracellular channel 6 |
| 145 | AI361654 | | | |
| 146 | AI077540 | NM_178530 | | *Homo sapiens* cDNA FLJ38379 fis, clone FEBRA2002986. |
| 147 | AI261804 | | | *Homo sapiens* MSTP020 (MST020) mRNA, complete cds |
| 148 | AK026559 | | TPM3 | tropomyosin 3 |
| 149 | J03473 | | ADPRT | ADP-ribosyltransferase (NAD+; poly (ADP-ribose) polymerase) |
| 150 | NM_000187 | | HGD | homogentisate 1,2-dioxygenase (homogentisate oxidase) |
| 151 | L43964 | | PSEN2 | presenilin 2 (Alzheimer disease 4) |
| 152 | J05581 | | MUC1 | mucin 1, transmembrane |
| 153 | AA602499 | XM_379784 | GLCCI1 | glucocorticoid induced transcript 1 |
| 154 | U37707 | | MPP3 | membrane protein, palmitoylated 3 (MAGUK p55 subfamily member 3) |
| 155 | AB030905 | | CBX3 | chromobox homolog 3 (HP1 gamma homolog, *Drosophila*) |
| 156 | AL138409 | NM_198278 | | *Homo sapiens* mRNA; cDNA DKFZp313L231 (from clone DKFZp313L231) |
| 157 | AV756928 | | SEC61G | Sec61 gamma |
| 158 | AI205684 | NM_021979 | HSPA2 | heat shock 70 kDa protein 2 |
| 159 | BE739464 | NM_015161 | ARL6IP | ADP-ribosylation factor-like 6 interacting protein |
| 160 | AI081356 | NM_203463 | LOC253782 | hypothetical protein LOC253782 |
| 161 | AA167194 | | LOC253782 | hypothetical protein LOC253782 |
| 162 | M90516 | | GFPT1 | glutamine-fructose-6-phosphate transaminase 1 |
| 163 | AL133074 | NM_033285 | TP53INP1 | tumor protein p53 inducible nuclear protein 1 |
| 164 | AL137257 | | | *Homo sapiens*, clone IMAGE: 5296692, mRNA |
| 165 | AK025240 | NM_147128 | LOC223082 | LOC223082 |
| 166 | AJ007042 | | WHSC1 | Wolf-Hirschhorn syndrome candidate 1 |
| 167 | U42068 | | GRP58 | glucose regulated protein, 58 kDa |
| 168 | AJ132592 | | ZNF281 | zinc finger protein 281 |
| 169 | W93638 | | | ESTs |
| | AW977394 | | C9orf12 | chromosome 9 open reading frame 12 |
| 171 | AI347925 | NM_001540 | HSPB1 | heat shock 27 kDa protein 1 |
| 172 | AK026587 | | NET-6 | transmembrane 4 superfamily member tetraspan NET-6 |
| 173 | AI264621 | | LASS2 | LAG1 longevity assurance homolog 2 (*S. cerevisiae*) |
| 174 | AA767828 | XM_035527 | FLJ10980 | hypothetical protein FLJ10980 |
| 175 | AU142881 | NM_018184 | FLJ10702 | hypothetical protein FLJ10702 |

TABLE 4

Genes commonly down-regulated in DCIS and IDC

| BRC NO. | ACCESSION NO. | Symbol | TITLE |
|---|---|---|---|
| 176 | X52186 | ITGB4 | integrin, beta 4 |
| 177 | NM_006297 | XRCC1 | X-ray repair complementing defective repair in Chinese hamster cells 1 |
| 178 | X73460 | RPL3 | ribosomal protein L3 |
| 179 | NM_001436 | FBL | fibrillarin |
| 180 | X59373 | HOXD10 | homeo box D10 |
| 181 | J04208 | IMPDH2 | IMP (inosine monophosphate) dehydrogenase 2 |
| 182 | L24203 | TRIM29 | tripartite motif-containing 29 |
| 183 | L10340 | NM_001958 | EEF1A2 | eukaryotic translation elongation factor 1 alpha 2 |
| 184 | J04621 | SDC2 | syndecan 2 (heparan sulfate proteoglycan 1, cell surface-associated, fibroglycan) |
| 185 | L08424 | ASCL1 | achaete-scute complex-like 1 (*Drosophila*) |
| 186 | AI376713 | EST | ESTs, Weakly similar to hypothetical protein FLJ20378 [*Homo sapiens*] [*H. sapiens*] |
| 187 | AK026966 | EST | *Homo sapiens* cDNA: FLJ23313 fis, clone HEP11919. |
| 188 | NM_001050 | SSTR2 | somatostatin receptor 2 |
| 189 | AA632025 | EST | ESTs |
| 190 | N22918 | NM_144641 | FLJ32332 | hypothetical protein FLJ32332 |
| 191 | AF272043 | ITM2C | integral membrane protein 2C |
| 192 | M58459 | RPS4Y | ribosomal protein S4, Y-linked |
| 193 | AI133697 | EST | *Homo sapiens*, clone MGC: 16362 IMAGE: 3927795, mRNA, complete cds |
| 194 | AA780301 | NM_003793 | CTSF | cathepsin F |
| 195 | M92843 | ZFP36 | zinc finger protein 36, C3H type, homolog (mouse) |
| 196 | AA570186 | EST | Human full-length cDNA 5-PRIME end of clone CS0DK007YB08 of HeLa cells of *Homo sapiens* (human) |
| 197 | R56906 | EST | EST |
| 198 | AF208860 | NM_014452 | TNFRSF21 | tumor necrosis factor receptor superfamily, member 21 |
| 199 | AK025216 | TAZ | transcriptional co-activator with PDZ-binding motif (TAZ) |
| 200 | AA758394 | PTPN1 | protein tyrosine phosphatase, non-receptor type 1 |
| 201 | AA628530 | NM_016368 | ISYNA1 | myo-inositol 1-phosphate synthase A1 |
| 202 | AF161416 | NM_003749 | IRS2 | insulin receptor substrate 2 |
| 203 | AL045916 | EST | ESTs |
| 204 | AW340972 | EST | *Homo sapiens* cDNA: FLJ22864 fis, clone KAT02164. |
| 205 | AI189414 | RNPC2 | RNA-binding region (RNP1, RRM) containing 2 |
| 206 | AV705636 | EIF3S6IP | eukaryotic translation initiation factor 3, subunit 6 interacting protein |
| 207 | U28977 | CASP4 | caspase 4, apoptosis-related cysteine protease |
| 208 | AV708528 | NM_018579 | MSCP | mitochondrial solute carrier protein |
| 209 | AA022956 | NM_024667 | FLJ12750 | hypothetical protein FLJ12750 |
| 210 | AI928443 | EST | *Homo sapiens* cDNA FLJ38855 fis, clone MESAN2010681. |
| 211 | U14966 | RPL5 | ribosomal protein L5 |
| 212 | AI857997 | TPBG | trophoblast glycoprotein |
| 213 | BF697545 | MGP | matrix Gla protein |
| 214 | AW575754 | NM_152309 | FLJ35564 | hypothetical protein FLJ35564 |
| 215 | AI352534 | NM_001753 | CAV1 | caveolin 1, caveolae protein, 22 kDa |
| 216 | NM_001985 | ETFB | electron-transfer-flavoprotein, beta polypeptide |
| 217 | AI743134 | NM_006216 | SERPINE2 | serine (or cysteine) proteinase inhibitor, clade E (nexin, plasminogen activator inhibitor type 1), member 2 |
| 218 | AW444709 | NM_001777 | CD47 | CD47 antigen (Rh-related antigen, integrin-associated signal transducer) |
| 219 | BF688910 | NM_001300 | COPEB | core promoter element binding protein |
| 220 | AI818579 | NM_181847 | EST | *Homo sapiens*, clone IMAGE: 3625286, mRNA, partial cds |
| 221 | S95936 | TF | transferrin |
| 222 | AF074393 | RPS6KA5 | ribosomal protein S6 kinase, 90 kDa, polypeptide 5 |
| 223 | NM_000591 | CD14 | CD14 antigen |
| 224 | AK027181 | NM_031426 | IBA2 | ionized calcium binding adapter molecule 2 |
| 225 | X73079 | PIGR | polymeric immunoglobulin receptor |
| 226 | NM_001343 | DAB2 | disabled homolog 2, mitogen-responsive phosphoprotein (*Drosophila*) |

TABLE 4-continued

Genes commonly down-regulated in DCIS and IDC

| BRC NO. | ACCESSION NO. | | Symbol | TITLE |
|---|---|---|---|---|
| 227 | M31452 | | C4BPA | complement component 4 binding protein, alpha |
| 228 | X07696 | | KRT15 | keratin 15 |
| 229 | AF016004 | | GPM6B | glycoprotein M6B |
| 230 | NM_004078 | | CSRP1 | cysteine and glycine-rich protein 1 |
| 231 | L36645 | | EPHA4 | EphA4 |
| 232 | D78011 | | DPYS | dihydropyrimidinase |
| 233 | W60630 | NM_032801 | JAM3 | junctional adhesion molecule 3 |
| 234 | AW956111 | | D4S234E | DNA segment on chromosome 4 (unique) 234 expressed sequence |
| 235 | AF035752 | | CAV2 | caveolin 2 |
| 236 | D37766 | | LAMB3 | laminin, beta 3 |
| 237 | U66406 | | EFNB3 | ephrin-B3 |
| 238 | X52001 | | EDN3 | endothelin 3 |
| 239 | NM_000856 | | GUCY1A3 | guanylate cyclase 1, soluble, alpha 3 |
| 240 | U60115 | | FHL1 | four and a half LIM domains 1 |
| 241 | D14520 | NM_001730 | KLF5 | Kruppel-like factor 5 (intestinal) |
| 242 | M99487 | | FOLH1 | folate hydrolase (prostate-specific membrane antigen) 1 |
| 243 | U09873 | | FSCN1 | fascin homolog 1, actin-bundling protein (*Strongylocentrotus purpuratus*) |
| 244 | AF017418 | | MEIS2 | Meis1, myeloid ecotropic viral integration site 1 homolog 2 (mouse) |
| 245 | AF038540 | NM_206900 | RTN2 | reticulon 2 |
| 246 | AF049884 | NM_021069 | ARGBP2 | Arg/Abl-interacting protein ArgBP2 |
| 247 | NM_001122 | | ADFP | adipose differentiation-related protein |
| 248 | Y09926 | | MASP2 | mannan-binding lectin serine protease 2 |
| 249 | M58297 | | ZNF42 | zinc finger protein 42 (myeloid-specific retinoic acid-responsive) |
| 250 | AF035811 | | PNUTL2 | peanut-like 2 (*Drosophila*) |
| 251 | L22214 | | ADORA1 | adenosine A1 receptor |
| 252 | AF177775 | | CES1 | carboxylesterase 1 (monocyte/macrophage serine esterase 1) |
| 253 | U07643 | | LTF | lactotransferrin |
| 254 | S76474 | NM_006180 | NTRK2 | neurotrophic tyrosine kinase, receptor, type 2 |
| 255 | BE299605 | NM_012219 | MRAS | muscle RAS oncogene homolog |
| 256 | NM_006225 | | PLCD1 | phospholipase C, delta 1 |
| 257 | NM_005036 | | PPARA | peroxisome proliferative activated receptor, alpha |
| 258 | M22324 | | ANPEP | alanyl (membrane) aminopeptidase (aminopeptidase N, aminopeptidase M, microsomal aminopeptidase, CD13, p150) |
| 259 | BE877416 | | TGFBR2 | transforming growth factor, beta receptor II (70/80 kDa) |
| 260 | BE561244 | | RPL18A | ribosomal protein L18a |
| 261 | AL048962 | | EST | *Homo sapiens*, clone IMAGE: 4243767, mRNA |
| 262 | L08895 | | MEF2C | MADS box transcription enhancer factor 2, polypeptide C (myocyte enhancer factor 2C) |
| 263 | U48707 | | PPP1R1A | protein phosphatase 1, regulatory (inhibitor) subunit 1A |
| 264 | X56134 | | RPLP2 | ribosomal protein, large P2 |
| 265 | D84239 | | FCGBP | Fc fragment of IgG binding protein |
| 266 | AK026181 | | PHLDA1 | pleckstrin homology-like domain, family A, member 1 |
| 267 | K01144 | | CD74 | CD74 antigen (invariant polypeptide of major histocompatibility complex, class II antigen-associated) |
| 268 | U25138 | | KCNMB1 | potassium large conductance calcium-activated channel, subfamily M, beta member 1 |
| 269 | X85337 | NM_053025 | MYLK | myosin, light polypeptide kinase |
| 270 | D83597 | | LY64 | lymphocyte antigen 64 homolog, radioprotective 105 kDa (mouse) |
| 271 | NM_004024 | | ATF3 | activating transcription factor 3 |
| 272 | BF126636 | | SAA1 | serum amyloid A1 |
| 273 | D13789 | | MGAT3 | mannosyl (beta-1,4-)-glycoprotein beta-1,4-N-acetylglucosaminyltransferase |
| 274 | L41142 | | STAT5A | signal transducer and activator of transcription 5A |
| 275 | AB040969 | | KIAA1536 | KIAA1536 protein |
| 276 | NM_002153 | | HSD17B2 | hydroxysteroid (17-beta) dehydrogenase 2 |
| 277 | AV646610 | NM_001546 | ID4 | inhibitor of DNA binding 4, dominant negative helix-loop-helix protein |

TABLE 4-continued

Genes commonly down-regulated in DCIS and IDC

| BRC NO. | ACCESSION NO. | | Symbol | TITLE |
|---|---|---|---|---|
| 278 | X03663 | | CSF1R | colony stimulating factor 1 receptor, formerly McDonough feline sarcoma viral (v-fms) oncogene homolog |
| 279 | U47025 | | PYGB | phosphorylase, glycogen; brain |
| 280 | M81349 | | SAA4 | serum amyloid A4, constitutive |
| 281 | AI264201 | NM_000399 | EGR2 | early growth response 2 (Krox-20 homolog, *Drosophila*) |
| 282 | U18018 | | ETV4 | ets variant gene 4 (E1A enhancer binding protein, E1AF) |
| 283 | NM_004350 | | RUNX3 | runt-related transcription factor 3 |
| 284 | BF337516 | | CRYAB | crystallin, alpha B |
| 285 | AF027208 | | PROML1 | prominin-like 1 (mouse) |
| 286 | D17408 | | CNN1 | calponin 1, basic, smooth muscle |
| 287 | NM_004010 | | DMD | dystrophin (muscular dystrophy, Duchenne and Becker types) |
| 288 | BF183952 | | CSTA | cystatin A (stefin A) |
| 289 | M16445 | | CD2 | CD2 antigen (p50), sheep red blood cell receptor |
| 290 | AF055015 | | EYA2 | eyes absent homolog 2 (*Drosophila*) |
| 291 | AI745624 | | ELL2 | ELL-related RNA polymerase II, elongation factor |
| 292 | AK025329 | | DKFZP566H073 | DKFZP566H073 protein |
| 293 | BE745465 | NM_012427 | KLK5 | kallikrein 5 |
| 294 | AK024578 | NM_031455 | DKFZP761F241 | hypothetical protein DKFZp761F241 |
| 295 | AI870306 | XM_380171 | IRX1 | iroquois homeobox protein 1 |
| 296 | H37853 | NM_022343 | C9orf19 | chromosome 9 open reading frame 19 |
| 297 | BF000047 | | EST | *Homo sapiens* full length insert cDNA clone ZA79C08 |
| 298 | AF126780 | | RetSDR2 | retinal short-chain dehydrogenase/reductase 2 |
| 299 | AI700341 | | EST | ESTs, Weakly similar to hypothetical protein FLJ20489 [*Homo sapiens*] [*H. sapiens*] |
| 300 | M87770 | | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) |
| 301 | AA452368 | NM_144595 | FLJ30046 | hypothetical protein FLJ30046 |
| 302 | NM_021200 | | PLEKHB1 | pleckstrin homology domain containing, family B (evectins) member 1 |
| 303 | AK026343 | | hIAN2 | human immune associated nucleotide 2 |
| 304 | AF251040 | | C5orf6 | chromosome 5 open reading frame 6 |
| 305 | M87507 | | CASP1 | caspase 1, apoptosis-related cysteine protease (interleukin 1, beta, convertase) |
| 306 | M97675 | | ROR1 | receptor tyrosine kinase-like orphan receptor 1 |
| 307 | NM_020549 | | CHAT | choline acetyltransferase |
| 308 | X00457 | NM_033554 | HLA-DPA1 | major histocompatibility complex, class II, DP alpha 1 |
| 309 | W72411 | NM_003722 | TP73L | tumor protein p73-like |
| 310 | AI769569 | | EST | ESTs |
| 311 | K02765 | | C3 | complement component 3 |
| 312 | AW971490 | | FLJ14906 | hypothetical protein FLJ14906 |
| 313 | AF077044 | | RPAC2 | likely ortholog of mouse RNA polymerase 1-3 (16 kDa subunit) |
| 314 | H70803 | NM_015278 | KIAA0790 | KIAA0790 protein |
| 315 | AL050367 | XM_167709 | LOC221061 | hypothetical protein LOC221061 |
| 316 | AK001643 | NM_018215 | FLJ10781 | hypothetical protein FLJ10781 |
| 317 | AW182273 | | EST | *Homo sapiens* cDNA FLJ31517 fis, clone NT2RI2000007. |
| 318 | W67951 | | EST | Human S6 A-5 mRNA expressed in chromosome 6-suppressed melanoma cells. |
| 319 | AL117605 | | EST | *Homo sapiens* mRNA; cDNA DKFZp564N1063 (from clone DKFZp564N1063) |
| 320 | AI376418 | | EST | *Homo sapiens* cDNA FLJ35169 fis, clone PLACE6012908. |
| 321 | AA683373 | | EST | EST |
| 322 | AK022877 | | EST | *Homo sapiens* cDNA FLJ12815 fis, clone NT2RP2002546. |
| 323 | NM_002258 | | KLRB1 | killer cell lectin-like receptor subfamily B, member 1 |
| 324 | M69225 | | BPAG1 | bullous pemphigoid antigen 1, 230/240 kDa |
| 325 | AW299572 | NM_015461 | EHZF | early hematopoietic zinc finger |
| 326 | BE044467 | NM_005737 | ARL7 | ADP-ribosylation factor-like 7 |
| 327 | AA938297 | NM_017938 | FLJ20716 | hypothetical protein FLJ20716 |
| 328 | AA706316 | NM_033317 | ZD52F10 | hypothetical gene ZD52F10 |

TABLE 4-continued

Genes commonly down-regulated in DCIS and IDC

| BRC NO. | ACCESSION NO. | | Symbol | TITLE |
|---|---|---|---|---|
| 329 | AI827230 | NM_153000 | APCDD1 | adenomatosis polyposis coli down-regulated 1 |
| 330 | AK000251 | | FLJ20244 | hypothetical protein FLJ20244 |
| 331 | N62352 | NM_020925 | KIAA1573 | KIAA1573 protein |
| 332 | H53164 | | ICSBP1 | interferon consensus sequence binding protein 1 |
| 333 | BE394824 | | WFDC2 | WAP four-disulfide core domain 2 |
| 334 | AL117462 | NM_015481 | ZFP385 | likely ortholog of mouse zinc finger protein 385 |
| 335 | NM_003186 | | TAGLN | transgelin |
| 336 | U58514 | | CHI3L2 | chitinase 3-like 2 |
| 337 | AB026125 | | ART-4 | ART-4 protein |
| 338 | AL080059 | NM_033512 | KIAA1750 | KIAA1750 protein |
| 339 | AA747005 | | SDCCAG43 | serologically defined colon cancer antigen 43 |
| 340 | NM_005928 | | MFGE8 | milk fat globule-EGF factor 8 protein |
| 341 | D62470 | NM_004796 | NRXN3 | neurexin 3 |
| 342 | N29574 | | RAGD | Rag D protein |
| 343 | K02276 | | MYC | v-myc myelocytomatosis viral oncogene homolog (avian) |
| 344 | D78611 | | MEST | mesoderm specific transcript homolog (mouse) |
| 345 | NM_022003 | | FXYD6 | FXYD domain containing ion transport regulator 6 |
| 346 | BF508973 | | RPL13 | ribosomal protein L13 |
| 347 | NM_001615 | | ACTG2 | actin, gamma 2, smooth muscle, enteric |
| 348 | R41532 | | EST | ESTs, Weakly similar to POL2_MOUSE Retrovirus-related POL polyprotein [Contains: Reverse transcriptase; Endonuclease] [*M. musculus*] |
| 349 | AA142875 | | EST | ESTs |
| 350 | U03688 | | CYP1B1 | cytochrome P450, family 1, subfamily B, polypeptide 1 |
| 351 | W94363 | | EST | *Homo sapiens* full length insert cDNA clone ZE12G01 |
| 352 | W44613 | | HSJ001348 | cDNA for differentially expressed CO16 gene |
| 353 | AL118812 | | EST | *Homo sapiens* mRNA; cDNA DKFZp761G1111 (from clone DKFZp761G1111) |
| 354 | D56064 | | MAP2 | microtubule-associated protein 2 |
| 355 | BF966838 | NM_172069 | KIAA2028 | similar to PH (pleckstrin homology) domain |
| 356 | AI338625 | NM_014344 | FJX1 | four jointed box 1 (*Drosophila*) |
| 357 | AI263022 | | EST | ESTs |
| 358 | AL050107 | NM_015472 | TAZ | transcriptional co-activator with PDZ-binding motif (TAZ) |
| 359 | AI056364 | NM_033210 | FLJ14855 | hypothetical protein FLJ14855 |
| 360 | AI351898 | NM_032581 | DRCTNNB1A | down-regulated by Ctnnb1, a |
| 361 | AV700003 | | ARL6IP2 | ADP-ribosylation-like factor 6 interacting protein 2 |
| 362 | NM_000700 | | ANXA1 | annexin A1 |
| 363 | M81141 | | HLA-DQB1 | major histocompatibility complex, class II, DQ beta 1 |
| 364 | AI598227 | NM_024911 | FLJ23091 | hypothetical protein FLJ23091 |
| 365 | BG034740 | | ROPN1 | ropporin, rhophilin associated protein 1 |
| 366 | AB011175 | | TBC1D4 | TBC1 domain family, member 4 |
| 367 | AK024449 | | PP2135 | PP2135 protein |
| 368 | AW978770 | | DKFZP566A1524 | hypothetical protein DKFZp566A1524 |
| 369 | AI821113 | | EST | *Homo sapiens* cDNA FLJ36327 fis, clone THYMU2005748. |
| 370 | AI057450 | | SLC13A2 | solute carrier family 13 (sodium-dependent dicarboxylate transporter), member 2 |
| 371 | X86693 | | SPARCL1 | SPARC-like 1 (mast9, hevin) |
| 372 | AI224952 | NM_173640 | FLJ40906 | hypothetical protein FLJ40906 |
| 373 | D13639 | | CCND2 | cyclin D2 |

TABLE 5

Genes with elevated expression in transition from DCIS to IDC

| BRC NO. | ACCESSION NO. | | Symbol | TITLE |
|---|---|---|---|---|
| 374 | U74612 | | FOXM1 | forkhead box M1 |
| 375 | U63743 | | KIF2C | kinesin family member 2C |
| 376 | D88532 | | PIK3R3 | phosphoinositide-3-kinase, regulatory subunit, polypeptide 3 (p55, gamma) |
| 377 | NM_005532 | | IFI27 | interferon, alpha-inducible protein 27 |
| 378 | D14657 | | KIAA0101 | KIAA0101 gene product |
| 379 | AF030186 | | GPC4 | glypican 4 |
| 380 | Z11566 | | STMN1 | stathmin 1/oncoprotein 18 |
| 381 | U90914 | NM_001304 | CPD | carboxypeptidase D |
| 382 | NM_002534 | | OAS1 | 2',5'-oligoadenylate synthetase 1, 40/46 kDa |
| 383 | S67310 | | BF | B-factor, properdin |
| 384 | AA192445 | NM_020182 | TMEPAI | transmembrane, prostate androgen induced RNA |
| 385 | AB003103 | | PSMD12 | proteasome (prosome, macropain) 26S subunit, non-ATPase, 12 |
| 386 | BE878057 | NM_030796 | DKFZP564K0822 | hypothetical protein DKFZp564K0822 |
| 387 | AB003698 | | CDC7L1 | CDC7 cell division cycle 7-like 1 (*S. cerevisiae*) |
| 388 | M91670 | | E2-EPF | ubiquitin carrier protein |
| 389 | AK023414 | | FLJ13352 | hypothetical protein FLJ13352 |
| 390 | L09235 | | ATP6V1A1 | ATPase, H+ transporting, lysosomal 70 kDa, V1 subunit A, isoform 1 |
| 391 | AF007152 | | ABHD3 | abhydrolase domain containing 3 |
| 392 | U33632 | | KCNK1 | potassium channel, subfamily K, member 1 |
| 393 | AA621719 | NM_005496 | SMC4L1 | SMC4 structural maintenance of chromosomes 4-like 1 (yeast) |
| 394 | AF176228 | | DNMT3B | DNA (cytosine-5-)-methyltransferase 3 beta |
| 395 | H22566 | NM_080759 | DACH | dachshund homolog (*Drosophila*) |
| 396 | AI185804 | NM_212482 | FN1 | fibronectin 1 |
| 397 | AI189477 | NM_002168 | IDH2 | isocitrate dehydrogenase 2 (NADP+), mitochondrial |
| 398 | AA205444 | | AP1S2 | adaptor-related protein complex 1, sigma 2 subunit |

TABLE 6

Genes with decreasd expression in transition from DCIS to IDC

| | ACCESSION | | Symbol | TITLE |
|---|---|---|---|---|
| 399 | AF070609 | NM_004172 | SLC1A3 | solute carrier family 1 (glial high affinity glutamate transporter), member 3 |
| 400 | U85267 | | DSCR1 | Down syndrome critical region gene 1 |
| 401 | NM_005397 | | PODXL | podocalyxin-like |
| 402 | D13811 | | AMT | aminomethyltransferase (glycine cleavage system protein T) |
| 403 | X53586 | | ITGA6 | integrin, alpha 6 |
| 404 | L13288 | | VIPR1 | vasoactive intestinal peptide receptor 1 |
| 405 | M12125 | | TPM2 | tropomyosin 2 (beta) |
| 406 | M65066 | NM_002735 | PRKAR1B | protein kinase, cAMP-dependent, regulatory, type I, beta |
| 407 | AJ001183 | | SOX10 | SRY (sex determining region Y)-box 10 |
| 408 | AW241712 | | MXI1 | MAX interacting protein 1 |
| 409 | AL160111 | | KIAA1649 | KIAA1649 protein |
| 410 | X93920 | | DUSP6 | dual specificity phosphatase 6 |
| 411 | AF132734 | NM_021807 | SEC8 | secretory protein SEC8 |
| 412 | AI133467 | | | ESTs |
| 413 | D88153 | | HYA22 | HYA22 protein |
| 414 | AF014404 | | PTE1 | peroxisomal acyl-CoA thioesterase |
| 415 | BE907755 | NM_013399 | C16orf5 | chromosome 16 open reading frame 5 |
| 416 | AA135341 | NM_021078 | GCN5L2 | GCN5 general control of amino-acid synthesis 5-like 2 (yeast) |
| 417 | AL110126 | | | *Homo sapiens* mRNA; cDNA DKFZp564H1916 (from clone DKFZp564H1916) |
| 418 | BE254330 | NM_003045 | | *Homo sapiens* mRNA; cDNA DKFZp564D016 (from clone DKFZp564D016) |
| 419 | BE264353 | | RBP1 | retinol binding protein 1, cellular |
| 420 | W75991 | | | *Homo sapiens*, clone IMAGE: 4249217, mRNA |
| 421 | AF091434 | | PDGFC | platelet derived growth factor C |

TABLE 6-continued

Genes with decreasd expression in transition from DCIS to IDC

| | ACCESSION | | Symbol | TITLE |
|---|---|---|---|---|
| 422 | W67577 | | CD74 | CD74 antigen (invariant polypeptide of major histocompatibility complex, class II antigen-associated) |
| 423 | NM_002996 | | CX3CL1 | chemokine (C—X3—C motif) ligand 1 |
| 424 | AA024459 | | | ESTs |
| 425 | NM_000163 | | GHR | growth hormone receptor |
| 426 | AA858162 | NM_032160 | NCAG1 | NCAG1 |
| 427 | BE327623 | | | ESTs, Weakly similar to hypothetical protein FLJ20234 [*Homo sapiens*] [*H. sapiens*] |
| 428 | BE671156 | | MAPRE2 | microtubule-associated protein, RP/EB family, member 2 |
| 429 | D12614 | | LTA | lymphotoxin alpha (TNF superfamily, member 1) |
| 430 | L13720 | | MGC5560 | hypothetical protein MGC5560 |
| 431 | U15131 | | ST5 | suppression of tumorigenicity 5 |
| 432 | Y00711 | | LDHB | lactate dehydrogenase B |
| 433 | AI651212 | | | *Homo sapiens* cDNA FLJ31125 fis, clone IMR322000819. |
| 434 | M31159 | | IGFBP3 | insulin-like growth factor binding protein 3 |
| 435 | NM_014447 | | HSU52521 | arfaptin 1 |
| 436 | AB011089 | | TRIM2 | tripartite motif-containing 2 |
| 437 | BF969355 | NM_002612 | PDK4 | pyruvate dehydrogenase kinase, isoenzyme 4 |
| 438 | AK025950 | XM_371114 | KIAA1695 | hypothetical protein FLJ22297 |
| 439 | D86961 | NM_005779 | LHFPL2 | lipoma HMGIC fusion partner-like 2 |
| 440 | AK025953 | | | *Homo sapiens* cDNA: FLJ22300 fis, clone HRC04759. |
| 441 | AJ223812 | | CALD1 | caldesmon 1 |
| 442 | R40594 | | | *Homo sapiens* cDNA: FLJ22845 fis, clone KAIA5195. |
| 443 | AF145713 | | SCHIP1 | schwannomin interacting protein 1 |
| 444 | AK024966 | | FLJ21313 | hypothetical protein FLJ21313 |
| 445 | NM_005596 | | NFIB | nuclear factor I/B |
| 446 | NM_001613 | | ACTA2 | actin, alpha 2, smooth muscle, aorta |
| 447 | H03641 | XM_376328 | FAM13A1 | family with sequence similarity 13, member A1 |

TABLE 7

Genes commonly up-regulated in IDC

| BRC NO. | ACCESSION NO. | | Symbol | TITLE |
|---|---|---|---|---|
| 448 | X14420 | | COL3A1 | collagen, type III, alpha 1 (Ehlers-Danlos syndrome type IV, autosomal dominant) |
| 449 | AF044588 | | PRC1 | protein regulator of cytokinesis 1 |
| | AF161499 | | HSPC150 | HSPC150 protein similar to ubiquitin-conjugating enzyme |
| 451 | AA789233 | NM_000088 | COL1A1 | collagen, type I, alpha 1 |
| 452 | U16306 | | CSPG2 | chondroitin sulfate proteoglycan 2 (versican) |
| 453 | NM_004425 | | ECM1 | extracellular matrix protein 1 |
| 454 | NM_006855 | | KDELR3 | KDEL (Lys-Asp-Glu-Leu; SEQ ID NO: 52) endoplasmic reticulum protein retention receptor 3 |
| 455 | AI972071 | NM_031966 | CCNB1 | cyclin B1 |
| 456 | AF237709 | NM_018492 | TOPK | T-LAK cell-originated protein kinase (SEQ ID NOS: 48-51) |
| 457 | BE747327 | | HIST1H1C | histone 1, H1c |
| 458 | J03464 | | COL1A2 | collagen, type I, alpha 2 |
| 459 | AI080640 | NM_006408 | AGR2 | anterior gradient 2 homolog (*Xenepus laevis*) |
| 460 | AA971042 | | RHPN1 | rhophilin, Rho GTPase binding protein 1 |
| 461 | AI419398 | | MGC33662 | hypothetical protein MGC33662 |
| 462 | AI149552 | NM_004448 | | ESTs, Moderately similar to ERB2_HUMAN Receptor protein-tyrosine kinase erbB-2 precursor (p185erbB2) (NEU proto-oncogene) (C-erbB-2) (Tyrosine kinase-type cell surface receptor HER2) (MLN 19) [*H. sapiens*] |
| 463 | D14874 | | ADM | adrenomedullin |
| 464 | X03674 | NM_000402 | G6PD | glucose-6-phosphate dehydrogenase |
| 465 | NM_002358 | | MAD2L1 | MAD2 mitotic arrest deficient-like 1 (yeast) |
| 466 | BF214508 | | CYCS | cytochrome c, somatic |
| 467 | BG030536 | NM_001067 | TOP2A | topoisomerase (DNA) II alpha 170 kDa |
| 468 | X57766 | | MMP11 | matrix metalloproteinase 11 (stromelysin 3) |

TABLE 7-continued

Genes commonly up-regulated in IDC

| BRC NO. | ACCESSION NO. | | Symbol | TITLE |
|---|---|---|---|---|
| 469 | AA029900 | NM_015170 | SULF1 | sulfatase 1 |
| 470 | AF053306 | | BUB1B | BUB1 budding uninhibited by benzimidazoles 1 homolog beta (yeast) |
| 471 | AF074002 | | LGALS8 | lectin, galactoside-binding, soluble, 8 (galectin 8) |

TABLE 8

Genes commonly down-regulated in IDC

| BRC NO. | ACCESSION NO. | | Symbol | TITLE |
|---|---|---|---|---|
| 472 | NM_004484 | | GPC3 | glypican 3 |
| 473 | NM_006219 | | PIK3CB | phosphoinositide-3-kinase, catalytic, beta polypeptide |
| 474 | BE793000 | | RBP1 | retinol binding protein 1, cellular |
| 475 | AL117565 | NM_033027 | AXUD1 | AXIN1 up-regulated 1 |
| 476 | BF055342 | | ZNF6 | zinc finger protein 6 (CMPX1) |
| 477 | U03688 | | CYP1B1 | cytochrome P450, family 1, subfamily B, polypeptide 1 |
| 478 | AF038193 | NM_004311 | | Homo sapiens, clone IMAGE: 3610040, mRNA |
| 479 | X72760 | NM_002292 | LAMB2 | laminin, beta 2 (laminin S) |
| 480 | J03817 | | GSTM1 | glutathione S-transferase M1 |
| 481 | M69226 | | MAOA | monoamine oxidase A |
| 482 | BF690180 | NM_006990 | WASF2 | WAS protein family, member 2 |
| 483 | AL133600 | | STAM2 | signal transducing adaptor molecule (SH3 domain and ITAM motif) 2 |
| 484 | AF215981 | | GPR2 | G protein-coupled receptor 2 |
| 485 | BG149764 | | | Homo sapiens, clone IMAGE: 5286091, mRNA, partial cds |
| 486 | AF067800 | | CLECSF6 | C-type (calcium dependent, carbohydrate-recognition domain) lectin, superfamily member 6 |
| 487 | AA713487 | | PIK3R1 | phosphoinositide-3-kinase, regulatory subunit, polypeptide 1 (p85 alpha) |
| 488 | AA828505 | | FBXW7 | F-box and WD-40 domain protein 7 (archipelago homolog, Drosophila) |
| 489 | AK021865 | | CKIP-1 | CK2 interacting protein 1; HQ0024c protein |
| 490 | AK001605 | | FLJ10743 | hypothetical protein FLJ10743 |
| 491 | AI041186 | | HSPC182 | HSPC182 protein |
| 492 | AA873363 | NM_144650 | ADH8 | alcohol dehydrogenase 8 |
| 493 | NM_013409 | | FST | follistatin |
| 494 | AK000322 | | FLJ20315 | hypothetical protein FLJ20315 |
| 495 | AB020637 | XM_290546 | KIAA0830 | KIAA0830 protein |
| 496 | AA872040 | | INHBB | inhibin, beta B (activin AB beta polypeptide) |
| 497 | NM_004430 | | EGR3 | early growth response 3 |
| 498 | D59989 | | | ESTs |
| 499 | D78013 | | DPYSL2 | dihydropyrimidinase-like 2 |
| 500 | AI081821 | | | Homo sapiens mRNA; cDNA DKFZp313M0417 (from clone DKFZp313M0417) |
| 501 | AA309603 | | KIAA1430 | KIAA1430 protein |
| 502 | NM_004107 | | FCGRT | Fc fragment of IgG, receptor, transporter, alpha |
| 503 | AW268719 | | | Homo sapiens cDNA FLJ32438 fis, clone SKMUS2001402. |
| 504 | BF446578 | NM_145313 | LOC221002 | CG4853 gene product |
| 505 | BG054844 | NM_005168 | ARHE | ras homolog gene family, member E |
| 506 | AF054987 | | ALDOC | aldolase C, fructose-bisphosphate |
| 507 | AI052390 | | FLJ20071 | dymeclin |
| 508 | NM_004530 | | MMP2 | matrix metalloproteinase 2 (gelatinase A, 72 kDa gelatinase, 72 kDa type IV collagenase) |
| 509 | AF054999 | NM_001431 | EPB41L2 | erythrocyte membrane protein band 4.1-like 2 |
| 510 | AU151591 | NM_182964 | NAV2 | neuron navigator 2 |
| 511 | AA447744 | | | ESTs |
| 512 | R61253 | | ST6GalII | beta-galactoside alpha-2,6-sialyltransferase II |

TABLE 9

Primer sequences for semi-quantitative RT-PCR experiments

| ACCESSION NO. | Symbol | Forward primer | Reverse primer |
|---|---|---|---|
| AI261804 | EST | 5'-CTGTTCTGGC TTCGTTA TGT TCT-3' (SEQ ID NO: 1) | 5'-AGAAAATACG GTCCTCT TGT TGC-3' (SEQ ID NO: 2) |
| AA205444 | AP1S2 | 5'-CACTGTAATG CACGAC ATTT GA-3' (SEQ ID NO: 3) | 5'-GTTACAGCTT AGCACAA GGC ATC-3' (SEQ ID NO: 4) |
| AA167194 | LOC25 3782 | 5'-ACCTCTGAGT TTGATTT CCC AA-3' (SEQ ID NO: 5) | 5'-CGAGGCTTGT AACAATC TAC TGG-3' (SEQ ID NO: 6) |
| AA676987 | EST | 5'-GAAACTGTAC GGGGGT TAAA GAG-3' (SEQ ID NO: 7) | 5'CATCAATGTG GTGAGTG ACA TCT-3' (SEQ ID NO: 8) |
| H22566 | DACH | 5'-AAGCCCTTGG AACAGA ACAT ACT-3' (SEQ ID NO: 9) | 5'-CAGTAAACGT GGTTCTC ACA TTG-3' (SEQ ID NO: 10) |
| NM_018492 | TOPK | 5'-AGACCCTAAAGATCGTC CTTCTG-3' (SEQ ID NO: 13) | 5'-GTGTTTTAAGTCAGCATG AGCAG-3' (SEQ ID NO: 14) |
| NM_002046 | GAPD | 5'-CGACCACTTT GTCAAGC TCA-3' (SEQ ID NO: 11) | 5'-GGTTGAGCAC AGGGTAC TTT ATT-3' (SEQ ID NO: 12) |

TABLE 10

List of genes with altered expression between well and poorly differentiated type in single case

| BRC NO. | ACCESSION NO. | | Symbol | TITLE | p-value |
|---|---|---|---|---|---|
| 513 | AV729269 | XM_371074 | DKFZP564D166 | putative ankyrin-repeat containing protein | 3.1E-07 |
| 514 | AI246554 | NM_014222 | NDUFA8 | NADH dehydrogenase (ubiquinone) 1 alpha subcomplex, 8, 19 kDa | 1.4E-06 |
| 515 | J04080 | | C1S | complement component 1, s subcomponent | 1.4E-05 |
| 516 | N93264 | | EST | *Homo sapiens*, clone IMAGE: 4908933, mRNA | 1.4E-05 |
| 517 | NM_002318 | | LOXL2 | lysyl oxidase-like 2 | 1.6E-05 |
| 518 | J03464 | | COL1A2 | collagen, type I, alpha 2 | 2.4E-05 |
| 519 | U01184 | NM_002018 | FLII | flightless I homolog (*Drosophila*) | 2.5E-05 |
| 520 | X63556 | | FBN1 | fibrillin 1 (Marfan syndrome) | 3.8E-05 |
| 521 | X78137 | | PCBP1 | poly(rC) binding protein 1 | 4.6E-05 |
| 522 | AK021534 | | EST | *Homo sapiens* cDNA FLJ11472 fis, clone HEMBA1001711. | 6.3E-05 |
| 523 | AK024012 | | NPD002 | NPD002 protein | 6.3E-05 |
| 524 | AI200892 | | BIK | BCL2-interacting killer (apoptosis-inducing) | 9.1E-05 |
| 525 | J03040 | | SPARC | secreted protein, acidic, cysteine-rich (osteonectin) | 9.3E-05 |
| 526 | AW970143 | | C6orf49 | chromosome 6 open reading frame 49 | 1.0E-04 |
| 527 | D62873 | | EST | *Homo sapiens*, clone IMAGE: 5288080, mRNA | 1.2E-04 |
| 528 | D42041 | | G2AN | alpha glucosidase II alpha subunit | 1.2E-04 |
| 529 | AI376418 | | EST | *Homo sapiens* cDNA FLJ35169 fis, clone PLACE6012908. | 1.7E-04 |
| 530 | AK026744 | NM_024911 | FLJ23091 | hypothetical protein FLJ23091 | 1.8E-04 |
| 531 | AF026292 | | CCT7 | chaperonin containing TCP1, subunit 7 (eta) | 2.0E-04 |
| 532 | Y10805 | | HRMT1L2 | HMT1 hnRNP methyltransferase-like 2 (*S. cerevisiae*) | 2.1E-04 |
| 533 | L12350 | | THBS2 | thrombospondin 2 | 2.1E-04 |
| 534 | AK025706 | | AMPD2 | adenosine monophosphate deaminase 2 (isoform L) | 2.4E-04 |
| 535 | BE618804 | | PIG11 | p53-induced protein | 2.5E-04 |
| 536 | AV713686 | | RPS29 | ribosomal protein S29 | 2.8E-04 |
| 537 | M26481 | | TACSTD1 | tumor-associated calcium signal transducer 1 | 2.8E-04 |
| 538 | D00099 | | ATP1A1 | ATPase, Na+/K+ transporting, alpha 1 polypeptide | 2.9E-04 |
| 539 | AA946602 | | ORMDL2 | ORM1-like 2 (*S. cerevisiae*) | 2.9E-04 |
| 540 | NM_001533 | | HNRPL | heterogeneous nuclear ribonucleoprotein L | 3.9E-04 |

TABLE 10-continued

List of genes with altered expression between well and poorly differentiated type in single case

| BRC NO. | ACCESSION NO. | | Symbol | TITLE | p-value |
|---|---|---|---|---|---|
| 541 | BG107866 | | SIVA | CD27-binding (Siva) protein | 4.4E−04 |
| 542 | W72297 | NM_017866 | FLJ20533 | hypothetical protein FLJ20533 | 4.4E−04 |
| 543 | U76992 | | HTATSF1 | HIV TAT specific factor 1 | 4.8E−04 |
| 544 | AA191454 | NM_198897 | FIBP | fibroblast growth factor (acidic) intracellular binding protein | 4.9E−04 |
| 545 | BE903483 | | RPS20 | ribosomal protein S20 | 5.4E−04 |
| 546 | AJ005282 | | NPR2 | natriuretic peptide receptor B/guanylate cyclase B (atrionatriuretic peptide receptor B) | 5.5E−04 |
| 547 | D86322 | | CLGN | calmegin | 5.7E−04 |
| 548 | AA621665 | | EST | EST | 5.8E−04 |
| 549 | M77349 | | TGFBI | transforming growth factor, beta-induced, 68 kDa | 6.3E−04 |
| 550 | BE176466 | | ZAP3 | ZAP3 protein | 6.6E−04 |
| 551 | AA776882 | NM_030795 | STMN4 | stathmin-like 4 | 7.1E−04 |
| 552 | AI261382 | NM_016334 | SH120 | putative G-protein coupled receptor | 7.1E−04 |
| 553 | AB007618 | | COX7A2L | cytochrome c oxidase subunit VIIa polypeptide 2 like | 7.2E−04 |
| 554 | D21261 | | TAGLN2 | transgelin 2 | 7.5E−04 |
| 555 | M68864 | | LOC51035 | ORF | 7.7E−04 |
| 556 | AB007836 | | TGFB1I1 | transforming growth factor beta 1 induced transcript 1 | 8.1E−04 |
| 557 | AA173339 | | EST | EST | 8.4E−04 |
| 558 | D87810 | | PMM1 | phosphomannomutase 1 | 8.4E−04 |
| 559 | M15798 | NM_183356 | ASNS | asparagine synthetase | 8.7E−04 |
| 560 | AW072418 | | B7 | B7 protein | 9.0E−04 |
| 561 | D38293 | | AP3M2 | adaptor-related protein complex 3, mu 2 subunit | 9.5E−04 |
| 562 | NM_018950 | | HLA-F | major histocompatibility complex, class I, F | 1.0E−03 |
| 563 | NM_001219 | | CALU | calumenin | 1.1E−03 |
| 564 | J04162 | | FCGR3A | Fc fragment of IgG, low affinity IIIa, receptor for (CD16) | 1.1E−03 |
| 565 | U09873 | | FSCN1 | fascin homolog 1, actin-bundling protein (Strongylocentrotus purpuratus) | 1.1E−03 |
| 566 | N51082 | NM_080759 | DACH | dachshund homolog (*Drosophila*) | 1.3E−03 |
| 567 | NM_004199 | | P4HA2 | procollagen-proline, 2-oxoglutarate 4-dioxygenase (proline 4-hydroxylase), alpha polypeptide II | 1.3E−03 |
| 568 | BE904196 | | GNB1 | guanine nucleotide binding protein (G protein), beta polypeptide 1 | 1.3E−03 |
| 569 | L08895 | | MEF2C | MADS box transcription enhancer factor 2, polypeptide C (myocyte enhancer factor 2C) | 1.3E−03 |
| 570 | AK022670 | NM_016649 | C20orf6 | chromosome 20 open reading frame 6 | 1.3E−03 |
| 571 | AW157725 | | POLR2F | polymerase (RNA) II (DNA directed) polypeptide F | 1.4E−03 |
| 572 | NM_004939 | | DDX1 | DEAD/H (Asp-Glu-Ala-Asp/His) box polypeptide 1 | 1.4E−03 |
| 573 | X65463 | NM_021976 | RXRB | retinoid X receptor, beta | 1.5E−03 |
| 574 | Z68179 | | LY6E | lymphocyte antigen 6 complex, locus E | 1.5E−03 |
| 575 | BF976420 | | SNRPF | small nuclear ribonucleoprotein polypeptide F | 1.5E−03 |
| 576 | D79986 | | BTF | Bcl-2-associated transcription factor | 1.5E−03 |
| 577 | AK001023 | | NUBP2 | nucleotide binding protein 2 (MinD homolog, *E. coli*) | 1.6E−03 |
| 578 | BE065329 | | EST | EST | 1.6E−03 |
| 579 | L34600 | | MTIF2 | mitochondrial translational initiation factor 2 | 1.7E−03 |
| 580 | D13630 | | BZW1 | basic leucine zipper and W2 domains 1 | 1.7E−03 |
| 581 | X15880 | NM_001848 | COL6A1 | collagen, type VI, alpha 1 | 1.7E−03 |
| 582 | AB003723 | | PIGQ | phosphatidylinositol glycan, class Q | 1.7E−03 |
| 583 | L36645 | | EPHA4 | EphA4 | 1.7E−03 |
| 584 | BF974358 | | RPS27 | ribosomal protein S27 (metallopanstimulin 1) | 1.8E−03 |
| 585 | AA747449 | | HIP2 | huntingtin interacting protein 2 | 1.9E−03 |
| 586 | AA283813 | | FLJ12150 | hypothetical protein FLJ12150 | 2.0E−03 |
| 587 | L38995 | NM_003321 | TUFM | Tu translation elongation factor, mitochondrial | 2.0E−03 |
| 588 | N67293 | | EST | *Homo sapiens* cDNA FLJ11997 fis, clone HEMBB1001458. | 2.1E−03 |
| 589 | AB014549 | | KIAA0649 | KIAA0649 gene product | 2.1E−03 |
| 590 | D38305 | | TOB1 | transducer of ERBB2, 1 | 2.2E−03 |

TABLE 10-continued

List of genes with altered expression between well and poorly differentiated type in single case

| BRC NO. | ACCESSION NO. | | Symbol | TITLE | p-value |
|---|---|---|---|---|---|
| 591 | L40391 | NM_006827 | TMP21 | transmembrane trafficking protein | 2.2E−03 |
| 592 | H28960 | | EST | ESTs | 2.2E−03 |
| 593 | U86753 | | CDC5L | CDC5 cell division cycle 5-like (S. pombe) | 2.3E−03 |
| 594 | AI143226 | | BLP1 | BBP-like protein 1 | 2.3E−03 |
| 595 | M57730 | | EFNA1 | ephrin-A1 | 2.3E−03 |
| 596 | AI928868 | | UBR1 | ubiquitin protein ligase E3 component n-recognin 1 | 2.3E−03 |
| 597 | AF077044 | | RPAC2 | likely ortholog of mouse RNA polymerase 1-3 (16 kDa subunit) | 2.3E−03 |
| 598 | AF097431 | | LEPRE1 | leucine proline-enriched proteoglycan (leprecan) 1 | 2.4E−03 |
| 599 | NM_004350 | | RUNX3 | runt-related transcription factor 3 | 2.4E−03 |
| 600 | AL162047 | | NCOA4 | nuclear receptor coactivator 4 | 2.5E−03 |
| 601 | BF915013 | | EST | Homo sapiens cDNA FLJ37302 fis, clone BRAMY2016009. | 2.5E−03 |
| 602 | Z37166 | | BAT1 | HLA-B associated transcript 1 | 2.5E−03 |
| 603 | M81349 | | SAA4 | serum amyloid A4, constitutive | 2.6E−03 |
| 604 | AL137338 | NM_007214 | SEC63L | SEC63 protein | 2.6E−03 |
| 605 | AI745624 | | ELL2 | ELL-related RNA polymerase II, elongation factor | 2.6E−03 |
| 606 | BG167522 | | HSPC016 | hypothetical protein HSPC016 | 2.6E−03 |
| 607 | U58766 | | TSTA3 | tissue specific transplantation antigen P35B | 2.7E−03 |
| 608 | J04474 | NM_000709 | BCKDHA | branched chain keto acid dehydrogenase E1, alpha polypeptide (maple syrup urine disease) | 2.7E−03 |
| 609 | H15977 | NM_021116 | EST | Homo sapiens cDNA FLJ30781 fis, clone FEBRA2000874. | 2.8E−03 |
| 610 | AL049339 | NM_001304 | CPD | carboxypeptidase D | 2.8E−03 |
| 611 | AL133555 | NM_080821 | C20orf108 | chromosome 20 open reading frame 108 | 2.9E−03 |
| 612 | AW662518 | | FLJ10876 | hypothetical protein FLJ10876 | 2.9E−03 |
| 613 | BE883507 | NM_003663 | CGGBP1 | CGG triplet repeat binding protein 1 | 2.9E−03 |
| 614 | BE797472 | | RPL17 | ribosomal protein L17 | 3.0E−03 |
| 615 | U41371 | | SF3B2 | splicing factor 3b, subunit 2, 145 kDa | 3.0E−03 |
| 616 | L39068 | | DHPS | deoxyhypusine synthase | 3.1E−03 |
| 617 | NM_004517 | | ILK | integrin-linked kinase | 3.1E−03 |
| 618 | U14972 | | RPS10 | ribosomal protein S10 | 3.2E−03 |
| 619 | U61500 | | TMEM1 | transmembrane protein 1 | 3.3E−03 |
| 620 | NM_002719 | | PPP2R5C | protein phosphatase 2, regulatory subunit B (B56), gamma isoform | 3.3E−03 |
| 621 | AF053233 | | VAMP8 | vesicle-associated membrane protein 8 (endobrevin) | 3.3E−03 |
| 622 | NM_002822 | NM_198974 | PTK9 | PTK9 protein tyrosine kinase 9 | 3.3E−03 |
| 623 | U16996 | | DUSP5 | dual specificity phosphatase 5 | 3.3E−03 |
| 624 | AV705747 | NM_006276 | SFRS7 | splicing factor, arginine/serine-rich 7, 35 kDa | 3.3E−03 |
| 625 | AF178984 | | IER5 | immediate early response 5 | 3.3E−03 |
| 626 | Z29093 | | DDR1 | discoidin domain receptor family, member 1 | 3.3E−03 |
| 627 | AB024536 | | ISLR | immunoglobulin superfamily containing leucine-rich repeat | 3.3E−03 |
| 628 | BF791601 | | EMP2 | epithelial membrane protein 2 | 3.3E−03 |
| 629 | AF061737 | | SPC18 | signal peptidase complex (18 kD) | 3.3E−03 |
| 630 | AB002386 | | EZH1 | enhancer of zeste homolog 1 (Drosophila) | 3.5E−03 |
| 631 | AA634090 | | EST | Homo sapiens, Similar to heterogeneous nuclear ribonucleoprotein A1, clone IMAGE: 2900557, mRNA | 3.5E−03 |
| 632 | AK023674 | | FLJ13612 | likely ortholog of neuronally expressed calcium binding protein | 3.6E−03 |
| 633 | D13626 | | GPR105 | G protein-coupled receptor 105 | 3.7E−03 |
| 634 | AK026849 | XM_371844 | TSPYL | TSPY-like | 3.8E−03 |
| 635 | Y18643 | | METTL1 | methyltransferase-like 1 | 3.9E−03 |
| 636 | AF176699 | | FBXL4 | F-box and leucine-rich repeat protein 4 | 3.9E−03 |
| 637 | NM_003977 | | AIP | aryl hydrocarbon receptor interacting protein | 3.9E−03 |
| 638 | AK000498 | | HARS | histidyl-tRNA synthetase | 4.0E−03 |
| 639 | U05237 | NM_004459 | FALZ | fetal Alzheimer antigen | 4.0E−03 |
| 640 | BF696304 | NM_032832 | FLJ14735 | hypothetical protein FLJ14735 | 4.0E−03 |
| 641 | X14420 | | COL3A1 | collagen, type III, alpha 1 (Ehlers-Danlos syndrome type IV, autosomal dominant) | 4.1E−03 |

TABLE 10-continued

List of genes with altered expression between well and poorly differentiated type in single case

| BRC NO. | ACCESSION NO. | | Symbol | TITLE | p-value |
|---|---|---|---|---|---|
| 642 | BE796098 | | NDUFS8 | NADH dehydrogenase (ubiquinone) Fe—S protein 8, 23 kDa (NADH-coenzyme Q reductase) | 4.3E−03 |
| 643 | X60221 | | ATP5F1 | ATP synthase, H+ transporting, mitochondrial F0 complex, subunit b, isoform 1 | 4.4E−03 |
| 644 | AA135341 | NM_021078 | GCN5L2 | GCN5 general control of amino-acid synthesis 5-like 2 (yeast) | 4.6E−03 |
| 645 | AF009368 | | CREB3 | cAMP responsive element binding protein 3 (luman) | 4.7E−03 |
| 646 | BF970013 | | SPC12 | signal peptidase 12 kDa | 4.7E−03 |
| 647 | W45522 | | ATPIF1 | ATPase inhibitory factor 1 | 4.7E−03 |
| 648 | AI733356 | NM_006306 | EST | Homo sapiens cDNA FLJ31746 fis, clone NT2RI2007334. | 4.8E−03 |
| 649 | AW117927 | | EIF3S9 | eukaryotic translation initiation factor 3, subunit 9 eta, 116 kDa | 4.8E−03 |
| 650 | AF275798 | NM_012073 | CCT5 | chaperonin containing TCP1, subunit 5 (epsilon) | 5.0E−03 |
| 651 | AI937126 | | WTAP | Wilms' tumour 1-associating protein | 5.0E−03 |
| 652 | AK024891 | NM_203463 | LOC253782 | hypothetical protein LOC253782 | 5.1E−03 |
| 653 | D13629 | | KTN1 | kinectin 1 (kinesin receptor) | 5.2E−03 |
| 654 | AI682994 | | AHCYL1 | S-adenosylhomocysteine hydrolase-like 1 | 5.3E−03 |
| 655 | BF980325 | NM_005742 | ATP6V1C2 | ATPase, H+ transporting, lysosomal 42 kDa, V1 subunit C isoform 2 | 5.3E−03 |
| 656 | AI378996 | NM_005381 | NCL | nucleolin | 5.3E−03 |
| 657 | D88153 | | HYA22 | HYA22 protein | 5.3E−03 |
| 658 | S67310 | | BF | B-factor, properdin | 5.4E−03 |
| 659 | AW438585 | | EST | Homo sapiens, clone IMAGE: 5273745, mRNA | 5.4E−03 |
| 660 | M12267 | | OAT | ornithine aminotransferase (gyrate atrophy) | 5.5E−03 |
| 661 | AB001636 | | DDX15 | DEAD/H (Asp-Glu-Ala-Asp/His) box polypeptide 15 | 5.7E−03 |
| 662 | D13315 | | GLO1 | glyoxalase I | 5.9E−03 |
| 663 | AF244931 | | WDR10 | WD repeat domain 10 | 5.9E−03 |
| 664 | AL050094 | | IDH3B | isocitrate dehydrogenase 3 (NAD+) beta | 6.0E−03 |
| 665 | AK022881 | | KIAA1272 | KIAA1272 protein | 6.0E−03 |
| 666 | AI720096 | | RPL29 | ribosomal protein L29 | 6.1E−03 |
| 667 | Y12781 | | TBL1X | transducin (beta)-like 1X-linked | 6.2E−03 |
| 668 | AI014538 | NM_138384 | LOC92170 | hypothetical protein BC004409 | 6.2E−03 |
| 669 | NM_020987 | | ANK3 | ankyrin 3, node of Ranvier (ankyrin G) | 6.3E−03 |
| 670 | NM_004387 | | NKX2-5 | NK2 transcription factor related, locus 5 (Drosophila) | 6.3E−03 |
| 671 | J03817 | | GSTM1 | glutathione S-transferase M1 | 6.3E−03 |
| 672 | BF435769 | | EST | ESTs, Weakly similar to hypothetical protein FLJ20378 [Homo sapiens] [H. sapiens] | 6.5E−03 |
| 673 | AL390147 | | DKFZp547D065 | hypothetical protein DKFZp547D065 | 6.5E−03 |
| 674 | AA961412 | NM_003333 | UBA52 | ubiquitin A-52 residue ribosomal protein fusion product 1 | 6.6E−03 |
| 675 | NM_002702 | | POU6F1 | POU domain, class 6, transcription factor 1 | 6.6E−03 |
| 676 | M58050 | | MCP | membrane cofactor protein (CD46, trophoblast-lymphocyte cross-reactive antigen) | 6.6E−03 |
| 677 | NM_001293 | | CLNS1A | chloride channel, nucleotide-sensitive, 1A | 6.7E−03 |
| 678 | BF213049 | | COX7A2 | cytochrome c oxidase subunit VIIa polypeptide 2 (liver) | 6.7E−03 |
| 679 | AF236056 | | GOLPH2 | golgi phosphoprotein 2 | 6.7E−03 |
| 680 | U79285 | NM_021079 | NMT1 | N-myristoyltransferase 1 | 6.8E−03 |
| 681 | AB027196 | | RNF10 | ring finger protein 10 | 6.9E−03 |
| 682 | AA036952 | | FLJ30973 | hypothetical protein FLJ30973 | 7.0E−03 |
| 683 | AW732157 | NM_052963 | TOP1MT | mitochondrial topoisomerase I | 7.1E−03 |
| 684 | AL049319 | NM_032804 | FLJ14547 | hypothetical protein FLJ14547 | 7.3E−03 |
| 685 | BE613161 | | EST | Homo sapiens cDNA FLJ37042 fis, clone BRACE2011947. | 7.3E−03 |
| 686 | U28749 | | HMGA2 | high mobility group AT-hook 2 | 7.3E−03 |
| 687 | BF793677 | | MGC49942 | hypothetical protein MGC49942 | 7.4E−03 |
| 688 | BG032216 | NM_017746 | FLJ20287 | hypothetical protein FLJ20287 | 7.4E−03 |
| 689 | AL449244 | | PP2447 | hypothetical protein PP2447 | 7.5E−03 |

TABLE 10-continued

List of genes with altered expression between well and poorly differentiated type in single case

| BRC NO. | ACCESSION NO. | | Symbol | TITLE | p-value |
|---|---|---|---|---|---|
| 690 | AK024103 | | EST | Homo sapiens cDNA FLJ14041 fis, clone HEMBA1005780. | 7.5E−03 |
| 691 | U17838 | | PRDM2 | PR domain containing 2, with ZNF domain | 7.5E−03 |
| 692 | D86479 | NM_001129 | AEBP1 | AE binding protein 1 | 7.5E−03 |
| 693 | D50420 | | NHP2L1 | NHP2 non-histone chromosome protein 2-like 1 (S. cerevisiae) | 7.5E−03 |
| 694 | D87258 | | PRSS11 | protease, serine, 11 (IGF binding) | 7.5E−03 |
| 695 | BF434108 | NM_014187 | HSPC171 | HSPC171 protein | 7.6E−03 |
| 696 | NM_000705 | | ATP4B | ATPase, H+/K+ exchanging, beta polypeptide | 7.7E−03 |
| 697 | AF077599 | | SBB103 | hypothetical SBBI03 protein | 7.7E−03 |
| 698 | NM_001530 | | HIF1A | hypoxia-inducible factor 1, alpha subunit (basic helix-loop-helix transcription factor) | 7.8E−03 |
| 699 | AB023204 | | EPB41L3 | erythrocyte membrane protein band 4.1-like 3 | 7.8E−03 |
| 700 | AA253194 | NM_022121 | PIGPC1 | p53-induced protein PIGPC1 | 7.9E−03 |
| 701 | BE502341 | NM_139177 | C17orf26 | chromosome 17 open reading frame 26 | 7.9E−03 |
| 702 | AL050265 | | TARDBP | TAR DNA binding protein | 8.0E−03 |
| 703 | AK001643 | NM_018215 | FLJ10781 | hypothetical protein FLJ10781 | 8.3E−03 |
| 704 | BG179412 | | COX7B | cytochrome c oxidase subunit VIIb | 8.6E−03 |
| 705 | X03212 | | KRT7 | keratin 7 | 8.8E−03 |
| 706 | L07033 | | HMGCL | 3-hydroxymethyl-3-methylglutaryl-Coenzyme A lyase (hydroxymethylglutaricaciduria) | 9.0E−03 |
| 707 | M19383 | | ANXA4 | annexin A4 | 9.0E−03 |
| 708 | NM_001273 | | CHD4 | chromodomain helicase DNA binding protein 4 | 9.1E−03 |
| 709 | NM_004461 | | FARSL | phenylalanine-tRNA synthetase-like | 9.1E−03 |
| 710 | AI192880 | | CD44 | CD44 antigen (homing function and Indian blood group system) | 9.1E−03 |
| 711 | AF038961 | | MPDU1 | mannose-P-dolichol utilization defect 1 | 9.5E−03 |
| 712 | U67322 | | C20orf18 | chromosome 20 open reading frame 18 | 9.5E−03 |
| 713 | AA521017 | | EST | EST | 9.5E−03 |
| 714 | AA811043 | NM_003730 | RNASE6PL | ribonuclease 6 precursor | 9.9E−03 |
| 715 | AA536113 | | TMEPAI | transmembrane, prostate androgen induced RNA | 9.9E−03 |
| 716 | BF973104 | | LOC201725 | hypothetical protein LOC201725 | 9.9E−03 |
| 717 | NM_000293 | | PHKB | phosphorylase kinase, beta | 9.9E−03 |
| 718 | NM_000548 | | TSC2 | tuberous sclerosis 2 | 1.0E−02 |

TABLE 11

List of genes with altered expression between node-positive and node-negative tumors

| BRC NO. | ACCESSION NO. | | Symbol | TITLE | P-value | + or − |
|---|---|---|---|---|---|---|
| 719 | BF686125 | | UBA52 | ubiquitin A-52 residue ribosomal protein fusion product 1 | 8.1E−09 | − |
| 720 | AA634090 | | | Homo sapiens, Similar to heterogeneous nuclear ribonucleoprotein A1, clone IMAGE: 2900557, mRNA | 1.4E−07 | − |
| 721 | L00692 | | CEACAM3 | carcinoembryonic antigen-related cell adhesion molecule 3 | 4.2E−07 | − |
| 722 | AW954403 | NM_004781 | VAMP3 | vesicle-associated membrane protein 3 (cellubrevin) | 2.2E−06 | + |
| 723 | AA865619 | | C21orf97 | chromosome 21 open reading frame 97 | 2.6E−06 | − |
| 724 | W74502 | NM_032350 | MGC11257 | hypothetical protein MGC11257 | 2.4E−05 | + |
| 725 | NM_002094 | | GSPT1 | G1 to S phase transition 1 | 2.7E−05 | + |
| 726 | T55178 | | KIAA1040 | KIAA1040 protein | 3.2E−05 | − |
| 727 | L36983 | | DNM2 | dynamin 2 | 4.1E−05 | + |
| 728 | Z21507 | | EEF1D | eukaryotic translation elongation factor 1 delta (guanine nucleotide exchange protein) | 5.2E−05 | − |
| 729 | AI581728 | NM_005507 | CFL1 | cofilin 1 (non-muscle) | 8.0E−05 | + |

TABLE 11-continued

List of genes with altered expression between node-positive and node-negative tumors

| BRC NO. | ACCESSION NO. | | Symbol | TITLE | P-value | + or − |
|---|---|---|---|---|---|---|
| 730 | NM_001293 | | CLNS1A | chloride channel, nucleotide-sensitive, 1A | 9.0E−05 | + |
| 731 | BF680847 | | SENP2 | sentrin-specific protease | 9.0E−05 | + |
| 732 | AF100743 | | NDUFS3 | NADH dehydrogenase (ubiquinone) Fe—S protein 3, 30 kDa (NADH-coenzyme Q reductase) | 9.8E−05 | + |
| 733 | NM_004960 | | FUS | fusion, derived from t(12; 16) malignant liposarcoma | 9.8E−05 | − |
| 734 | AK023975 | NM_015934 | NOP5/NOP58 | nucleolar protein NOP5/NOP58 | 1.3E−04 | + |
| 735 | AF083245 | | PSMD13 | proteasome (prosome, macropain) 26S subunit, non-ATPase, 13 | 1.5E−04 | + |
| 736 | AA129776 | | SUOX | sulfite oxidase | 1.8E−04 | + |
| 737 | U55766 | NM_007043 | HRB2 | HIV-1 rev binding protein 2 | 2.0E−04 | + |
| 738 | BF526092 | | LOC154467 | hypothetical protein BC003515 | 2.1E−04 | + |
| 739 | BF677579 | XM_370754 | THTPA | thiamine triphosphatase | 2.3E−04 | + |
| 740 | X98260 | | ZRF1 | zuotin related factor 1 | 2.3E−04 | + |
| 741 | BE440010 | | LOC51255 | hypothetical protein LOC51255 | 2.7E−04 | + |
| 742 | AF007165 | NM_021008 | DEAF1 | deformed epidermal autoregulatory factor 1 (*Drosophila*) | 2.7E−04 | + |
| 743 | X78687 | | NEU1 | sialidase 1 (lysosomal sialidase) | 3.0E−04 | + |
| 744 | AW965200 | | | *Homo sapiens*, clone IMAGE: 5286019, mRNA | 3.1E−04 | − |
| 745 | AK023240 | | UGCGL1 | UDP-glucose ceramide glucosyltransferase-like 1 | 3.1E−04 | + |
| 746 | M95712 | | BRAF | v-raf murine sarcoma viral oncogene homolog B1 | 3.7E−04 | + |
| 747 | L38995 | NM_003321 | TUFM | Tu translation elongation factor, mitochondrial | 3.9E−04 | + |
| 748 | AW014268 | | FLJ10726 | hypothetical protein FLJ10726 | 4.2E−04 | + |
| 749 | D49547 | | DNAJB1 | DnaJ (Hsp40) homolog, subfmaily B, member 1 | 4.4E−04 | + |
| 750 | BE466450 | | AP4S1 | adaptor-related protein complex 4, sigma 1 subunit | 4.5E−04 | + |
| 751 | AB007944 | | KIAA0475 | KIAA0475 gene product | 4.9E−04 | − |
| 752 | AF034091 | | MRPL40 | mitochondrial ribosomal protein L40 | 5.1E−04 | + |

TABLE 12

Histoclinical information

| ID | age in operation | memo pause status | T | N | M | Stage | Histrogical type | Lymphocytic infiltrate | Angioinvasion | ER | PgR |
|---|---|---|---|---|---|---|---|---|---|---|---|
| MMK010003 | 51 | pre | 2 | 1 | 0 | 2 | a3 | 3 | 0 | + | + |
| MMK010004 | 47 | pre | 2 | 1 | 0 | 2 | a1 | 0 | 0 | + | + |
| MMK010005 | 44 | pre | 2 | 0 | 0 | 2 | a1 | 1 | 0 | + | + |
| MMK010013 | 45 | pre | 2 | 1 | 0 | 2 | a1 | 1 | 0 | − | − |
| MMK010016 | 44 | pre | 2 | 0 | 0 | 2 | a2 | 0 | 0 | − | − |
| MMK010025 | 46 | pre | 2 | 0 | 0 | 2 | a1 | 0 | 0 | + | − |
| MMK010031 | 29 | pre | 2 | 2 | 0 | 3 | a3 | 3 | 0 | − | − |
| MMK010037 | 62 | post | 0 | 0 | 0 | 0 | Ia | 0 | 0 | + | + |
| MMK010042 | 47 | pre | 2 | 1 | 0 | 2 | a3 | 1 | 2 | + | + |
| MMK010086 | 42 | pre | 2 | 0 | 0 | 2 | a1 | 0 | 0 | + | + |
| MMK010102 | 51 | pre | 2 | 1 | 0 | 3 | a2 | 3 | 0 | + | + |
| MMK010110 | 39 | pre | 2 | 0 | 0 | 2 | a1 | 2 | 0 | − | − |
| MMK010129 | 52 | pre | 2 | 2 | 0 | 3 | a1 | 2 | 0 | − | − |
| MMK010135 | 41 | pre | 2 | 0 | 0 | 2 | a1 | 0 | 0 | + | + |
| MMK010138 | 38 | pre | 2 | 0 | 0 | 2 | a1 | 0 | 0 | + | + |
| MMK010145 | 51 | pre | 2 | 1 | 0 | 2 | a3 | 0 | 0 | + | + |
| MMK010147 | 49 | pre | 2 | 1 | 0 | 2 | a1 | 1 | 0 | + | + |
| MMK010149 | 35 | pre | 2 | 0 | 0 | 2 | a3 | 1 | 0 | − | − |
| MMK010175 | 38 | pre | 2 | 0 | 0 | 2 | a3 | 0 | 0 | + | + |
| MMK010178 | 51 | pre | 0 | 0 | 0 | 0 | Ia | 0 | 0 | + | + |
| MMK010207 | 40 | pre | 2 | 0 | 0 | 2 | a1 | 0 | 0 | + | + |
| MMK010214 | 42 | pre | 2 | 1 | 0 | 2 | a1 | 0 | 0 | − | − |
| MMK010247 | 48 | pre | 2 | 1 | 0 | 2 | a2 | 3 | 0 | − | − |
| MMK010252 | 52 | pre | 2 | 1 | 0 | 2 | a2 | 0 | 0 | − | − |
| MMK010255 | 47 | pre | 2 | 0 | 0 | 2 | a2 | 0 | 0 | − | − |
| MMK010302 | 46 | pre | 2 | 1 | 0 | 2 | a2 | 2 | 1 | − | − |

TABLE 12-continued

| | | Histoclinical information | | | | | | | | | |
|---|---|---|---|---|---|---|---|---|---|---|---|
| ID | age in operation | memo pause status | T | N | M | Stage | Histrogical type | Lymphocytic infiltrate | Angioinvasion | ER | PgR |
| MMK010304 | 48 | pre | 2 | 1 | 0 | 2 | a3 | 1 | 0 | + | + |
| MMK010326 | 53 | post | 0 | 0 | 0 | 0 | Ia | 0 | 0 | − | − |
| MMK010327 | 43 | pre | 2 | 1 | 0 | 2 | a1 | 1 | 1 | + | + |
| MMK010341 | 42 | pre | 2 | 1 | 0 | 2 | a1 | 2 | 0 | + | + |
| MMK010370 | 46 | pre | 2 | 1 | 0 | 2 | a3 | 2 | 0 | + | + |
| MMK010397 | 38 | pre | 2 | 1 | 0 | 2 | a3 | 3 | 2 | + | + |
| MMK010411 | 46 | pre | 2 | 0 | 0 | 2 | a1 | 0 | 0 | + | + |
| MMK010431 | 50 | pre | 2 | 0 | 0 | 2 | a3 | 0 | 0 | − | − |
| MMK010435 | 49 | pre | 2 | 1 | 0 | 2 | a3 | 0 | 0 | + | + |
| MMK010453 | 49 | pre | 2 | 1 | 0 | 2 | a3 | 3 | 0 | + | + |
| MMK010471 | 42 | pre | 2 | 1 | 0 | 2 | a1 | 3 | 0 | − | − |
| MMK010473 | 40 | pre | 2 | 1 | 0 | 2 | a2 | 0 | 0 | − | − |
| MMK010478 | 38 | pre | 2 | 2 | 0 | 3 | a2 | 0 | 0 | + | + |
| MMK010491 | 46 | pre | 2 | 0 | 0 | 2 | a3 | 1 | 0 | + | + |
| MMK010497 | 44 | pre | 0 | 0 | 0 | 0 | Ia | 0 | 0 | − | + |
| MMK010500 | 45 | pre | 2 | 0 | 0 | 2 | a1 | 0 | 0 | + | + |
| MMK010502 | 51 | pre | 2 | 0 | 0 | 2 | a2 | 0 | 0 | − | − |
| MMK010508 | 51 | pre | 2 | 1 | 0 | 2 | a2 | 0 | 0 | − | − |
| MMK010521 | 21 | pre | 2 | 0 | 0 | 2 | a1 | 1 | 1 | − | − |
| MMK010552 | 49 | pre | 2 | 0 | 0 | 2 | a2 | 0 | 0 | − | − |
| MMK010554 | 51 | pre | 2 | 0 | 0 | 2 | a3 | 2 | 0 | + | + |
| MMK010571 | 45 | pre | 2 | 1 | 1 | 4 | a3 | 3 | 0 | + | + |
| MMK010591 | 40 | pre | 0 | 0 | 0 | 0 | Ia | 0 | 0 | − | + |
| MMK010613 | 37 | pre | 0 | 0 | 0 | 0 | Ia | 0 | 0 | − | + |
| MMK010623 | 39 | pre | 2 | 1 | 0 | 2 | a1 | 3 | 0 | + | + |
| MMK010624 | 39 | pre | 2 | 1 | 0 | 2 | a1 | 3 | 0 | + | + |
| MMK010626 | 48 | pre | 2 | 0 | 0 | 2 | a1 | 1 | 1 | − | − |
| MMK010631 | 41 | pre | 2 | 0 | 0 | 2 | a1 | 0 | 0 | + | + |
| MMK010640 | 35 | pre | 0 | 0 | 0 | 0 | Ia | 0 | 0 | + | + |
| MMK010644 | 47 | pre | 2 | 2 | 0 | 2 | a3 | 3 | 0 | + | + |
| MMK010646 | 37 | pre | 2 | 1 | 0 | 2 | a3 | 1 | 0 | + | + |
| MMK010660 | 46 | pre | 2 | 0 | 0 | 2 | a1 | 0 | 0 | − | − |
| MMK010671 | 45 | pre | 2 | 0 | 0 | 2 | a1 | 0 | 0 | − | − |
| MMK010679 | 68 | post | 0 | 0 | 0 | 0 | Ia | 0 | 0 | + | + |
| MMK010680 | 58 | post | 0 | 0 | 0 | 0 | Ia | 0 | 0 | − | + |
| MMK010709 | 33 | pre | 2 | 0 | 0 | 2 | a3 | 0 | 2 | − | − |
| MMK010711 | 51 | pre | 0 | 0 | 0 | 0 | Ia | 0 | 0 | − | + |
| MMK010724 | 40 | pre | 2 | 1 | 0 | 2 | a3 | 3 | 2 | + | + |
| MMK010744 | 41 | pre | 0 | 0 | 0 | 0 | Ia | 0 | 0 | + | + |
| MMK010758 | 40 | pre | 2 | 1 | 0 | 2 | a1 | 0 | 1 | + | + |
| MMK010760 | 42 | pre | 2 | 0 | 0 | 2 | a1 | 0 | 0 | + | + |
| MMK010762 | 50 | pre | 2 | 1 | 0 | 2 | a3 | 3 | 1 | + | + |
| MMK010769 | 33 | pre | 2 | 0 | 0 | 2 | a2 | 0 | 0 | − | − |
| MMK010772 | 45 | pre | 2 | 1 | 0 | 2 | a3 | 2 | 0 | − | − |
| MMK010779 | 46 | pre | 2 | 1 | 0 | 2 | a2 | 0 | 1 | − | − |
| MMK010780 | 31 | pre | 2 | 0 | 0 | 2 | a2 | 0 | 0 | − | − |
| MMK010781 | 44 | pre | 2 | 0 | 0 | 2 | a3 | 0 | 2 | + | + |
| MMK010794 | 52 | pre | 2 | 1 | 0 | 2 | a3 | 2 | 1 | + | + |
| MMK010818 | 51 | pre | 2 | 0 | 0 | 2 | a1 | 0 | 2 | + | + |
| MMK010835 | 42 | pre | 0 | 0 | 0 | 0 | Ia | 0 | 0 | + | + |
| MMK010846 | 47 | pre | 2 | 0 | 0 | 2 | a1 | 0 | 0 | + | + |
| MMK010858 | 42 | pre | 2 | 1 | 0 | 2 | a3 | 2 | 3 | + | + |
| MMK010864 | 52 | pre | 2 | 1 | 0 | 2 | a1 | 0 | 1 | − | − |
| MMK010869 | 45 | pre | 2 | 0 | 0 | 2 | a1 | 0 | 1 | − | − |
| MMK010903 | 47 | pre | 2 | 0 | 0 | 2 | a1 | 0 | 0 | + | + |

TABLE 13

| | | |
|---|---|---|
| Si1-F | 5'-CACCGAACGATATAAAGCCAGCCTTCAAGAGAGG CTGGCTTTATATCGTTC-3' | SEQ ID NO. 23 |
| Si1-R | 5'-AAAAGAACGATATAAAGCCAGCCTCTCTTGAAGG CTGGCTTTATATCGTTC-3' | SEQ ID NO. 24 |
| Si1-Target | 5'-GAACGATATAAAGCCAGCC-3' | SEQ ID NO. 25 |
| Si3-F | 5'-CACCCTGGATGAATCATACCAGATTCAAGAGATC TGGTATGATTCATCCAG-3' | SEQ ID NO. 26 |
| Si3-R | 5'-AAAACTGGATGAATCATACCAGATCTCTTGAATC TGGTATGATTCATCCAG-3' | SEQ ID NO. 27 |
| Si3-Target | 5'-CTGGATGAATCATACCAGA-3' | SEQ ID NO. 28 |
| Si4-F | 5'-CACCGTGTGGCTTGCGTAAATAATTCAAGAGAT TATTTACGCAAGCCACAC-3' | SEQ ID NO. 29 |
| Si4-R | 5'-AAAAGTGTGGCTTGCGTAAATAATCTCTTGAAT TATTTACGCAAGCCACAC-3' | SEQ ID NO. 30 |
| Si4-Target | 5'-GTGTGGCTTGCGTAAATAA-3' | SEQ ID NO. 31 |

INDUSTRIAL APPLICABILITY

The gene-expression analysis of breast cancer described herein, obtained through a combination of laser-capture dissection and genome-wide cDNA microarray, has identified specific genes as targets for cancer prevention and therapy. Based on the expression of a subset of these differentially expressed genes, the present invention provides molecular diagnostic markers for identifying and detecting breast cancer.

The methods described herein are also useful in the identification of additional molecular targets for prevention, diagnosis and treatment of breast cancer. The data reported herein add to a comprehensive understanding of breast cancer, facilitate development of novel diagnostic strategies, and provide clues for identification of molecular targets for therapeutic drugs and preventative agents. Such information contributes to a more profound understanding of breast tumorigenesis, and provide indicators for developing novel strategies for diagnosis, treatment, and ultimately prevention of breast cancer.

All patents, patent applications, and publications cited herein are incorporated by reference in their entirety.

Furthermore, while the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

---

The invention claimed is:

1. A composition for treating or preventing breast cancer, said composition comprising a pharmaceutically effective amount of an siRNA against a T-LAK cell-originated protein kinase (TOPK) polynucleotide, wherein the target sequence of said siRNA comprises the sense strand comprising a nucleotide sequence selected from the group consisting of nucleotide sequences of SEQ ID NO: 28 and 31.

* * * * *

SEQUENCE LISTING

```
<160> NUMBER OF SEQ ID NOS: 52

<210> SEQ ID NO 1
<211> LENGTH: 23
<212> TYPE: DNA
<213> ORGANISM: Artificial Sequence
<220> FEATURE:
<223> OTHER INFORMATION: synthetic semi-quantitative RT-PCR EST MSTP020
      (MST020) qk10f03.x1 NCI_CGAP_Kid3 clone IMAGE:1868573 3', BRC No.
       147 forward primer

<400> SEQUENCE: 1
ctgttctggc ttcgttatgt tct                                              23

<210> SEQ ID NO 2
<211> LENGTH: 23
<212> TYPE: DNA
<213> ORGANISM: Artificial Sequence
<220> FEATURE:
<223> OTHER INFORMATION: synthetic semi-quantitative RT-PCR EST MSTP020
      (MST020) qk10f03.x1 NCI_CGAP_Kid3 clone IMAGE:1868573 3', BRC No.
       147 reverse primer

<400> SEQUENCE: 2
agaaaatacg gtcctcttgt tgc                                              23

<210> SEQ ID NO 3
<211> LENGTH: 22
<212> TYPE: DNA
<213> ORGANISM: Artificial Sequence
<220> FEATURE:
<223> OTHER INFORMATION: synthetic semi-quantitative RT-PCR adaptor-
      related protein complex 1, sigma 2 subunit (AP1S2), zq66c06.s1
      Stratagene neuroepithelium (#937231) clone IMAGE:6436570 3' BRC
      No. 398 forward primer
```

<400> SEQUENCE: 3
cactgtaatg cacgacattt ga                                            22

<210> SEQ ID NO 4
<211> LENGTH: 23
<212> TYPE: DNA
<213> ORGANISM: Artificial Sequence
<220> FEATURE:
<223> OTHER INFORMATION: synthetic semi-quantitative RT-PCR adaptor-
      related protein complex 1, sigma 2 subunit (AP1S2), zq66c06.s1
      Stratagene neuroepithelium (#937231) clone IMAGE:6436570 3' BRC
      No. 398 reverse primer

<400> SEQUENCE: 4
gttacagctt agcacaaggc atc                                           23

<210> SEQ ID NO 5
<211> LENGTH: 22
<212> TYPE: DNA
<213> ORGANISM: Artificial Sequence
<220> FEATURE:
<223> OTHER INFORMATION: synthetic semi-quantitative RT-PCR hypothetical
      protein LOC253782, zp06c06.s1 Stratagene ovarian cancer (#937219)
      BRC No. 161 forward primer

<400> SEQUENCE: 5
acctctgagt ttgatttccc aa                                            22

<210> SEQ ID NO 6
<211> LENGTH: 23
<212> TYPE: DNA
<213> ORGANISM: Artificial Sequence
<220> FEATURE:
<223> OTHER INFORMATION: synthetic semi-quantitative RT-PCR hypothetical
      protein LOC253782, zp06c06.s1 Stratagene ovarian cancer (#937219)
      BRC No. 161 reverse primer

<400> SEQUENCE: 6
cgaggcttgt aacaatctac tgg                                           23

<210> SEQ ID NO 7
<211> LENGTH: 23
<212> TYPE: DNA
<213> ORGANISM: Artificial Sequence
<220> FEATURE:
<223> OTHER INFORMATION: synthetic semi-quantitative RT-PCR EST
      zj54b05.s1 Soares_fetal_liver_spleen 1NFLS_S1 clone IMAGE:
      454065 3' BRC No. 135 forward primer

<400> SEQUENCE: 7
gaaactgtac gggggttaaa gag                                           23

<210> SEQ ID NO 8
<211> LENGTH: 23
<212> TYPE: DNA
<213> ORGANISM: Artificial Sequence
<220> FEATURE:
<223> OTHER INFORMATION: synthetic semi-quantitative RT-PCR EST
      zj54b05.s1 Soares_fetal_liver_spleen 1NFLS_S1 clone IMAGE:
      454065 3' BRC No. 135 reverse primer

<400> SEQUENCE: 8
catcaatgtg gtgagtgaca tct                                           23

<210> SEQ ID NO 9
<211> LENGTH: 23
<212> TYPE: DNA
<213> ORGANISM: Artificial Sequence

```
<220> FEATURE:
<223> OTHER INFORMATION: synthetic semi-quantitative RT-PCR dachshund
      (Drosphila) homolog (DACH, DACH1), FLJ10138, ym5310.s1 Soares
      infant brain 1NIB clone IMAGE:52021 3' BRC No. 395 forward primer

<400> SEQUENCE: 9
aagcccttgg aacagaacat act                                            23

<210> SEQ ID NO 10
<211> LENGTH: 23
<212> TYPE: DNA
<213> ORGANISM: Artificial Sequence
<220> FEATURE:
<223> OTHER INFORMATION: synthetic semi-quantitative RT-PCR dachshund
      (Drosphila) homolog (DACH, DACH1), FLJ10138, ym5310.s1 Soares
      infant brain 1NIB clone IMAGE:52021 3' BRC No. 395 reverse primer

<400> SEQUENCE: 10
cagtaaacgt ggttctcaca ttg                                            23

<210> SEQ ID NO 11
<211> LENGTH: 20
<212> TYPE: DNA
<213> ORGANISM: Artificial Sequence
<220> FEATURE:
<223> OTHER INFORMATION: synthetic semi-quantitative RT-PCR internal
      control glyceraldehyde-3-phosphate dehydrogenase (GAPD, GAPDH,
      G3PD), MGC88685, aging-associated gene 9 protein forward primer

<400> SEQUENCE: 11
cgaccacttt gtcaagctca                                                20

<210> SEQ ID NO 12
<211> LENGTH: 23
<212> TYPE: DNA
<213> ORGANISM: Artificial Sequence
<220> FEATURE:
<223> OTHER INFORMATION: synthetic semi-quantitative RT-PCR internal
      control glyceraldehyde-3-phosphate dehydrogenase (GAPD, GAPDH,
      G3PD), MGC88685, aging-associated gene 9 protein forward primer

<400> SEQUENCE: 12
ggttgagcac agggtacttt att                                            23

<210> SEQ ID NO 13
<211> LENGTH: 23
<212> TYPE: DNA
<213> ORGANISM: Artificial Sequence
<220> FEATURE:
<223> OTHER INFORMATION: synthetic semi-quantitative RT-PCR T-LAK cell-
      originated protein kinase (TOPK), spermatogenesis-related protein
      kinase (SPK), PDZ binding kinase (PBK), Nori-3, FLJ14385, A7870,
      BRC No. 456 forward primer, A7870 specific probe

<400> SEQUENCE: 13
agaccctaaa gatcgtcctt ctg                                            23

<210> SEQ ID NO 14
<211> LENGTH: 23
<212> TYPE: DNA
<213> ORGANISM: Artificial Sequence
<220> FEATURE:
<223> OTHER INFORMATION: synthetic semi-quantitative RT-PCR T-LAK cell-
      originated protein kinase (TOPK), spermatogenesis-related protein
      kinase (SPK), PDZ binding kinase (PBK), Nori-3, FLJ14385, A7870,
      BRC No. 456 reverse primer, A7870 specific probe

<400> SEQUENCE: 14
gtgttttaag tcagcatgag cag                                            23
```

<210> SEQ ID NO 15
<211> LENGTH: 51
<212> TYPE: DNA
<213> ORGANISM: Artificial Sequence
<220> FEATURE:
<223> OTHER INFORMATION: synthetic scrambled control (SC) double-stranded oligonucleotide

<400> SEQUENCE: 15
tcccgcgcgc tttgtaggat tcgttcaaga gacgaatcct acaaagcgcg c        51

<210> SEQ ID NO 16
<211> LENGTH: 51
<212> TYPE: DNA
<213> ORGANISM: Artificial Sequence
<220> FEATURE:
<223> OTHER INFORMATION: synthetic scrambled control (SC) double-stranded oligonucleotide

<400> SEQUENCE: 16
aaaagcgcgc tttgtaggat tcgtctcttg aacgaatcct acaaagcgcg c        51

<210> SEQ ID NO 17
<211> LENGTH: 51
<212> TYPE: DNA
<213> ORGANISM: Artificial Sequence
<220> FEATURE:
<223> OTHER INFORMATION: synthetic luciferase control (LUC) double-stranded oligonucleotide

<400> SEQUENCE: 17
tccccgtacg cggaatactt cgattcaaga gatcgaagta ttccgcgtac g        51

<210> SEQ ID NO 18
<211> LENGTH: 51
<212> TYPE: DNA
<213> ORGANISM: Artificial Sequence
<220> FEATURE:
<223> OTHER INFORMATION: synthetic luciferase control (LUC) double-stranded oligonucleotide

<400> SEQUENCE: 18
aaaacgtacg cggaatactt cgatctcttg aatcgaagta ttccgcgtac g        51

<210> SEQ ID NO 19
<211> LENGTH: 21
<212> TYPE: DNA
<213> ORGANISM: Artificial Sequence
<220> FEATURE:
<223> OTHER INFORMATION: synthetic semi-quantitative RT-PCR internal control glyceraldehyde-3-phosphate dehydrogenase (GAPD, GAPDH, G3PD) specific primer

<400> SEQUENCE: 19
atggaaatcc catcaccatc t                                         21

<210> SEQ ID NO 20
<211> LENGTH: 23
<212> TYPE: DNA
<213> ORGANISM: Artificial Sequence
<220> FEATURE:
<223> OTHER INFORMATION: synthetic semi-quantitative RT-PCR internal control glyceraldehyde-3-phosphate dehydrogenase (GAPD, GAPDH, G3PD) specific primer

<400> SEQUENCE: 20
ggttgagcac agggtacttt att                                       23

```
<210> SEQ ID NO 21
<211> LENGTH: 20
<212> TYPE: DNA
<213> ORGANISM: Artificial Sequence
<220> FEATURE:
<223> OTHER INFORMATION: synthetic semi-quantitative RT-PCR A7870
      specific primer

<400> SEQUENCE: 21
gccttcatca tccaaacatt                                                  20

<210> SEQ ID NO 22
<211> LENGTH: 20
<212> TYPE: DNA
<213> ORGANISM: Artificial Sequence
<220> FEATURE:
<223> OTHER INFORMATION: synthetic semi-quantitative RT-PCR A7870
      specific primer

<400> SEQUENCE: 22
ggcaaatatg tctgccttgt                                                  20

<210> SEQ ID NO 23
<211> LENGTH: 51
<212> TYPE: DNA
<213> ORGANISM: Artificial Sequence
<220> FEATURE:
<223> OTHER INFORMATION: synthetic double stranded A7870-specific
      siRNA oligonucleotide Si1-F

<400> SEQUENCE: 23
caccgaacga tataaagcca gccttcaaga gaggctggct ttatatcgtt c                51

<210> SEQ ID NO 24
<211> LENGTH: 51
<212> TYPE: DNA
<213> ORGANISM: Artificial Sequence
<220> FEATURE:
<223> OTHER INFORMATION: synthetic double stranded A7870-specific
      siRNA oligonucleotide Si1-R

<400> SEQUENCE: 24
aaaagaacga tataaagcca gcctctcttg aaggctggct ttatatcgtt c                51

<210> SEQ ID NO 25
<211> LENGTH: 19
<212> TYPE: DNA
<213> ORGANISM: Artificial Sequence
<220> FEATURE:
<223> OTHER INFORMATION: synthetic A7870 (TOPK) specific target sequence
      Si1-Target

<400> SEQUENCE: 25
gaacgatata aagccagcc                                                   19

<210> SEQ ID NO 26
<211> LENGTH: 51
<212> TYPE: DNA
<213> ORGANISM: Artificial Sequence
<220> FEATURE:
<223> OTHER INFORMATION: synthetic double stranded A7870-specific siRNA
      oligonucleotide Si3-F

<400> SEQUENCE: 26
caccctggat gaatcatacc agattcaaga gatctggtat gattcatcca g                51
```

```
<210> SEQ ID NO 27
<211> LENGTH: 51
<212> TYPE: DNA
<213> ORGANISM: Artificial Sequence
<220> FEATURE:
<223> OTHER INFORMATION: synthetic double stranded A7870-specific siRNA
      oligonucleotide Si3-R

<400> SEQUENCE: 27
aaaactggat gaatcatacc agatctcttg aatctggtat gattcatcca g            51

<210> SEQ ID NO 28
<211> LENGTH: 19
<212> TYPE: DNA
<213> ORGANISM: Artificial Sequence
<220> FEATURE:
<223> OTHER INFORMATION: synthetic A7870 (TOPK) specific target sequence
      Si3-Target

<400> SEQUENCE: 28
ctggatgaat cataccaga                                                19

<210> SEQ ID NO 29
<211> LENGTH: 51
<212> TYPE: DNA
<213> ORGANISM: Artificial Sequence
<220> FEATURE:
<223> OTHER INFORMATION: synthetic double stranded A7870-specific siRNA
      oligonucleotide Si4-F

<400> SEQUENCE: 29
caccgtgtgg cttgcgtaaa taattcaaga gattatttac gcaagccaca c            51

<210> SEQ ID NO 30
<211> LENGTH: 51
<212> TYPE: DNA
<213> ORGANISM: Artificial Sequence
<220> FEATURE:
<223> OTHER INFORMATION: synthetic double stranded A7870-specific siRNA
      oligonucleotide Si4-R

<400> SEQUENCE: 30
aaaagtgtgg cttgcgtaaa taatctcttg aattatttac gcaagccaca c            51

<210> SEQ ID NO 31
<211> LENGTH: 19
<212> TYPE: DNA
<213> ORGANISM: Artificial Sequence
<220> FEATURE:
<223> OTHER INFORMATION: synthetic A7870 (TOPK) specific target sequence
      Si4-Target

<400> SEQUENCE: 31
gtgtggcttg cgtaaataa                                                19

<210> SEQ ID NO 32
<211> LENGTH: 10
<212> TYPE: RNA
<213> ORGANISM: Artificial Sequence
<220> FEATURE:
<223> OTHER INFORMATION: u nucleotides added to 3' end of antisense
      strand of target sequence
<220> FEATURE:
<221> NAME/KEY: modified_base
<222> LOCATION: (3)...(10)
<223> OTHER INFORMATION: u at positions 3-10 may be present or absent

<400> SEQUENCE: 32
uuuuuuuuuu                                                          10
```

<210> SEQ ID NO 33
<211> LENGTH: 41
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 33
gaacgauaua aagccagccc ccggcuggcu uuauaucguu c           41

<210> SEQ ID NO 34
<211> LENGTH: 42
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 34
gaacgauaua aagccagccu ucgggcuggc uuuauaucgu uc           42

<210> SEQ ID NO 35
<211> LENGTH: 43
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 35
gaacgauaua aagccagccc caccggcugg cuuuauaucg uuc           43

<210> SEQ ID NO 36
<211> LENGTH: 45
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 36
gaacgauaua aagccagccc cacaccggcu ggcuuuauau cguuc           45

<210> SEQ ID NO 37
<211> LENGTH: 47
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 37
gaacgauaua aagccagccu ucaagagagg cuggcuuuau aucguuc           47

<210> SEQ ID NO 38
<211> LENGTH: 41
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 38
cuggaugaau cauaccagac ccucuggu au gauucaucca g           41

<210> SEQ ID NO 39
<211> LENGTH: 42
<212> TYPE: RNA
<213> ORGANISM: Artificial Sequence
<220> FEATURE:
<223> OTHER INFORMATION: exemplary TOPK hairpin siRNA with loop sequence

```
<400> SEQUENCE: 39
cuggaugaau cauaccagau ucgucuggua ugauucaucc ag                    42

<210> SEQ ID NO 40
<211> LENGTH: 43
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 40
cuggaugaau cauaccagac caccucuggu augauucauc cag                   43

<210> SEQ ID NO 41
<211> LENGTH: 45
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 41
cuggaugaau cauaccagac cacaccucug guaugauuca uccag                 45

<210> SEQ ID NO 42
<211> LENGTH: 47
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 42
cuggaugaau cauaccagau caagagauc ugguaugauu cauccag                47

<210> SEQ ID NO 43
<211> LENGTH: 41
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 43
guguggcuug cguaaauaac ccuuauuuac gcaagccaca c                     41

<210> SEQ ID NO 44
<211> LENGTH: 42
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 44
guguggcuug cguaaauaau ucguuauuua cgcaagccac ac                    42

<210> SEQ ID NO 45
<211> LENGTH: 43
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 45
guguggcuug cguaaauaac caccuuauuu acgcaagcca cac                   43

<210> SEQ ID NO 46
<211> LENGTH: 45
```

```
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 46
guguggcuug cguaaauaac cacaccuuau uuacgcaagc cacac              45

<210> SEQ ID NO 47
<211> LENGTH: 47
<212> TYPE: RNA
<213> ORGANISM: Artificial Sequence
<220> FEATURE:
<223> OTHER INFORMATION: exemplary TOPK hairpin siRNA with loop sequence

<400> SEQUENCE: 47
guguggcuug cguaaauaau ucaagagauu auuuacgcaa gccacac            47

<210> SEQ ID NO 48
<211> LENGTH: 1840
<212> TYPE: DNA
<213> ORGANISM: Homo sapiens
<220> FEATURE:
<223> OTHER INFORMATION: T-LAK cell-originated protein kinase (TOPK),
      spermatogenesis-related protein kinase (SPK), PDZ
      binding kinase (PBK), Nori-3, FLJ14385, A7870, BRC
      No. 456
<220> FEATURE:
<221> NAME/KEY: CDS
<222> LOCATION: (179)..(1147)
<223> OTHER INFORMATION: T-LAK cell-originated protein kinase (TOPK)

<400> SEQUENCE: 48
ggagggttcg aattgcaacg gcagctaccg ggcgtatgtg ttggtgctag aggcagctgc    60
agggtctcgc tgggggccgc tcgggaccaa ttttgaagag gtacttggcc acgacttatt   120
ttcacctccg acctttcctt ccaggcggtg agactctgga ctgagagtgg ctttcacaat   180
ggaagggatc agtaatttca agacaccaag caaattatca gaaaaaaga aatctgtatt    240 atgttcaact ccaactataa atatcccggc ctctccgatt atgcagaagc ttggctttgg   300
tactggggta aatgtgtacc taatgaaaag atctccaaga gtttgtctc attctccttg    360 ggctgtaaaa aagattaatc ctatatgtaa tgatcattat cgaagtgtgt atcaaaagag   420
actaatggat gaagctaaga ttttgaaaag ccttcatcat ccaaacattg ttggttatcg   480
tgcttttact gaagccagtg atggcagtct gtgtcttgct atggaatatg gaggtgaaaa   540
gtctctaaat gacttaatag aagaacgata taaagccagc caagatccct ttccagcagc   600
cataatttta aaagttgctt tgaatatggc aagagggtta agtatctgc accaagaaaa    660 gaaactgctt catggagaca taaagtcttc aaatgttgta attaaaggcg atttgaaac    720 aattaaaatc tgtgatgtag gagtctctct accactggat gaaaatatga ctgtgactga   780
ccctgaggct tgttacattg gcacagaggc atggaaaccc aaagaagctg tggaggagaa   840
tggtgttatt actgacaagg cagacatatt tgcctttggc cttactttgt gggaaatgat   900
gactttatcg attccacaca ttaatctttc aaatgatgat gatgatgaag ataaaactt    960 tgatgaaagt gatttttgatg atgaagcata ctatgcagcc ttgggaacta ggccacctat   1020
taatatggaa gaactggatg aatcatacca gaaagtaatt gaactcttct ctgtatgcac   1080
taatgaagac cctaaagatc gtccttctgc tgcacacatt gttgaagctc tggaaacaga   1140
tgtctagtga tcatctcagc tgaagtgtgg cttgcgtaaa taactgttta ttccaaaata   1200
tttacatagt tactatcagt agttattaga ctctaaaatt ggcatatttc aggaccatag   1260
```

-continued

```
tttcttgtta acatatggat aactatttct aatatgaaat atgcttatat tggctataag    1320
cacttggaat tgtactgggt tttctgtaaa gttttagaaa ctagctacat aagtactttg    1380
atactgctca tgctgactta aaacactagc agtaaaacgc tgtaaactgt accattaaat    1440
tgaatgccat tactttatt aatgatcttt cttaaatatt ctatatttta atggatctac    1500
tgacattagc actttgtaca gtacaaaata aagtctacat ttgttaaaa cactgaacct    1560 tttgctgatg tgtttatcaa atgataactg gaagctgagg agaatatgcc tcaaaaagag    1620
tagctccttg gatacttcag actctggtta cagattgtct tgatctcttg gatctcctca    1680
gatcttcttt ggttttgct ttaatttatt aaatgtattt tccatactga gtttaaaatt    1740
tattaatttg taccttaagc atttcccagc tgtgtaaaaa caataaaact caaataggat    1800
gataaagaat aaaggacact ttgggtaaaa aaaaaaaaa                          1840
```

<210> SEQ ID NO 49
<211> LENGTH: 322
<212> TYPE: PRT
<213> ORGANISM: Homo sapiens
<220> FEATURE:
<223> OTHER INFORMATION: T-LAK cell-originated protein kinase (TOPK),
      spermatogenesis-related protein kinase (SPK), PDZ
      binding kinase (PBK), Nori-3, FLJ14385, A7870, BRC
      No. 456

<400> SEQUENCE: 49

```
Met Glu Gly Ile Ser Asn Phe Lys Thr Pro Ser Lys Leu Ser Glu Lys
  1               5                  10                  15

Lys Lys Ser Val Leu Cys Ser Thr Pro Thr Ile Asn Ile Pro Ala Ser
             20                  25                  30

Pro Ile Met Gln Lys Leu Gly Phe Gly Thr Gly Val Asn Val Tyr Leu
         35                  40                  45

Met Lys Arg Ser Pro Arg Gly Leu Ser His Ser Pro Trp Ala Val Lys
     50                  55                  60

Lys Ile Asn Pro Ile Cys Asn Asp His Tyr Arg Ser Val Tyr Gln Lys
 65                  70                  75                  80

Arg Leu Met Asp Glu Ala Lys Ile Leu Lys Ser Leu His His Pro Asn
                 85                  90                  95

Ile Val Gly Tyr Arg Ala Phe Thr Glu Ala Ser Asp Gly Ser Leu Cys
            100                 105                 110

Leu Ala Met Glu Tyr Gly Gly Glu Lys Ser Leu Asn Asp Leu Ile Glu
        115                 120                 125

Glu Arg Tyr Lys Ala Ser Gln Asp Pro Phe Pro Ala Ala Ile Ile Leu
    130                 135                 140

Lys Val Ala Leu Asn Met Ala Arg Gly Leu Lys Tyr Leu His Gln Glu
145                 150                 155                 160

Lys Lys Leu Leu His Gly Asp Ile Lys Ser Ser Asn Val Val Ile Lys
                165                 170                 175

Gly Asp Phe Glu Thr Ile Lys Ile Cys Asp Val Gly Val Ser Leu Pro
            180                 185                 190

Leu Asp Glu Asn Met Thr Val Thr Asp Pro Glu Ala Cys Tyr Ile Gly
        195                 200                 205

Thr Glu Pro Trp Lys Pro Lys Glu Ala Val Glu Glu Asn Gly Val Ile
    210                 215                 220

Thr Asp Lys Ala Asp Ile Phe Ala Phe Gly Leu Thr Leu Trp Glu Met
225                 230                 235                 240

Met Thr Leu Ser Ile Pro His Ile Asn Leu Ser Asn Asp Asp Asp Asp
                245                 250                 255
```

```
Glu Asp Lys Thr Phe Asp Glu Ser Asp Phe Asp Asp Glu Ala Tyr Tyr
            260                 265                 270

Ala Ala Leu Gly Thr Arg Pro Pro Ile Asn Met Glu Glu Leu Asp Glu
        275                 280                 285

Ser Tyr Gln Lys Val Ile Glu Leu Phe Ser Val Cys Thr Asn Glu Asp
    290                 295                 300

Pro Lys Asp Arg Pro Ser Ala Ala His Ile Val Glu Ala Leu Glu Thr
305                 310                 315                 320

Asp Val

<210> SEQ ID NO 50
<211> LENGTH: 1899
<212> TYPE: DNA
<213> ORGANISM: Homo sapiens
<220> FEATURE:
<223> OTHER INFORMATION: T-LAK cell-originated protein kinase (TOPK),
      spermatogenesis-related protein kinase (SPK), PDZ
      binding kinase (PBK), Nori-3, FLJ14385, A7870, BRC
      No. 456
<220> FEATURE:
<221> NAME/KEY: CDS
<222> LOCATION: (202)..(1170)
<223> OTHER INFORMATION: T-LAK cell-originated protein kinase (TOPK)

<400> SEQUENCE: 50
agcgcgcgac tttttgaaag ccaggagggt tcgaattgca acggcagctg ccgggcgtat      60
gtgttggtgc tagaggcagc tgcagggtct cgctgggggc cgctcgggac caattttgaa     120
gaggtacttg gccacgactt attttcacct ccgacctttc cttccaggcg gtgagactct     180
ggactgagag tggctttcac aatggaaggg atcagtaatt tcaagacacc aagcaaatta     240
tcagaaaaaa agaaatctgt tattatgttca actccaacta taaatatccc ggcctctccg     300
tttatgcaga agcttggctt tggtactggg gtaaatgtgt acctaatgaa aagatctcca     360
agaggtttgt ctcattctcc ttgggctgta aaaaagatta tcctatatg taatgatcat      420 tatcgaagtg tgtatcaaaa gagactaatg gatgaagcta gattttgaa aagccttcat      480 catccaaaca ttgttggtta tcgtgctttt actgaagcca atgatggcag tctgtgtctt     540
gctatggaat atggaggtga aaagtctcta aatgacttaa tagaagaacg atataaagcc     600
agccaagatc ttttccagc agccataatt ttaaaagttg ctttgaatat ggcaagaggg      660
ttaaagtatc tgcaccaaga aaagaaactg cttcatggag acataaagtc ttcaaatgtt     720
gtaattaaag gcgattttga aacaattaaa atctgtgatg taggagtctc tctaccactg     780
gatgaaaata tgactgtgac tgaccctgag gcttgttaca ttggcacaga gccatggaaa     840
cccaaagaag ctgtggagga aatggtgtt attactgaca aggcagacat atttgccttt     900
ggccttactt tgtgggaaat gatgacttta tcgattccac acattaatct ttcaaatgat     960
gatgatgatg aagataaaac ttttgatgaa agtgattttg atgatgaagc atactatgca    1020
gcgttgggaa ctaggccacc tattaatatg gaagaactgg atgaatcata ccagaaagta    1080
attgaactct ctctgtatg cactaatgaa gaccctaaag atcgtccttc tgctgcacac    1140
attgttgaag ctctggaaac agatgtctag tgatcatctc agctgaagtg tggcttgcgt    1200
aaataactgt ttattccaaa atatttacat agttactatc agtagttatt agactctaaa    1260
attggcatat ttgaggacca tagtttcttg ttaacatatg gataactatt tctaatatga    1320
aatatgctta tattggctat aagcacttgg aattgtactg ggttttctgt aaagttttag    1380
aaactagcta cataagtact tgatactgc tcatgctgac ttaaaacact agcagtaaaa     1440
```

```
cgctgtaaac tgtaacatta aattgaatga ccattacttt tattaatgat ctttcttaaa    1500
tattctatat tttaatggat ctactgacat tagcactttg tacagtacaa aataaagtct    1560
acatttgttt aaaacactga acctttgct gatgtgttta tcaaatgata actggaagct     1620
gaggagaata tgcctcaaaa agagtagctc cttggatact tcagactctg gttacagatt    1680
gtcttgatct cttggatctc ctcagatctt tggttttgc tttaatttat taaatgtatt     1740
ttccatactg agtttaaaat ttattaattt gtaccttaag catttcccag ctgtgtaaaa    1800
acaataaaac tcaaatagga tgataaagaa taaggacac tttgggtacc agaaaaaaaa    1860
aaaaaaaaaa aaaaaaaaaa aaaaaaaaaa aaaaaaaa                            1899
```

<210> SEQ ID NO 51
<211> LENGTH: 322
<212> TYPE: PRT
<213> ORGANISM: Homo sapiens
<220> FEATURE:
<223> OTHER INFORMATION: T-LAK cell-originated protein kinase (TOPK),
      spermatogenesis-related protein kinase (SPK), PDZ
      binding kinase (PBK), Nori-3, FLJ14385, A7870, BRC
      No. 456

<400> SEQUENCE: 51

```
Met Glu Gly Ile Ser Asn Phe Lys Thr Pro Ser Lys Leu Ser Glu Lys
 1               5                  10                  15

Lys Lys Ser Val Leu Cys Ser Thr Pro Thr Ile Asn Ile Pro Ala Ser
            20                  25                  30

Pro Phe Met Gln Lys Leu Gly Phe Gly Thr Gly Val Asn Val Tyr Leu
        35                  40                  45

Met Lys Arg Ser Pro Arg Gly Leu Ser His Ser Pro Trp Ala Val Lys
    50                  55                  60

Lys Ile Asn Pro Ile Cys Asn Asp His Tyr Arg Ser Val Tyr Gln Lys
65                  70                  75                  80

Arg Leu Met Asp Glu Ala Lys Ile Leu Lys Ser Leu His His Pro Asn
                85                  90                  95

Ile Val Gly Tyr Arg Ala Phe Thr Glu Ala Asn Asp Gly Ser Leu Cys
            100                 105                 110

Leu Ala Met Glu Tyr Gly Gly Glu Lys Ser Leu Asn Asp Leu Ile Glu
        115                 120                 125

Glu Arg Tyr Lys Ala Ser Gln Asp Pro Phe Pro Ala Ala Ile Ile Leu
    130                 135                 140

Lys Val Ala Leu Asn Met Ala Arg Gly Leu Lys Tyr Leu His Gln Glu
145                 150                 155                 160

Lys Lys Leu Leu His Gly Asp Ile Lys Ser Ser Asn Val Val Ile Lys
                165                 170                 175

Gly Asp Phe Glu Thr Ile Lys Ile Cys Asp Val Gly Val Ser Leu Pro
            180                 185                 190

Leu Asp Glu Asn Met Thr Val Thr Asp Pro Glu Ala Cys Tyr Ile Gly
        195                 200                 205

Thr Glu Pro Trp Lys Pro Lys Glu Ala Val Glu Glu Asn Gly Val Ile
    210                 215                 220

Thr Asp Lys Ala Asp Ile Phe Ala Phe Gly Leu Thr Leu Trp Glu Met
225                 230                 235                 240

Met Thr Leu Ser Ile Pro His Ile Asn Leu Ser Asn Asp Asp Asp Asp
                245                 250                 255

Glu Asp Lys Thr Phe Asp Glu Ser Asp Phe Asp Asp Glu Ala Tyr Tyr
            260                 265                 270
```

```
Ala Ala Leu Gly Thr Arg Pro Pro Ile Asn Met Glu Glu Leu Asp Glu
        275                 280                 285

Ser Tyr Gln Lys Val Ile Glu Leu Phe Ser Val Cys Thr Asn Glu Asp
    290                 295                 300

Pro Lys Asp Arg Pro Ser Ala Ala His Ile Val Glu Ala Leu Glu Thr
305                 310                 315                 320

Asp Val

<210> SEQ ID NO 52
<211> LENGTH: 4
<212> TYPE: PRT
<213> ORGANISM: Artificial Sequence
<220> FEATURE:
<223> OTHER INFORMATION: endoplasmic reticulum retention sequence

<400> SEQUENCE: 52

Lys Asp Glu Leu
1
```